(12) United States Patent
Wu et al.

(10) Patent No.: US 8,933,116 B2
(45) Date of Patent: Jan. 13, 2015

(54) GAMMA SECRETASE INHIBITORS

(75) Inventors: Wen-Lian Wu, Edison, NJ (US); Duane A. Burnett, Bernardsville, NJ (US); William J. Greenlee, Teaneck, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/009,418

(22) PCT Filed: Apr. 4, 2012

(86) PCT No.: PCT/US2012/032039
§ 371 (c)(1),
(2), (4) Date: Oct. 2, 2013

(87) PCT Pub. No.: WO2012/138678
PCT Pub. Date: Oct. 11, 2012

(65) Prior Publication Data
US 2014/0018342 A1 Jan. 16, 2014

Related U.S. Application Data

(60) Provisional application No. 61/471,329, filed on Apr. 4, 2011.

(51) Int. Cl.
| | | |
|---|---|---|
| *A61K 31/352* | (2006.01) | |
| *C07D 493/06* | (2006.01) | |
| *A61K 31/5377* | (2006.01) | |
| *A61K 45/06* | (2006.01) | |
| *A61K 31/453* | (2006.01) | |
| *C07D 493/04* | (2006.01) | |
| *A61K 31/35* | (2006.01) | |
| *A61K 31/4178* | (2006.01) | |
| *A61K 31/496* | (2006.01) | |
| *A61K 31/397* | (2006.01) | |
| *A61K 31/665* | (2006.01) | |
| *A61K 31/4025* | (2006.01) | |
| *A61K 31/422* | (2006.01) | |

(52) U.S. Cl.
CPC ............. *A61K 31/5377* (2013.01); *A61K 45/06* (2013.01); *A61K 31/453* (2013.01); *C07D 493/04* (2013.01); *A61K 31/35* (2013.01); *A61K 31/4178* (2013.01); *A61K 31/496* (2013.01); *A61K 31/397* (2013.01); *A61K 31/665* (2013.01); *A61K 31/4025* (2013.01); *A61K 31/422* (2013.01)

USPC ........... 514/455; 549/356; 549/381; 549/387; 514/449; 514/451; 514/454

(58) Field of Classification Search
CPC ... A61K 31/352; C07D 311/80; C07D 493/06
USPC .......... 549/356, 381, 385, 387; 514/449, 451, 514/454, 455
See application file for complete search history.

(56) References Cited

U.S. PATENT DOCUMENTS

| | | | |
|---|---|---|---|
| 7,655,675 B2 | 2/2010 | Nadin | |
| 8,067,621 B2* | 11/2011 | Asberom et al. | ............... 549/387 |
| 8,569,521 B2* | 10/2013 | Asberom et al. | ............... 549/387 |
| 8,664,411 B2* | 3/2014 | Wu et al. | ....................... 549/387 |
| 2008/0058316 A1 | 3/2008 | Eberhart | |

FOREIGN PATENT DOCUMENTS

WO    WO2009/008980    1/2009

OTHER PUBLICATIONS

International Preliminary Examination Report for PCT/US2012/032039, issued Oct. 8, 2013.

* cited by examiner

*Primary Examiner* — Golam M M Shameem
(74) *Attorney, Agent, or Firm* — J. Eric Thies; John C. Todaro

(57) ABSTRACT

Disclosed herein are compounds of Formula (I) and pharmaceutically acceptable salts thereof, wherein each of the substituents is given the definition as set forth in the specification and claims. Also disclosed are pharmaceutical compositions containing the compound of Formula (I) and use of the compound in the treatment of neurodegenerative diseases or conditions such as Alzheimer's disease.

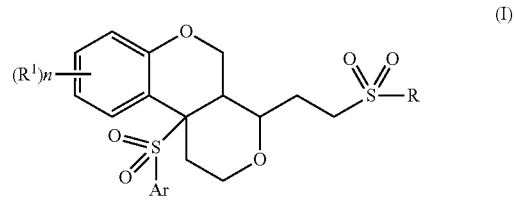

15 Claims, No Drawings

GAMMA SECRETASE INHIBITORS

CROSS REFERENCE TO RELATED APPLICATION

This application is entered into national stage examination under 37 U.S.C. 371 and stems from international patent application No. PCT/US2012/032039 filed on Apr. 4, 2012, which claims priority to application No. 61/471,329 filed Apr. 4, 2011.

BACKGROUND OF THE INVENTION

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

Aβ protein, which is a metabolite of amyloid precursor protein (hereinafter referred to as APP), is considered to be greatly involved in degeneration and loss of neurons as well as onset of demential conditions (for example, see Klein W L, et al *Proceeding National Academy of Science USA*, Sep. 2, 2003, 100(18), p. 10417-22), suggesting a molecular basis for reversible memory loss.

Nitsch R M, and 16 others, *Antibodies against β-amyloid slow cognitive decline in Alzheimer's disease*, Neuron, May 22, 2003, 38(4), p. 547-554) suggest that the main components of Aβ protein are Aβ40 consisting of 40 amino acids and Aβ42 having two additional amino acids at the C-terminal. The Aβ40 and Aβ42 tend to aggregate (for example, see Jarrell J T et al, *The carboxy terminus of the β amyloid protein is critical for the seeding of amyloid formation: implications for the pathogenesis of Alzheimer's disease*, Biochemistry, May 11, 1993, 32(18), p. 4693-4697) and constitute the main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer's disease and Down's syndrome*, Proceeding National Academy of Science USA, June 1985, 82(12), p. 4245-4249).

Furthermore, it is known that mutations of APP and presenelin genes, which are observed in familial Alzheimer's disease, increase production of Aβ40 and Aβ42 (for example, see Gouras G K, et al, *Intraneuronal Aβ42 accumulation in human brain*, American Journal of Pathology, January 2000, 156(1), p. 15-20. Also, see Scheuner D, et al, Nature Medicine, August 1996, 2(8), p. 864-870; and Forman M S, et al, *Differential effects of the Swedish mutant amyloid precursor protein on β-amyloid accumulation and secretion in neurons and normeuronal cells*, Journal of Biological Chemistry, Dec. 19, 1997, 272(51), p. 32247-32253). Therefore, compounds which reduce production of Aβ40 and Aβ42 are expected to be agents for controlling progress of Alzheimer's disease or for preventing the disease.

These Aβs are produced when APP is cleaved by beta secretase and subsequently cleaved by gamma secretase. In consideration of this, creation of inhibitors of γ-secretase and β-secretase has been attempted for the purpose of reducing production of Aβs. Many of these known secretase inhibitors are peptides or peptidomimetics such as L-685,458. L-685,458, an aspartyl protease transition state mimic, is a potent inhibitor of γ-secretase activity (Biochemistry, Aug. 1, 2000, 39(30), p. 8698-8704).

There is a need for new compounds, formulations, treatments and therapies to treat diseases and disorders associated with Aβ. It is, therefore, an object of this invention to provide compounds useful in the treatment or prevention or amelioration of such diseases and disorders.

SUMMARY OF THE INVENTION

Compounds of this invention herein termed gamma secretase inhibitors have the structure of Formula (I)

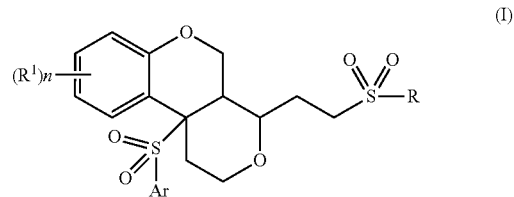

(I)

or a pharmaceutically acceptable salt thereof, wherein
R is —(C1-C6)alkyl-NR$^2$R$^3$, —(C1-C6)alkyl-R$^4$, or —R$^5$;
R$^1$ is independently selected from the group consisting halogen, —(C1-C6)alkyl, —CN, —CF$_3$, —O—(C1-C6)alkyl, —O-(halo(C1-C6)alkyl), —C(O)—O—(C1-C6)-OH-substituted (C1-C4)alkyl, -halo(C1-C6)alkyl, —(C1-C4)alkoxy-OH, —(C1-C4)alkoxy(C1-C4)alkoxy and S(O)$_2$(C1-C6)alkyl;
n is 0, 1, 2, or 3;
R$^2$ is H or —(C1-C6)alkyl;
R$^3$ is H, —(C1-C6)alkyl, -halo(C1-C6)alkyl, —(C3-C6)cycloalkyl, —(C1-C3)alkyl-(C3-C6)cycloalkyl optionally substituted with 1 or 2 L$^1$ groups or C(O)—(C1-C6)alkyl;
R$^4$ is —CN, —OH-substituted halo(C1-C6)alkyl, —(C3-C6) cycloalkyl optionally substituted with 1 or 2 L$^1$ groups, —(C3-C5)heterocycloalkyl containing 1-2 heteroatoms selected from N and O optionally substituted with 1 or 2 L$^1$ groups, —C(O)NH$_2$, —C(S)NH$_2$, —C(O)NH—(C1-C4) alkyl, —C(O)NH—(C3-C5)heterocycloalkyl containing 1-2 heteroatoms selected from N and O, —C(O)—NH—(C3-C6) cycloalkyl, —C(O)—(C3-C5)heterocycloalkyl containing 1-2 heteroatoms selected from N and O, —N((C$_1$-C$_4$)alkyl)-C(O)—(C1-C3)alkyl, —N((C1-C4)haloalkyl)-C(O)(C1-C3) alkyl), —S(O)$_2$—(C1-C3)alkyl or —P(O)—((C1-C3) alkoxy)$_2$;
R$^5$ is —OH or NH$_2$ substituted halo(C1-C6)alkyl, —(C3-C5) heterocycloalkyl containing 1-2 heteroatoms selected from N and O optionally substituted with 1 or 2 L$^1$ groups, or —(C3-C5)cycloalkyl optionally substituted with 1 or 2 L$^1$ groups;
L$^1$ is independently selected from the group consisting of —CH$_3$, —NH$_2$, —OH, —C(O)—CH$_3$, =O and C(O)—NH$_2$;
Ar is selected from the group consisting of phenyl optionally substituted with 1 or 2 L$^2$ groups, and pyridyl optionally substituted with 1 or 2 L$^2$ groups; and
L$^2$ is independently selected from the group consisting of: halogen, —(C1-C6)alkyl, —CN, —CF$_3$, —O—(C1-C6) alkyl-O-(halo(C1-C6)alkyl), —C(O)—O—(C1-C6)alkyl, —OH— substituted (C1-C6)alkyl, halo(C1-C6)alkyl, —OH-substituted (C1-C4)alkoxy, —(C1-C4)alkoxy(C1-C4)alkoxy and S(O)$_2$(C1-C6)allyl.

In an embodiment, the present invention provides for pharmaceutical compositions comprising at least one compound of Formula (I). In another embodiment, the present invention provides for methods for inhibiting gamma secretase activity comprising administering a therapeutically effective amount of at least one compound of Formula (I) to a patient afflicted with a disease or condition amenable to treatment by inhibition of gamma secretase, e.g., Alzheimer's disease.

DETAILED DESCRIPTION OF THE INVENTION

As used above, and throughout this disclosure, the following terms, unless otherwise indicated, shall be understood to have the following meanings:

"At least one" means there is at least one, and examples include 1, 2 or 3, or 1 or 2, or 1.

"One or more" means the same as "at least one."

"Patient" and "subject" means an animal, such as a mammal, e.g., a human being, and is preferably a human being.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain or about 2 to about 3 carbon atoms in the chain. Branched means that one or more lower alkyl groups such as methyl, ethyl or propyl, are attached to a linear alkyl chain. "Lower alkyl" means a group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, hydroxy (—OH), alkoxy, alkylthio, amino, —NH(alkyl), —NH(cycloalkyl), —N(alkyl)$_2$, carboxy and C(O)O-alkyl. Non-limiting examples of suitable alkyl groups include methyl, ethyl, n-propyl, isopropyl and t-butyl.

"Alkylene" means a divalent aliphatic hydrocarbon radical derived from an alkyl group, as defined above. Both "open" valences may be on the same carbon atom, or on different carbon atoms. Examples of alkylene groups include $C_1$-$C_6$ alkylene groups, for example, $C_1$ to $C_4$ alkylene groups, and in another example, $C_1$-$C_3$ alkylene groups, and in another example $C_1$ to $C_2$ alkylene groups. Non-limiting examples of alkylene groups include —CH$_2$—, —CH$_2$—CH$_2$—, —CH(CH$_3$)—, etc.

"Cycloalkyl" means a non-aromatic mono- or multicyclic ring system comprising about 3 to about 10 carbon atoms, preferably about 3 to about 6 carbon atoms. The cycloalkyl can be optionally substituted as defined herein. More preferred cycloalkyl rings contain about 3 to about 5 ring atoms. Non-limiting examples of suitable saturated monocyclic cycloalkyls include cyclopropyl, cyclobutyl, cyclopentyl, cyclohexyl, cycloheptyl and the like, and non-limiting examples of non-aromatic, unsaturated monocyclic cycloalkyls include cyclopentenyl, cyclopentadienyl, cyclohexenyl, etc. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Fluorine, chlorine and bromine are preferred. A substituent which is a halogen atom means F, —Cl, —Br, or I, and "halo" means fluoro, chloro, bromo or iodo substituents bonded to the moiety defined, e.g., "haloalkyl" means an alkyl, as defined above, wherein one or more of the bonding positions on the alkyl moiety typically occupied by hydrogen atoms are instead occupied by a halo group.

"Heterocycloalkyl" means a non-aromatic monocyclic or multicyclic ring system comprising about 3 to about 10 ring atoms, preferably about 3 to about 6 ring atoms (3-5C atoms), in which one or more of the atoms in the ring system is an element other than carbon, for example nitrogen, oxygen or sulfur, alone or in combination. There are no adjacent oxygen and/or sulfur atoms present in the ring system. Any —NH in a heterocycloalkyl ring may exist in protected form, for example, as an —N(Boc), —N(CBz), —N(Tos) group and the like; such protected forms are also considered part of this invention. The heterocycloalkyl can be optionally substituted as defined herein. The nitrogen or sulfur atom of the heterocycloalkyl can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, oxazolidinyl, azetidinyl, tetrahydrofuranyl, tetrahydropyran, oxetin, imidazolinyl and tetrahydrothiophenyl as well as partially unsaturated momocyclic rings such as dihydroimidazolyl.

"Hydroxy (—OH) substituted alkyl" means an alkyl group substituted with a hydroxy (—OH) group in which alkyl is as previously defined. Preferred hydroxyalkyls contain lower alkyl. Non-limiting examples of suitable hydroxyalkyl groups include hydroxymethyl and 2-hydroxyethyl.

"NH$_2$-substituted halo(C1-C6)alkyl" means a haloalkyl group substituted with a NH$_2$ group in which haloalkyl is as previously defined. An example of a suitable NH$_2$-substituted halo(C1-C6)alkyl group is trifluoromethyl.

"Alkoxy" means an —O—(C1-C4)alkyl group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkoxyalkoxy" means (C1-C4)alkoxy-(C1-C4)alkoxy" and refers to alkoxy groups as defined above wherein at least one of the hydrogen atoms of the lower alkoxy group is replaced by an alkoxy group as defined above. Among the preferred lower alkoxyalkoxy groups are 2-methoxy-ethoxy and 3-methoxy-propoxy.

"Alkylsulfonyl" means an -alkyl-S(O$_2$) group. Preferred groups are those in which the alkyl group is a lower alkyl, e.g., C1-C2 alkyl. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties. For example, a phenyl optionally substituted with an indicated group of substituents includes unsubstituted phenyl as well as phenyl substituted with any of the indicated substituents.

It should also be noted that any carbon atom as well as any heteroatom with unsatisfied valences in the text, schemes, examples, Tables, etc. herein is assumed to have the sufficient number of hydrogen atom(s) to satisfy the valences.

When a functional group in a compound is termed "protected", this means that the group is present in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, New York, herein incorporated by reference in its entirety.

"Effective amount" or "therapeutically effective amount" is meant to describe an amount of compound or a composition of the present invention effective in inhibiting the formation and/or deposition of amyloid protein, and thus producing the desired therapeutic, ameliorative, inhibitory or preventative effect.

This invention provides compounds that are inhibitors (e.g., antagonists) of gamma-secretase (also termed "γ-secretase") and have the Formula (I):

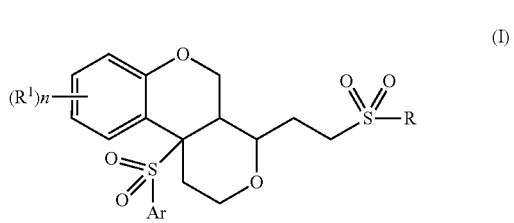
(I)

or a pharmaceutically acceptable salt thereof, wherein
R is —(C1-C6)alkyl-NR$^2$R$^3$, —(C1-C6)alkyl-R$^4$, or R$^5$;
R$^1$ is independently selected from the group consisting halogen, (C1-C6)alkyl, —CN, CF$_3$, —O—(C1-C6)alkyl, —O-(halo(C1-C6)alkyl), —C(O)—O—(C1-C6)-OH-substituted (C1-C4)alkyl, halo(C1-C6)alkyl, -alkoxy-OH, -alkoxy-alkoxy and S(O)$_2$(C1-C6)alkyl;
n is 0, 1, 2, or 3;
R$^2$ is H or —(C1-C6)alkyl;
R$^3$ is H, —(C1-C6)alkyl, -halo(C1-C6)alkyl, —(C3-C6)cycloalkyl, —(C1-C3)alkyl-(C3-C6)cycloalkyl optionally substituted with 1 or 2 L$^1$ groups or C(O)—(C1-C6)allyl;
R$^4$ is —CN, —OH-substituted halo(C1-C6)alkyl, —(C3-C6)cycloalkyl optionally substituted with 1 or 2 L$^1$ groups, —(C3-C5)heterocycloalkyl containing 1-2 heteroatoms selected from N and O optionally substituted with 1 or 2 L$^1$ groups, —C(O)NH$_2$, —C(S)NH$_2$, —C(O)NH—(C1-C4)alkyl, —C(O)NH—(C3-C5)heterocycloalkyl containing 1-2 heteroatoms selected from N and O, —C(O)—NH—(C3-C6)cycloalkyl, —C(O)—(C3-C5)heterocycloalkyl containing 1-2 heteroatoms selected from N and O, —N((C$_1$-C$_4$)alkyl)-C(O)—(C1-C3)alkyl, —N((C1-C4)haloalkyl)-C(O)(C1-C3)alkyl), —S(O)$_2$—(C1-C3)alkyl and —P(O)—((C1-C3)alkoxy)$_2$;
R$^5$ is —OH or NH$_2$ substituted halo(C1-C6)alkyl, —(C3-C5)heterocycloalkyl containing 1-2 heteroatoms selected from N and O optionally substituted with 1 or 2 L$^1$ groups, —(C3-C5)cycloalkyl optionally substituted with 1 or 2 L$^1$ groups;
L$^1$ is independently selected from the group consisting of —CH$_3$, —NH$_2$, —OH, —C(O)—CH$_3$, =O and C(O)—NH$_2$;
Ar is selected from the group consisting of phenyl optionally substituted with 1 or 2 L$^2$ groups, and pyridyl optionally substituted with 1 or 2 L$^2$ groups; and
L$^2$ is independently selected from the group consisting of halogen, (C1-C6)alkyl, —CN, —CF$_3$, —O—(C1-C6)alkyl —O-(halo(C1-C6)alkyl), —C(O)—O—(C1-C6)alkyl, —OH— substituted (C1-C6)alkyl, -halo(C1-C6)alkyl, —OH-substituted (C1-C4)alkoxy, —(C1-C4)alkoxy(C1-C4)alkoxy and S(O)$_2$(C1-C6)allyl.

The compounds of the invention have been found to be inhibitors of gamma-secretase activity and are believed to be useful in providing treatment of conditions or diseases states which can be treated by inhibition of gamma-secretase activity, for example, Alzheimer's disease, Down's Syndrome, mild cognitive impairment, glaucoma, cerebral amyloid angiopathy, stroke, dementia, microgliosis, brain inflammation, traumatic brain injury and olfactory function loss, and certain cancers, for example, T cell acute lymphoblastic leukemia, ovarian cancer, and lung cancers, e.g., non-small-cell lung carcinomas.

In one embodiment of the compounds of Formula (I), n is 2, R$^1$ is the same or different halogen, and the R$^1$ groups are bound to the phenyl moiety as shown in formula (II):

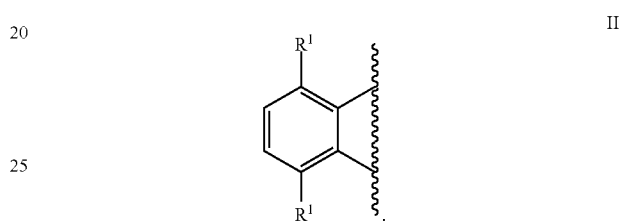
II

In another embodiment of the compounds of Formula (I), the halogen is fluoro.

In another embodiment of the compounds of Formula (I), in particular, when the halogen is fluoro, Ar is selected from the group consisting of
p-Cl-phenyl-, p-CN-phenyl-, p-CF$_3$-phenyl, pyridyl, and pyridyl substituted with 1 or 2 substituents independently selected from the group consisting of halogen, (C1-C6)alkyl, —CN, —CF$_3$, —O—(C1-C6)alkyl, —O-halo(C1-C6)alkyl, —C(O)—O—(C1-C6)alkyl, —OH-substituted (C1-C6)alkyl, -halo(C1-C6)alkyl, —OH substituted (C1-C4)alkoxy and (C1-C4)alkoxy(C1-C4)alkoxy. In one useful embodiment, Ar is selected from the group consisting of p-Cl-phenyl- and p-CF$_3$-phenyl.

In another embodiment of the compounds of Formula (I), R is —(C1-C3)alkyl-R$^4$.

In another embodiment of the compounds of Formula (I), in particular where R is —(C1-C3)alkyl-R$^4$, R$^4$ is —C(O)NH$_2$.

In another embodiment of the compounds of Formula (I), with respect to R$^4$ and R$^5$, the (C3-C5)heterocycloalkyl is selected from the group consisting of piperidyl, pyrrolidinyl, piperazinyl, morpholinyl, thiomorpholinyl, thiazolidinyl, oxazolidinyl, azetidinyl, tetrahydrofuranyl, tetrahydropyran, oxetin, imidazolinyl and tetrahydrothiophenyl.

In another embodiment, the compounds of Formula (I) have the following Formula (IA)

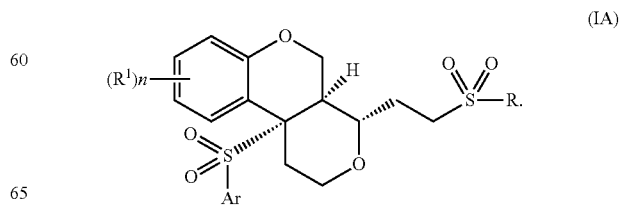
(IA)

In an embodiment of the compounds of Formula (IA), Ar is p-Cl-phenyl or p-CF$_3$-phenyl, n is 2, each R$^1$ is the same or different halogen, and the R$^1$ groups are bound to the phenyl moiety as shown in formula (II):

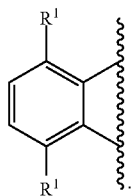

II

In an embodiment of the compounds of Formula (IA), R is —(C1-C3)alkyl-R$^4$ and R$^4$ is —C(O)NH$_2$.

In another embodiment, the compounds of Formula (I) are selected from the group consisting of compounds 6a-6t, 9a-9e, 24a-24c, 26e-26i, 27a-27g, 31b-31e, 32-34, 36, 39a-39g, 43a-43c, 45, 46a-46d, 47, 51a-51d, 56a-56f, 63c-63e, 64a-64d, 75, 76a, 76b, 82a-82d, 83-85, 87, 89, 95 and 99 or a pharmaceutically acceptable salt thereof.

In another embodiment, the compounds of Formula (I) are selected from the group consisting of 6i, 6j, 6p, 6o, 27a-27d, 31d, 31e, 45, 51a, 56d, 56e or a pharmaceutically acceptable salt thereof. In a useful embodiment, the compound of Formula (I) is compound 31d or a pharmaceutically acceptable salt thereof.

The compounds of Formula (I) can form salts, which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like.

Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Prodrugs and solvates of the compounds of the invention are also contemplated herein. The term "prodrug", as employed herein, denotes a compound that is a drug precursor that, upon administration to a subject, undergoes chemical conversion by metabolic or chemical processes to yield a compound of Formula (I) or a salt and/or solvate thereof. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule(s) is/are H$_2$O.

Compounds of Formula (I), and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula (I), and of the salts, solvates and prodrugs of the compounds of Formula (I), are intended to be included in the present invention.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled compounds of Formula I (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detection. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of Formula (I) can generally be prepared by following procedures analogous to those disclosed in the Schemes and/or in the Examples herein below, by substituting an appropriate isotopically labeled reagent for a non-isotopically labeled reagent.

Representative compounds of the invention include but are not limited to the compounds and Examples described herein.

The compounds according to the invention have pharmacological properties; in particular, the compounds of Formula (I) can inhibit gamma-secretase, and are therefore useful in the treatment or prevention of neurodegenerative diseases, e.g., Alzheimer's disease and other neurodegenerative diseases or conditions as described below.

Pharmaceutical compositions can comprise at least one compound of Formula (I) or a pharmaceutically acceptable salt thereof and at least one pharmaceutically acceptable carrier. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., herein incorporated by reference in its entirety.

Liquid form preparations include solutions, suspensions and emulsions. Water or water-propylene glycol solutions for parenteral injection or addition of sweeteners and opacifiers for oral solutions, suspensions and emulsions are examples. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active compound, e.g., an effective amount to achieve the desired purpose.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The quantity of active compound in a unit dose of preparation may be varied or adjusted from about 0.1 mg to about 1000 mg, preferably from about 0.1 mg to about 750 mg, more preferably from about 0.1 mg to about 500 mg, and most preferably from about 0.1 mg to about 250 mg, according to the particular application. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.1 mg/day to about 1000 mg/day, in one to four divided doses.

As indicated above, the compounds of the invention are useful in the treatment of Alzheimer's disease. Accordingly, in another embodiment of this invention a method of treating Alzheimer's disease is provided comprising administering to a patient in need thereof a therapeutically effective amount of at least one compound of Formula (I) or a pharmaceutically acceptable salt thereof.

In another embodiment of the method of treating Alzheimer's disease, the method comprises administering to a patient in need thereof a therapeutically effective amount of at least one compound of Formula (I) or a pharmaceutically acceptable salt thereof, and a therapeutically effective amount of at least one drug selected from the group consisting of BACE inhibitors; muscarinic antagonists; cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB 1 receptor inverse agonists or CB 1 receptor antagonists; an antibiotic; growth hormone secretagogues; histamine H3 antagonists; AMPA agonists; PDE4 inhibitors; GABAA inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase; anti-Abeta vaccine; APP ligands; agents that upregulate insulin cholesterol lowering agents; cholesterol absorption inhibitors; fibrates; LXR agonists; LRP mimics; nicotinic receptor agonists; 1-13 receptor antagonists; histone deacetylase inhibitors; hsp90 inhibitors; ml muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux.

In another embodiment, a method of treating Alzheimer's disease is provided comprising administering an effective (i.e., therapeutically effective) amount of at least one compound of formula (I), in combination with a therapeutically effective amount of at least one cholinesterase inhibitor (such as, for example, (±)-2,3-dihydro-5,6-dimethoxy-2-[[1-(phenylmethyl)-4-piperidinyl]methyl]-1H-inden-1-one hydrochloride, i.e. donepezil hydrochloride, available as the Aricept® brand of donepezil hydrochloride), to a patient in need of treatment.

The invention also provides for a method of inhibiting the deposition of amyloid beta protein in, on or around neurological tissue is provided, the method comprising administering to a patient in need thereof a therapeutically effective amount of at least one compound of the Formula (I) or a pharmaceutically acceptable salt thereof.

As the compounds of Formula (I) inhibit gamma secretase activity, the invention also provides for a method of inhibiting gamma secretase is provided comprising administering to a patient in need thereof a therapeutically effective amount of at least one compound of the Formula (I) or a pharmaceutically acceptable salt thereof.

The compounds of Formula (I) are also useful in treating a neurodegenerative disease or condition selected from the group consisting of Down's Syndrome, mild cognitive impairment, glaucoma, cerebral amyloid angiopathy, stroke, dementia, microgliosis, brain inflammation, traumatic brain injury and olfactory function loss. The method of treatment comprises administering to a patient in need thereof a therapeutically effective amount of at least one compound of the Formula (I) or a pharmaceutically acceptable salt thereof.

The compounds of Formula (I) or a pharmaceutically acceptable salt thereof are also useful in treating cancers such as T-cell acute lymphoblastic leukemia, ovarian cancer, and lung cancers, e.g., non-small-cell lung carcinomas. The method of treatment of one of the aforementioned cancers comprises administering to a patient in need thereof a therapeutically effective amount of at least one compound of the Formula (I) or a pharmaceutically acceptable salt thereof.

The compounds of Formula (I) are also useful in treating the aforementioned cancers in combination with a therapeutically effective amount of another pharmaceutically active agent, e.g., a glucocorticoid such as dexamethasone.

EXAMPLES

The invention disclosed herein is exemplified by the following preparations and examples, which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz), XL-400 (400 MHz) or Brucker AVANCE 300 or 500 MHz spectrometer, and are reported as ppm down field from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min 10% $CH_3CN$, 5 min 95% $CH_3CN$, 7 min 95% $CH_3CN$, 7.5 min 10% $CH_3CN$, 9 min stop. The retention time and observed parent ion are given.

The following solvents, reagents, and conditions may be referred to by their abbreviations in parenthesis:

Acetyl (Ac), i.e., $CH_3C(O)$—
Butyl (Bu)
Cyclopropyl (Pr-c)
Dichloroethane (DCE)
Dichloromethane (DCM)
Diethyl ether ($Et_2O$)
Diisobutylaluminum hydride (DIBAL-H)
Dimethyl formamide (DMF)
Ethanol (EtOH)
Ethyl (Et)
Ethyl acetate (EtOAc)
High resolution mass spectrometry (HRMS)
Lithium diisopropyl amide (LDA)
Liquid chromatography/mass spectrometry (LCMS)
m-Chloroperoxybenzoic acid (mCPBA)
Mesyl (Ms), i.e., —$S(O)_2CH_3$
Methanol (MeOH)
Methyl (Me)
Nuclear magnetic resonance spectroscopy (NMR)
Preparative thin-layer chromatography (PTLC)
Pyridine (Pyr)
Room temperature (RT)
Tert-butyldimethylsilyl (TBS)
Tetrabutyl ammonium fluoride (TBAF)
Tetrahydrofuran (THF)
Trifluoroacetic acid (TFA)
Trimethylsilyl (TMS)
Trimethylsilyl chloride (TMSC1)
Triethylamine ($NEt_3$ or $Et_3N$)

Experimental Methods:

Unless otherwise noted, reagents and solvents were used as received from commercial suppliers. Purification by Preparative High Pressure Liquid Chromatography (Prep. HPLC) was performed on a Waters Symmetry C18 7 μm (19×300 mm) column with solvent gradient program described in Method 1.

| Method 1 | | | |
|---|---|---|---|
| Time (min) | Flow (mL/min) | % A | % B |
| 0.0 | 20.0 | 90 | 10 |
| 15.0 | 20.0 | 0 | 100 |
| 18.0 | 20.0 | 0 | 100 |

A = Water with 0.025% v/v Hydrochloric Acid
B = Acetonitrile
UV Detection @ 254 nm High Pressure Liquid Chromatography (HPLC) analyses were obtained using a Waters Symmetry C18 5 μm (4.6×250 mm) column with solvent gradient programs described in Method 2.

| Method 2 | | | |
|---|---|---|---|
| Time (min) | Flow (mL/min) | % A | % B |
| 0.0 | 1.0 | 90 | 10 |
| 15.0 | 1.0 | 0 | 100 |
| 20.0 | 1.0 | 0 | 100 |

A = Water with 0.1% v/v Trifluoroacetic Acid
B = Acetonitrile with 0.1% v/v Trifluoroacetic Acid
UV Detection @ 254 nm Liquid Chromatography Mass Spectroscopy (LC-MS) were obtained using a SunFire C18 5 μm (4.6×50 mm) column with solvent gradient program described in Method 3.

| Method 3 | | | |
|---|---|---|---|
| Time (min) | Flow (mL/min) | % A | % B |
| 0.0 | 1.0 | 90 | 10 |
| 4.0 | 1.0 | 0 | 100 |
| 6.0 | 1.0 | 0 | 100 |

A = Water with 0.05% v/v Trifluoroacetic Acid
B = Acetonitrile with 0.05% v/v Trifluoroacetic Acid
UV Detection @ 254 nm Mass Spectra were obtained on a Finnigan LCQ Duo LCMS ion trap electrospray ionization (ESI) mass spectrometer or a Waters ACQUITY UPLC LCMS ion trap atmospheric pressure chemical ionization (APCI) mass spectrometer.

Optical rotation data was obtained on a Perkin Elmer 341 polarimeter.

Compounds of Formula (I) can be prepared according to the procedures outlined below.

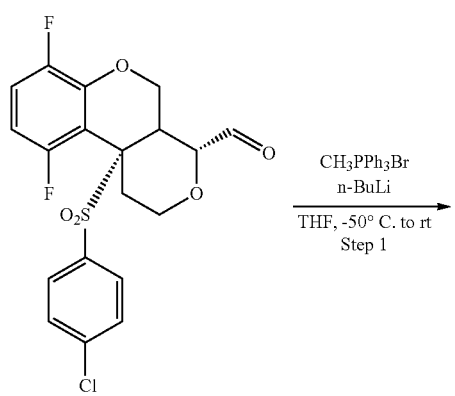

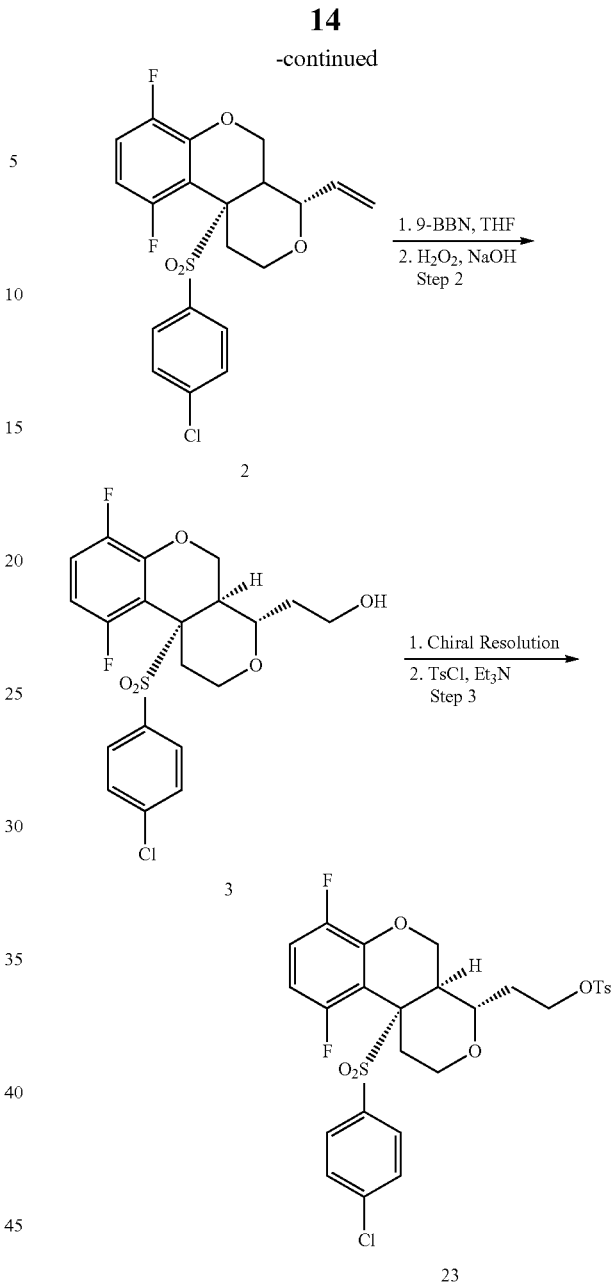

Step 1

A mechanically stirred suspension of 54.3 g (152 mmol) of methyl triphenylphosphonium bromide in 500 mL of THF was cooled to 50° C. and a solution of 65 mL (2.5 M in hexanes, 163 mmol) of n-BuLi was added dropwise over 15 min. The suspension was then warmed to 0° C., resulting in a cloudy solution. A second portion of 10.0 mL (25 mmol) of n-BuLi was added to give a clear solution which was re-cooled to 50° C. A solution of 50.0 g (117 mmol) of compound 1 (see WO2009/008980) in 200 mL of THF was then added dropwise from an addition funnel over a period of 15 min, after which time, the reaction mixture was allowed to warm to room temperature. The reaction was stirred for 18 h and then quenched with 500 mL of water. The resulting mixture was extracted with three 250 mL portions of ethyl acetate. The combined organic phases were washed with 250 mL of brine, dried over anhydrous magnesium sulfate, filtered, and concentrated. The residue was purified by column chromatography (silica, 0-20% EtOAc/heptane) to afford 31.1 g (62%) of 2 as a yellow solid: $^1$H NMR (CDCl$_3$ 500

MHz) δ 7.64 (d, J=10.9 Hz, 2H), 7.51 (d, J=8.7 Hz, 2H), 7.11 (ddd, J=14.1, 9.3, 4.7 Hz, 1H), 6.46 (ddd, J=11.9, 9.1, 4.0 Hz, 1H), 5.83 (ddd, J=17.6, 10.0, 7.8 Hz, 1H), 5.41-5.44 (m, 2H), 5.07 (dd, J=12.2, 3.0 Hz, 1H), 4.42 (d, J=12.0 Hz, 1H), 3.93 (ddd, J=6.6, 4.2, 2.4 Hz, 1H), 3.68 (dd, J=10.3, 7.9 Hz, 1H), 3.21 (ddd, J=12.0, 1.1, 1.1 Hz, 1H), 2.54-2.56 (m, 2H), 2.33-2.39 (m, 1H).

Step 2

To a solution of 4.00 g (9.30 mmol) of compound 2 in 70 mL of THF was added a solution of 9.50 g (39.0 mmol) of 9-borabicyclo[3.3.1]nonane (0.5 M in THF) dropwise at 0° C. After addition was complete, the reaction mixture was warmed to room temperature and stirred for 18 h. The mixture was then cooled to 0° C. and 70 mL of hydrogen peroxide (37% wt. in $H_2O$) and 70 mL of 3 N aqueous sodium hydroxide were added dropwise successively. The reaction mixture was then allowed to warm to room temperature and stirred at room temperature for 1 h. The mixture was diluted with 300 mL of water and extracted with three 250 mL portions of ethyl acetate. The combined extracts were washed with 500 mL of 6 N aqueous sodium hydroxide, dried over anhydrous magnesium sulfate, filtered, and concentrated under reduced pressure. The residue was purified by column chromatography (silica, 0-60% EtOAc/heptane) to afford 2.48 g (60%) of 3 as a white solid: MS: Calcd. for $C_{20}H_{19}ClF_2NaO_5S$ (MNa+), m/z=467.1. found 467.2. Retention time: 2.09 min.

Step 3

Compound 10 (2.1 g) was resolved on Chiral AS column eluting with 65% isopropanol in hexanes and 35 mL/min flow rate to give two enantiomers 3b (0.95 g, retention time 33.5-39.1 min, $[\alpha]_D^{20}$+98.4°) and 3a (0.98 g, retention time 41.3-49.3 min.,)$[\alpha]_D^{20}$−91.4°).

A solution of 0.98 g (2.05 mmol) of compound 3a, 0.82 g (4.3 mmol) of p-toluenesulfonyl chloride and 0.6 g (6.0 mmol) of triethylamine in 20 mL of dichloromethane was stirred at room temperature for 18 h. It was quenched with 80 mL of saturated sodium bicarbonate, and extracted with three 80 mL portions of dichloromethane. The combined organic extracts were concentrated and the residue was purified by chromatography eluting with a gradient of 2% to 45% of ethyl acetate in hexanes to give 1.33 g of compound 23. $^1$H NMR ($CDCl_3$ 400 MHz) δ 7.84 (d, J=8.4 Hz, 2H), 7.80 (d, J=8.4 Hz, 2H), 7.74 (d, J=8.4 Hz, 2H), 7.30 (d, J=8.4 Hz, 2H), 7.14 (m, 1H), 6.48 (m, 1H), 5.11 (d, J=10 Hz, 1H), 4.32 (d, J=12.4 Hz, 1H), 4.16 (m, 2H), 3.76 (m, 1H), 3.27 (m, 1H), 2.96 (t, J=12 Hz, 1H), 2.54 (m, 1H), 2.46 (m, 1H), 2.42 (s, 3H), 2.20 (m, 2H), 1.80 (m, 1H). MS: Calcd. for $C_{28}H_{26}F_5O_7S_2$ (MH+), 633.1. found 633.3. Retention time: 4.85 min.

Scheme 2

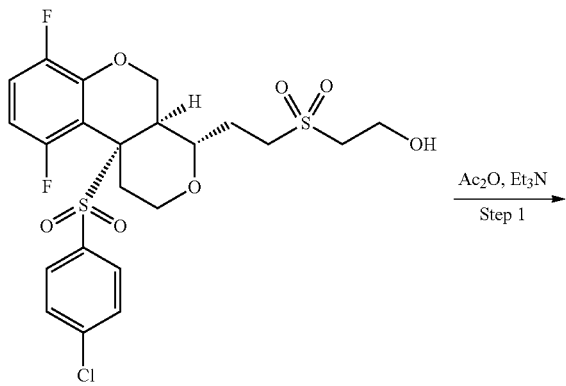

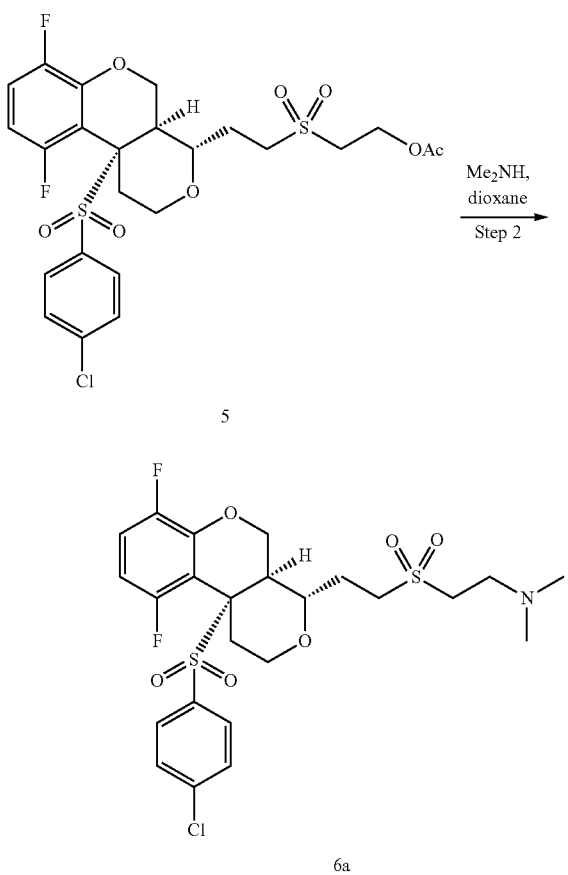

Step 1

A solution of 0.2 g (0.37 mmol) of the alcohol 4 (see WO 2009/008980), 0.1 g (1 mmol) of acetic anhydride, 0.2 g (0.2 mmol) of triethylamine in 5 mL of dichloromethane was stirred at room temperature overnight. It was concentrated; the residue was purified by chromatography eluting with a gradient of 10% to 60% ethyl acetate in hexanes to give 0.21 g of compound 5. $^1$H NMR ($CDCl_3$ 400 MHz) δ 7.70 (d, J=8.4H, 2H), 7.50 (d J=8.4 Hz, 2H), 7.10 (m, 1H), 6.48 (m, 1H), 5.16 (dd, J=12.4, 2.4 Hz, 1H), 4.48 (m, 3H), 3.87 (m, 1H), 3.34 (m, 4H), 3.17 (m, 1H), 3.05 (m, 1H), 2.57 (m, 2H), 2.42 (m, 1H), 2.27 (m, 1H), 2.03 (s, 3H), 2.0 (m, 1H); MS: Calcd. for $C_{24}H_{26}ClF_2O_8S_2$ (MH+), 579.1. found 579.3. Retention time: 4.68/7.5 min.

Step 2

A solution of 0.075 g (0.13 mmol) of compound 5 and 1 mL of 40% aqueous Me2NH and 3 mL of 1,4-dioxane was stirred at room temperature for three days. It was concentrated, the residue was purified by chromatography eluting with 1% to 5% of MeOH in $CH_2Cl_2$ plus 1% $NH_4OH$ to give 0.065 g of compound 6a. $^1$H NMR ($CDCl_3$ 400 MHz) δ 7.62 (d, J=8.8H, 2H), 7.50 (d, J=8.8 Hz, 2H), 7.09 (m, 1H), 6.45 (m, 1H), 5.15 (dd, J=12.4, 2.4 Hz, 1H), 4.44 (d, J=12.4 Hz, 1H), 3.87 (m, 1H), 3.33 (m, 2H), 3.10 (m, 4H), 2.77 (m, 2H), 2.54 (m, 1H), 2.41 (m, 1H), 2.26 (m, 1H), 2.25 (s, 6H), 2.0 (m, 1H). MS: Calcd. for $C_{24}H_{29}ClF_2NO_6S_2$ (MH+), 564.1. found 564.3. Retention time: 4.25/9 min.

Scheme 3

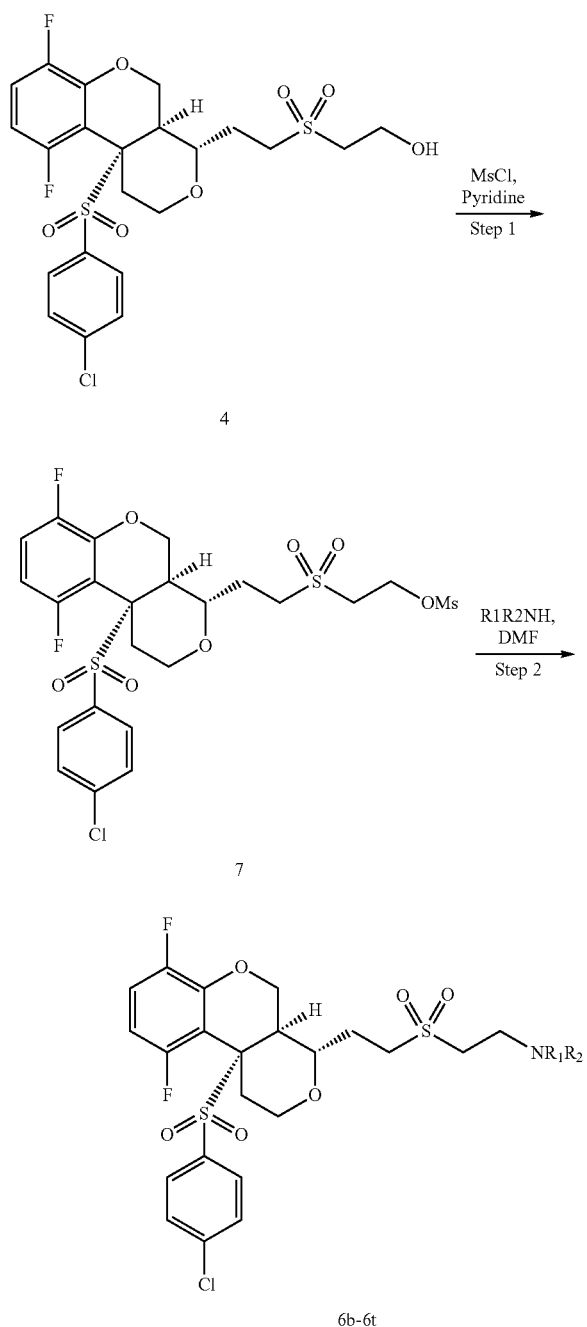

Step 1

To a solution of 0.4 g (0.74 mmol) of compound 4 in 7 mL of dichloromethane were added 0.24 g (3.0 mmol) of pyridine and 0.23 g (2.0 mmol) of methanesulfonyl chloride. The mixture was stirred at room temperature for 3 h, and concentrated. The residue was purified by chromatography eluting with 10% to 70% ethyl acetate in hexanes to give 0.38 g of compound 7. $^1$H NMR (CDCl$_3$ 400 MHz) δ 7.62 (d, J=8.8 Hz, 2H), 7.50 (d, J=8.8 Hz, 2H), 7.10 (m, 1H), 6.44 (m, 1H), 5.16 (dd, J=12.8, 2.8 Hz, 1H), 4.61 (t, J=5.6 Hz, 2H), 4.44 (d, J=12.8 Hz, 1H), 3.86 (m, 1H), 3.35 (m, 4H), 3.10 (m, 2H), 3.05 (s, 3H), 2.55 (m, 2H), 2.43 (m, 1H), 2.28 (m, 1H), 2.02 (m, 1H). MS: Calcd. for C$_{23}$H$_{26}$ClF$_2$O$_9$S$_3$ (MH$^+$), 615.0. found 615.3. Retention time: 5.38/9 min.

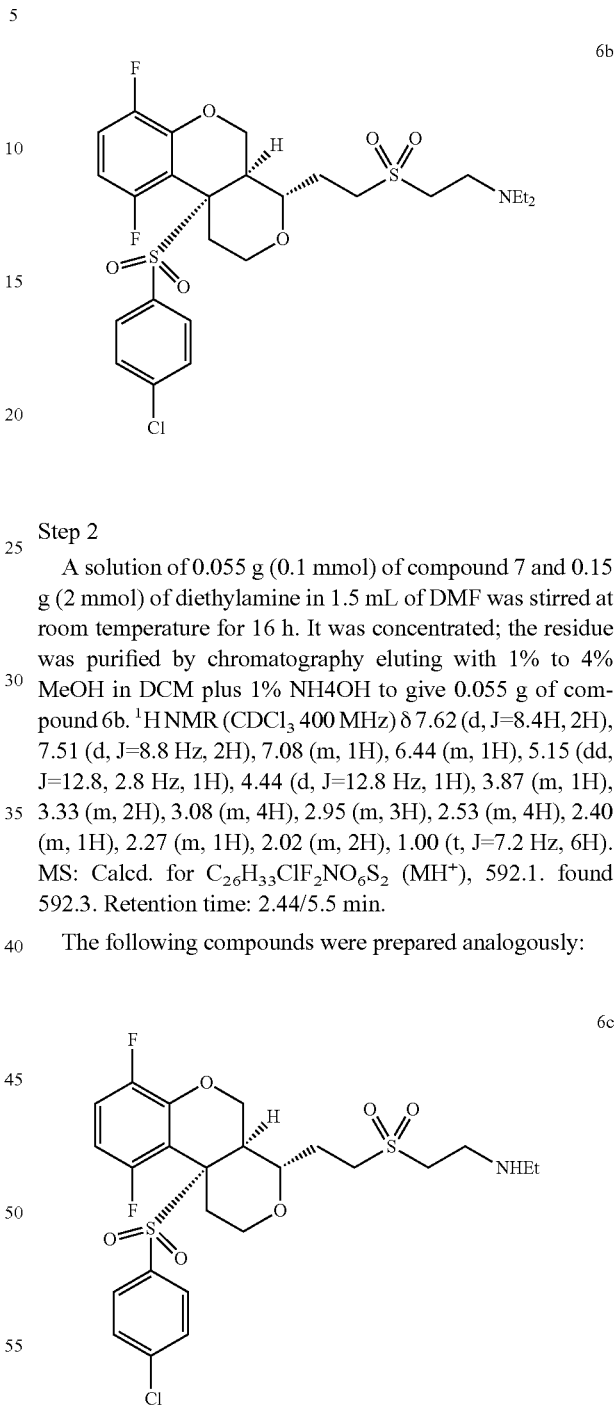

Step 2

A solution of 0.055 g (0.1 mmol) of compound 7 and 0.15 g (2 mmol) of diethylamine in 1.5 mL of DMF was stirred at room temperature for 16 h. It was concentrated; the residue was purified by chromatography eluting with 1% to 4% MeOH in DCM plus 1% NH4OH to give 0.055 g of compound 6b. $^1$H NMR (CDCl$_3$ 400 MHz) δ 7.62 (d, J=8.4H, 2H), 7.51 (d, J=8.8 Hz, 2H), 7.08 (m, 1H), 6.44 (m, 1H), 5.15 (dd, J=12.8, 2.8 Hz, 1H), 4.44 (d, J=12.8 Hz, 1H), 3.87 (m, 1H), 3.33 (m, 2H), 3.08 (m, 4H), 2.95 (m, 3H), 2.53 (m, 4H), 2.40 (m, 1H), 2.27 (m, 1H), 2.02 (m, 2H), 1.00 (t, J=7.2 Hz, 6H). MS: Calcd. for C$_{26}$H$_{33}$ClF$_2$NO$_6$S$_2$ (MH$^+$), 592.1. found 592.3. Retention time: 2.44/5.5 min.

The following compounds were prepared analogously:

$^1$H NMR (CDCl$_3$ 400 MHz) δ 7.61 (d, J=8.4H, 2H), 7.51 (d, J=8.4 Hz, 2H), 7.08 (m, 1H), 6.45 (m, 1H), 5.15 (dd, J=12.4, 2.4 Hz, 1H), 4.44 (d, J=12.4 Hz, 1H), 3.87 (m, 1H), 3.34 (m, 2H), 3.10 (m, 6H), 2.65 (q, J=7.2 Hz, 2H), 2.20-2.58 (m, 4H), 2.0 (m, 1H), 1.09 (t, J=7.2 Hz, 3H). MS: Calcd. for C$_{24}$H$_{29}$ClF$_2$NO$_6$S$_2$ (MH$^+$), 564.1. found 564.3. Retention time: 2.35/5.5 min.

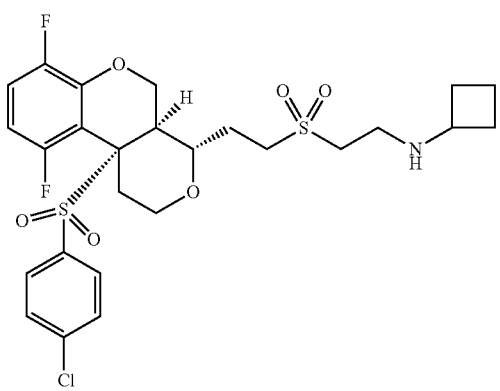

6d

¹H NMR (CDCl₃ 400 MHz) δ 7.61 (d, J=8.8H, 2H), 7.50 (d, J=8.8 Hz, 2H), 7.08 (m, 1H), 6.46 (m, 1H), 5.15 (dd, J=12.8, 2.4 Hz, 1H), 4.43 (d, J=12.8 Hz, 1H), 3.88 (m, 1H), 3.0-3.40 (m, 9H), 2.53 (m, 3H), 2.10-2.45 (m, 3H), 2.01 (m, 1H), 1.65 (m, 4H). MS: Calcd. for $C_{26}H_3ClF_2NO_6S_2$ (MH⁺), 590.1. found 590.3. Retention time: 3.31/7.5 min.

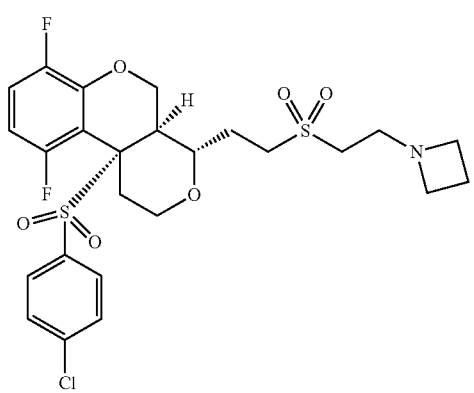

6e

¹H NMR (CDCl₃ 400 MHz) δ 7.62 (d, J=8.4H, 2H), 7.50 (d, J=8.4 Hz, 2H), 7.09 (m, 1H), 6.46 (m, 1H), 5.16 (dd, J=12.8, 2.4 Hz, 1H), 4.45 (d, J=12.8 Hz, 1H), 3.89 (m, 1H), 3.33 (m, 2H), 3.0-3.20 (m, 6H), 2.92 (m, 2H), 2.83 (m, 2H), 2.55 (m, 2H), 2.40 (m, 1H), 2.28 (m, 1H), 2.03 (m, 3H). MS: Calcd. for $C_{25}H_{29}ClF_2NO_6S_2$ (MH⁺), 576.1. found 576.3. Retention time: 2.38/5.5 min.

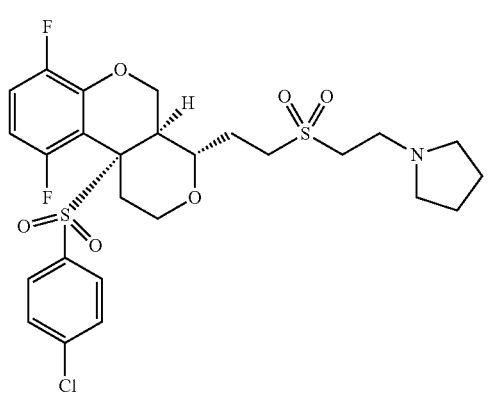

6f

¹H NMR (CDCl₃ 400 MHz) δ 7.61 (d, J=8.8H, 2H), 7.49 (d, J=8.8 Hz, 2H), 7.08 (m, 1H), 6.45 (m, 1H), 5.15 (dd, J=12.4, 2.8 Hz, 1H), 4.43 (d, J=12.4 Hz, 1H), 3.85 (m, 1H), 3.28-3.50 (m, 4H), 3.10 (m, 4H), 2.92 (m, 2H), 2.52 (m, 6H), 2.40 (m, 1H), 2.28 (m, 1H), 2.0 (m, 1H, 1.88 9m, 2H), 1.73 (m, 4H). MS: Calcd. for $C_{26}H_{31}ClF_2NO_6S_2$ (MH⁺), 590.1. found 590.3. Retention time: 2.38/5.5 min.

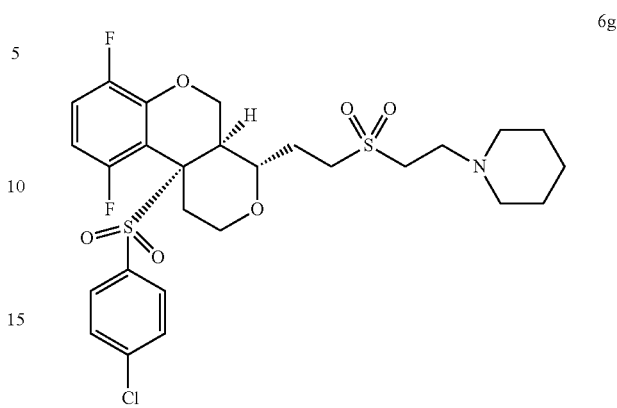

6g

¹H NMR (CDCl₃ 400 MHz) δ 7.61 (d, J=8.4H, 2H), 7.49 (d, J=8.4 Hz, 2H), 7.08 (m, 1H), 6.45 (m, 1H), 5.14 (dd, J=12.8, 2.8 Hz, 1H), 4.44 (d, J=12.4 Hz, 1H), 3.85 (m, 1H), 3.41 (m, 1H), 3.38 (m, 4H), 3.08 (m, 4H), 2.78 (m, 2H), 2.53 (m, 2H), 2.38 (m, 5H), 2.26 (m, 1H), 2.0 (m, 1H), 1.52 (m, 4H), 1.40 (m, 2H). MS: Calcd. for $C_{27}H_{33}ClF_2NO_6S_2$ (MH⁺), 604.1; found 604.3. Retention time: 2.45/5.5 min.

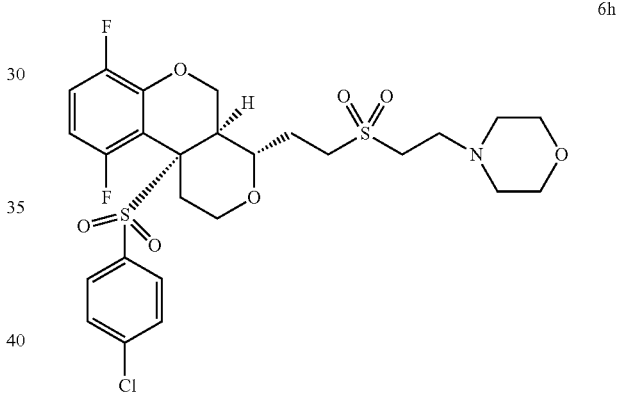

6h

¹H NMR (CDCl₃ 400 MHz) δ 7.61 (d, J=8.4H, 2H), 7.50 (d, J=8.4 Hz, 2H), 7.10 (m, 1H), 6.45 (m, 1H), 5.16 (dd, J=12.4, 2.4 Hz, 1H), 4.43 (d, J=12.4 Hz, 1H), 3.88 (m, 1H), 3.66 (m, 4H), 3.40 (m, 3H), 3.07 (m, 4H), 2.82 (m, 2H), 2.40-2.60 (m, 6H), 2.32 (m, 1H), 2.01 (m, 1H). MS: Calcd. for $C_{26}H_{31}ClF_2NO_7S_2$ (MH⁺), 606.1. found 606.3. Retention time: 2.39/5.5 min.

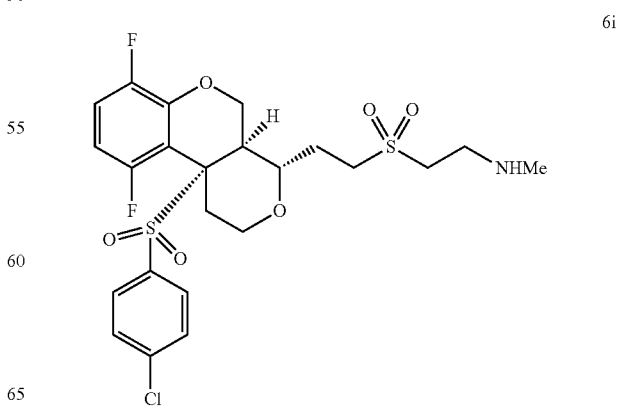

6i

¹H NMR (CDCl₃ 400 MHz) δ 7.61 (d, J=8.8H, 2H), 7.49 (d, J=8.4 Hz, 2H), 7.08 (m, 1H), 6.45 (m, 1H), 5.14 (dd, J=12.8, 2.8 Hz, 1H), 4.43 (d, J=12.8 Hz, 1H), 3.86 (m, 1H), 3.31 (m, 2H), 3.10 (m, 6H), 2.83 (d, J=4.0 Hz, 3H), 2.54 (m, 2H), 2.40 (m, 1H), 2.30 (m, 1H), 2.01 (m, 1H). MS: Calcd. for C₂₃H₂₇ClF₂NO₆S₂ (MH⁺), 550.1. found 550.3. Retention time: 2.30/5.5 min.

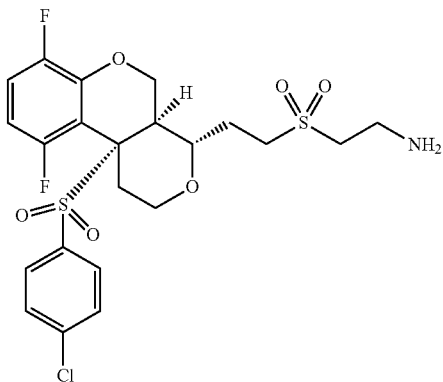

6j

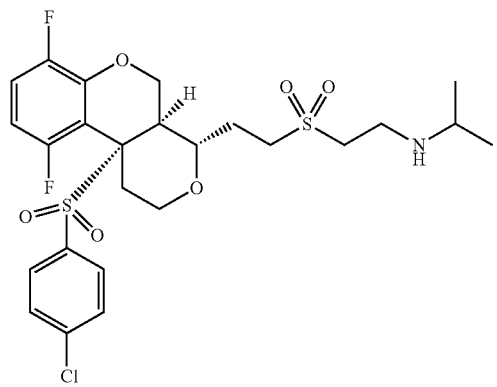

6l

¹H NMR (CDCl₃ 400 MHz) δ 7.56 (d, J=8.0H, 2H), 7.50 (d, J=8.4 Hz, 2H), 7.11 (m, 1H), 6.46 (m, 1H), 5.15 (dd, J=12.8, 2.0 Hz, 1H), 4.44 (d, J=12.8 Hz, 1H), 3.88 (m, 1H), 3.20-3.40 (m, 4H), 3.0-3.20 (m, 4H), 2.40-2.60 (m, 3H), 2.27 (m, 1H), 2.0 (m, 1H). MS: Calcd. for C₂₂H₂₅ClF₂NO₆S₂ (MH⁺), 536.1. found 536.3. Retention time: 4.10/9.0 min.

¹H NMR (CDCl₃ 400 MHz) δ 7.61 (d, J=8.4H, 2H), 7.49 (d, J=8.4 Hz, 2H), 7.08 (m, 1H), 6.45 (m, 1H), 5.13 (dd, J=12.4, 2.4 Hz, 1H), 4.42 (m, 1H), 3.86 (m, 1H), 3.32 (m, 2H), 3.10 (m, 6H), 2.77 (m, 1H), 2.20-2.50 (m, 4H), 2.0 (m, 1H), 1.01 (d, J=6.0 Hz, 6H). MS: Calcd. for C₂₅H₃₁ClF₂NO₆S₂ (MH⁺), 578.1. found 578.3. Retention time: 4.41/9.0 min.

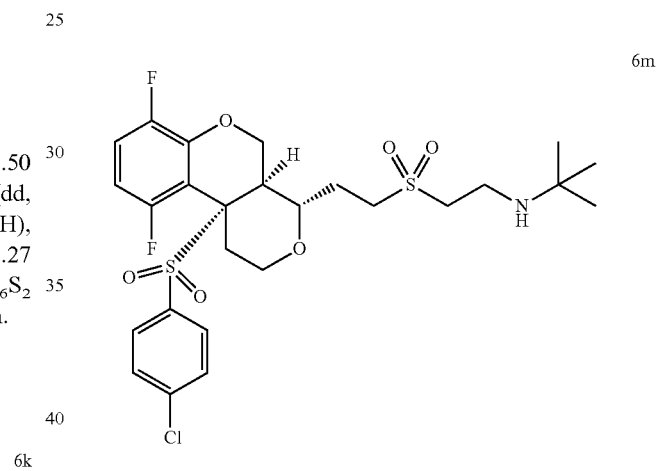

6m

¹H NMR (CDCl₃ 400 MHz) δ 7.62 (d, J=8.8H, 2H), 7.50 (d, J=8.8 Hz, 2H), 7.08 (m, 1H), 6.45 (m, 1H), 5.15 (dd, J=12.8, 2.8 Hz, 1H), 4.43 (d, J=12.8 Hz, 1H), 3.88 (m, 1H), 3.37 (m, 2H), 3.10 (m, 6H), 2.20-2.54 (m, 4H), 2.0 (m, 1H), 1.07 (s, 9H). MS: Calcd. for C₂₆H₃₃ClF₂NO₆S₂ (MH⁺), 592.1. found 592.3. Retention time: 4.55/9.0 min.

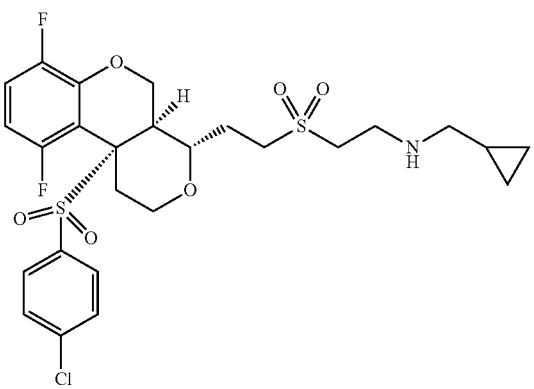

6k

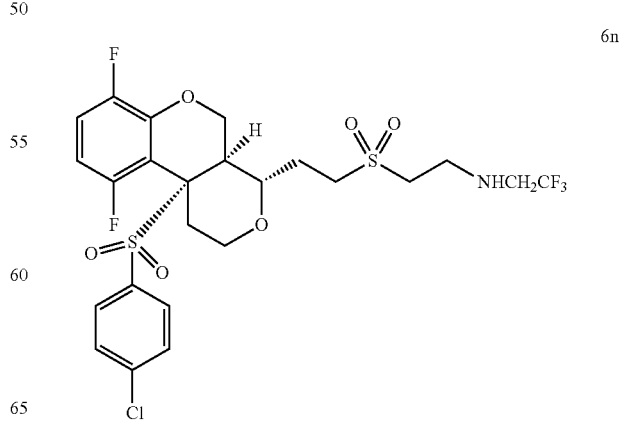

6n

¹H NMR (CDCl₃ 400 MHz) 7.61 (d, J=8.4H, 2H), 7.49 (d, J=8.4 Hz, 2H), 7.08 (m, 1H), 6.44 (m, 1H), 5.14 (dd, J=12.4, 2.4 Hz, 1H), 4.43 (d, J=12.4 Hz, 1H), 3.86 (m, 1H), 3.31 (m, 2H), 3.08 (m, 6H), 2.35-2.60 (m, 5H), 2.25 (m, 1H), 2.0 (m, 1H), 0.87 (m, 1H), 0.45 (m, 2H), 0.09 (m, 2H). MS: Calcd. for C₂₆H₃₁ClF₂NO₆S₂ (MH⁺), 590.1. found 590.3. Retention time: 4.53/9.0 min.

¹H NMR (CDCl₃ 400 MHz) δ 7.62 (d, J=8.8H, 2H), 7.49 (d, J=8.8 Hz, 2H), 7.10 (m, 1H), 6.48 (m, 1H), 5.16 (dd, J=12.8, 2.8 Hz, 1H), 4.43 (d, J=12.8 Hz, 1H), 3.85 (m, 1H), 3.0-3.40 (m, 10H), 2.20-2.60 (m, 4H), 2.0 (m, 1H). MS: Calcd. for $C_{24}H_{26}ClF_5NO_6S_2$ (MH⁺) 618.1; found 618.3. Retention time: 5.28/9.0 min.

6o

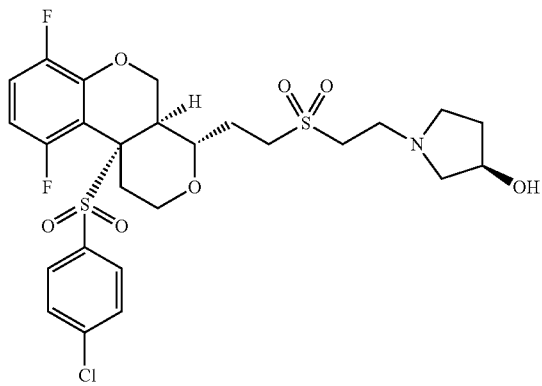

¹H NMR (CDCl₃ 400 MHz) δ 7.61 (d, J=8.4H, 2H), 7.49 (d, J=8.4 Hz, 2H), 7.10 (m, 1H), 6.45 (m, 1H), 5.14 (dd, J=12.4, 2.4 Hz, 1H), 4.44 (d, J=12.4 Hz, 1H), 4.24 (br, 1H), 3.88 (m, 1H), 3.55 (m, 1H), 3.33 (m, 1H), 2.80-3.20 (m, 8H), 2.20-2.60 (m, 8H), 2.0 (m, 1H). MS: Calcd. for $C_{26}H_{31}ClF_2NO_7S_2$ (MH⁺), 606.1. found 606.3. Retention time: 4.25/9.0 min.

6p

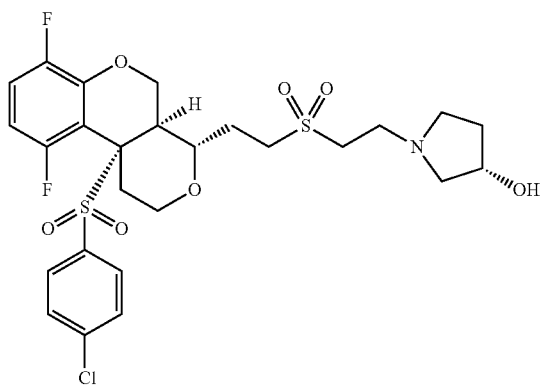

¹H NMR (CDCl₃ 400 MHz) δ 7.61 (d, J=8.8H, 2H), 7.49 (d, J=8.8 Hz, 2H), 7.08 (m, 1H), 6.45 (m, 1H), 5.15 (d, J=12.8 Hz, 1H), 4.44 (d, J=12.8 Hz, 1H), 4.27 (br, 1H), 3.88 (m, 1H), 3.50 (m, 1H), 3.34 (m, 1H), 2.95-3.15 (m, 7H), 2.80 (m, 1H), 2.20-2.60 (m, 8H), 2.0 (m, 1H), 1.72 (m, 1H). MS: Calcd. for $C_{26}H_{31}ClF_2NO_7S_2$ (MH⁺), 606.1. found 606.3. Retention time: 4.16/9.0 min.

6q

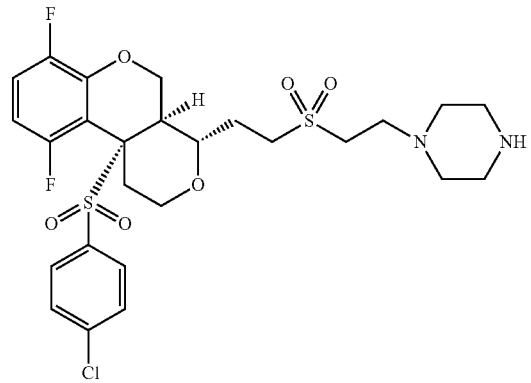

¹H NMR (CDCl₃ 400 MHz) δ 7.61 (d, J=8.8H, 2H), 7.49 (d, J=8.8 Hz, 2H), 7.08 (m, 1H), 6.45 (m, 1H), 5.14 (dd, J=12.8, 2.4 Hz, 1H), 4.43 (d, J=12.8 Hz, 1H), 3.86 (m, 1H), 3.20-3.50 (m, 3H), 3.10 (m, 3H), 2.80 (m, 7H), 2.20-2.60 (m, 8H), 2.0 (m, 1H). MS: Calcd. for $C_{26}H_{32}ClF_2N_2O_6S_2$ (MH⁺), 605.1. found 605.3. Retention time: 4.14/9.0 min.

6r

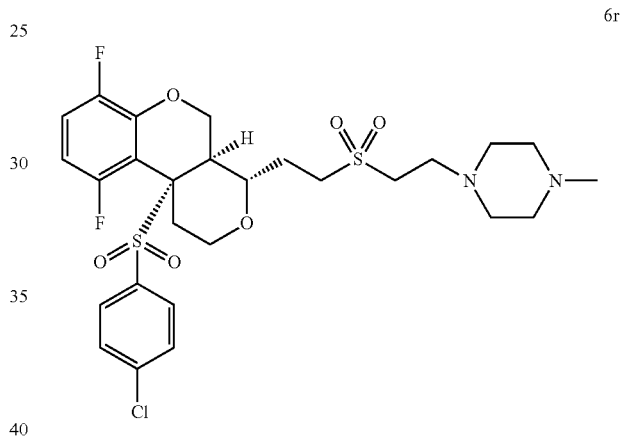

¹H NMR (CDCl₃ 400 MHz) δ 7.61 (d, J=8.8H, 2H), 7.49 (d, J=8.8 Hz, 2H), 7.08 (m, 1H), 6.45 (m, 1H), 5.15 (dd, J=12.8, 2.8 Hz, 1H), 4.43 (d, J=12.8 Hz, 1H), 3.87 (m, 1H), 3.40 (m, 2H), 3.10 (m, 3H), 2.80 (m, 2H), 2.20-2.60 (m, 10H), 2.23 (s, 3H), 2.0 (m, 1H). MS: Calcd. for $C_{27}H_{34}ClF_2N_2O_6S_2$ (MH⁺), 619.2. found 619.3. Retention time: 4.14/9.0 min.

6s

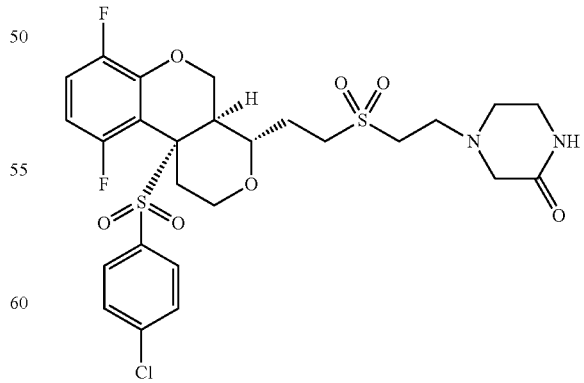

¹H NMR (CDCl₃ 400 MHz) δ 7.62 (d, J=8.8H, 2H), 7.50 (d, J=8.8 Hz, 2H), 7.08 (m, 1H), 6.45 (m, 1H), 6.16 (br, 1H), 5.14 (dd, J=12.8, 2.4 Hz, 1H), 4.42 (d, J=12.8 Hz, 1H), 3.85

(m, 1H), 3.48 (s, 2H), 3.38 (m, 4H), 3.10 (m, 6H), 2.95 (t, J=6.4 Hz, 2H), 2.72 (t, J=6.4 Hz, 2H), 2.40 (m, 1H), 2.30 (m, 1H), 2.02 (m, 1H). MS: Calcd. for $C_{26}H_{30}ClF_2N_2O_7S_2$ (MH$^+$), 619.1. found 619.3. Retention time: 3.33/7.5 min

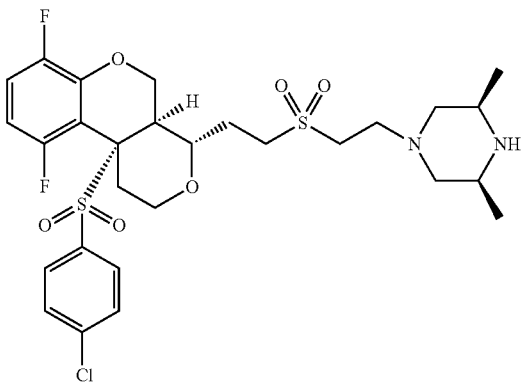

6t $^1$H NMR (CDCl$_3$ 400 MHz) δ 7.61 (d, J=8.0H, 2H), 7.49 (d, J=8.8 Hz, 2H), 7.07 (m, 1H), 6.45 (m, 1H), 5.13 (dd, J=12.8, 2.0 Hz, 1H), 4.42 (d, J=12.8 Hz, 1H), 3.86 (m, 1H), 3.40 (m, 2H), 3.10 (m, 4H), 2.60-2.85 (m, 7H), 2.50 (m, 1H), 2.40 (m, 1H), 2.28 (m, 1H), 2.0 (m, 1H), 1.42 (m, 2H), 1.08 (s, 3H), 1.02 (s, 3H). MS: Calcd. for $C_{28}H_{36}ClF_2N_2O_6S_2$ (MH$^+$), 633.2; found 633.3. Retention time: 3.19/7.5 min.

Scheme 4

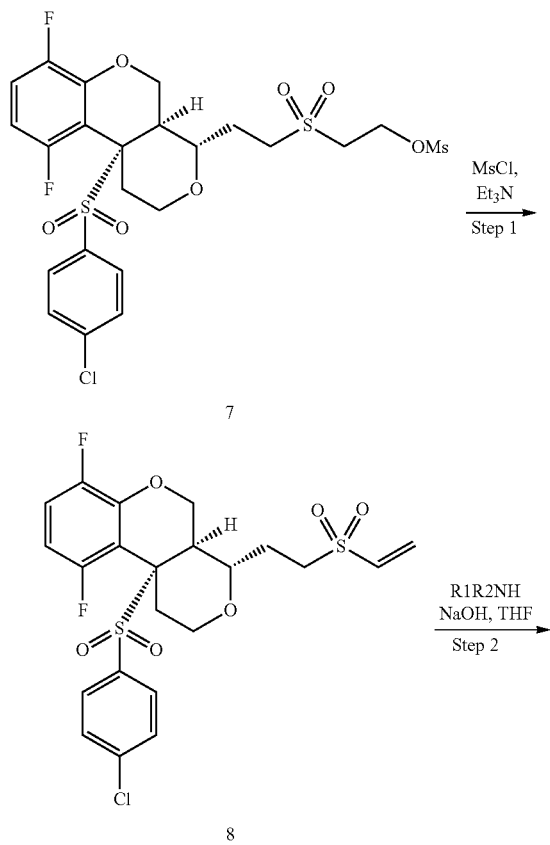

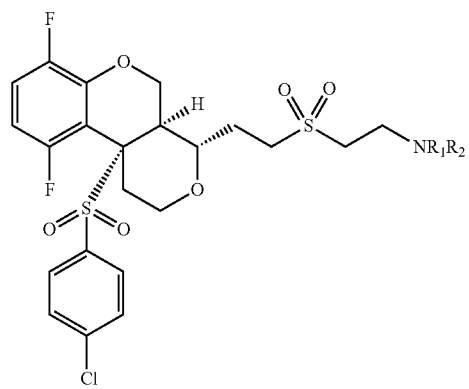

9a-9e

Step 1

A mixture of 0.65 g (0.11 mmol) of the misylate 7 and 0.4 g (0.4 mmol) of triethylamine in 6 mL of dichloromethane was stirred at room temperature for 18 h. It was purified by chromatography eluting with 0% to 100% ethyl acetate in hexanes to give 0.56 g of compound 8. $^1$H NMR (CDCl$_3$ 400 MHz) δ 7.61 (d, J=8.4H, 2H), 7.50 (d, J=8.4 Hz, 2H), 7.08 (m, 1H), 6.60 (dd, J=16.4, 10.0 Hz, 1H), 6.45 (m, 2H), 6.18 (d, J=10 Hz, 1H), 5.15 (dd, J=12.4, 2.4 Hz, 1H), 4.40 (d, J=12.4 Hz, 1H), 3.87 (m, 1H), 2.95-3.33 (m, 4H), 3.10 (m, 3H), 2.75 (m, 4H), 2.30 (m, 2H), 1.95 (m, 1H). MS: Calcd. for $C_{22}H_{22}ClF_2O_6S_2$ (MH$^+$), 519.1. found 519.3. Retention time: 3.02/5.5 min.

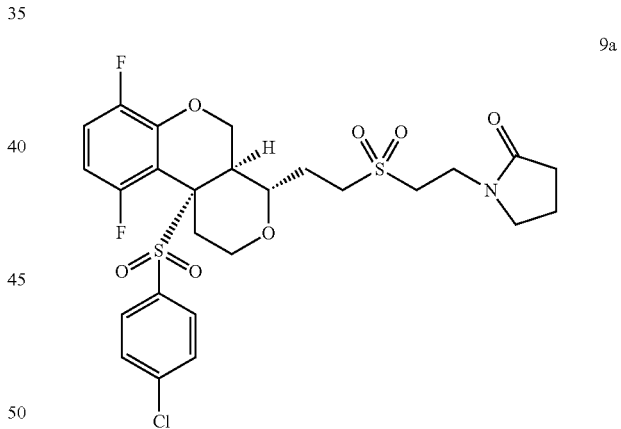

9a

Step 2

To a solution of 0.12 g (0.23 mmol) of compound 8 and 0.085 (1 mmol) of 2-pyrrolidinone in 5 mL of THF was added 20 mg of NaOH powder. The mixture was stirred at room temperature for 1.5 h, and concentrated. The residue was purified by chromatography eluting with 0% to 10% MeOH in CH$_2$Cl$_2$ plus 1% NH$_4$OH to give compound 9a. $^1$H NMR (CDCl$_3$ 400 MHz) δ 7.61 (d, J=8.4H, 2H), 7.49 (d, J=8.4 Hz, 2H), 7.08 (m, 1H), 6.46 (m, 1H), 6.0 (br, 1H), 5.13 (dd, J=12.8, 2.8 Hz, 1H), 4.43 (d, J=12.8 Hz, 1H), 3.88 (m, 1H), 3.70 (t, J=6.4 Hz, 2H), 3.48 (t, J=7.2 hz, 2H), 2.96-3.18 (m, 2H), 2.56 (m, 2H), 2.20-2.42 (m, 6H), 1.96-2.18 (m, 5H). MS: Calcd. for $C_{26}H_{29}ClF_2NO_7S_2$ (MH$^+$), 604.1. found 604.3. Retention time: 2.74/5.5 min.

The following compounds were prepared analogously:

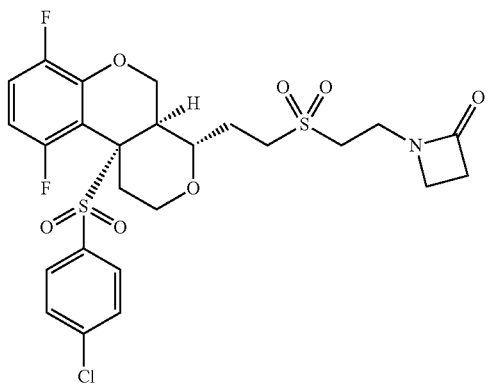
9b

¹H NMR (CDCl₃ 400 MHz) δ 7.61 (d, J=8.8H, 2H), 7.50 (d, J=8.8 Hz, 2H), 7.08 (m, 1H), 6.46 (m, 1H), 5.15 (dd, J=12.8, 2.8 Hz, 1H), 4.42 (d, J=12.8 Hz, 1H), 3.86 (m, 1H), 3.68 (t, J=6.8 Hz, 2H), 3.2-3.40 (m, 6H), 2.90-3.20 (m, 4H), 2.56 (m, 4H), 2.40 (m, 1H), 2.30 (m, 1H), 2.0 (m, 1H). MS: Calcd. for $C_{25}H_{27}ClF_2NO_7S_2$ (MH⁺), 590.1. found 590.3. Retention time: 4.91/9.0 min.

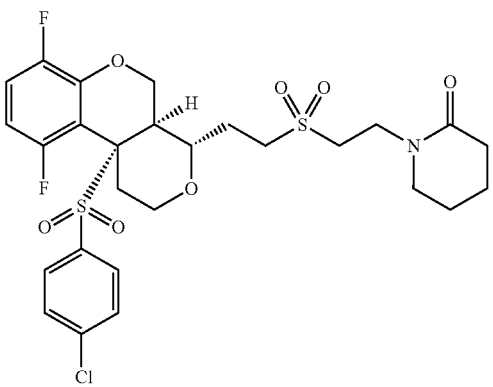
9c

¹H NMR (CDCl₃ 400 MHz) δ 7.61 (d, J=8.8H, 2H), 7.49 (d, J=8.8 Hz, 2H), 7.07 (m, 1H), 6.45 (m, 1H), 6.05 (s, 1H), 5.15 (dd, J=12.8, 2.8 Hz, 1H), 4.44 (d, J=12.8 Hz, 1H), 3.85 (m, 1H), 3.70 (m, 2H), 3.32 (t, J=6.8 Hz, 2H), 3.2-3.40 (m, 4H), 3.15 (m, 2H), 3.0 (m, 2H), 2.55 (m, 2H), 2.40 (m, 1H), 2.35 (t, J=6.4 Hz, 2H), 2.27 (m, 1H), 2.0 (m, 1H), 1.78 (m, 4H). MS: Calcd. for $C_{27}H_{31}ClF_2NO_7S_2$ (MH⁺), 618.1. found 618.3. Retention time: 5.14/9.0 min.

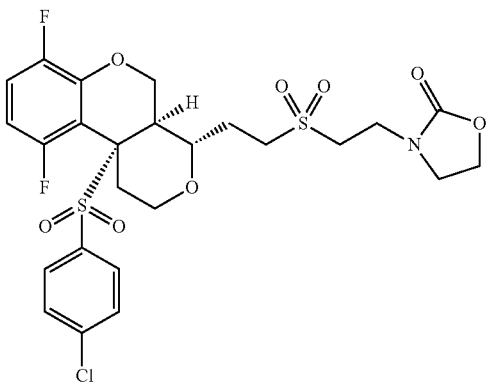
9d

¹H NMR (CDCl₃ 400 MHz) δ 7.62 (d, J=8.8H, 2H), 7.50 (d, J=8.8 Hz, 2H), 7.09 (m, 1H), 6.46 (m, 1H), 5.14 (dd, J=12.8, 2.4 Hz, 1H), 4.43 (d, J=12.8 Hz, 1H), 4.33 (t, J=7.6 hz, 2H), 3.88 (m, 1H), 3.73 (t, J=7.6 Hz, 2H), 3.30 (m, 2H), 3.-0-3.20 (m, 2H), 2.55 (m, 2H), 2.40 (m, 1H), 2.28 (m, 1H), 2.0 (m, 1H). MS: Calcd. for $C_{25}H_{27}ClF_2NO_8S_2$ (MH⁺), 606.1. found 606.3. Retention time: 4.18/7.5 min.

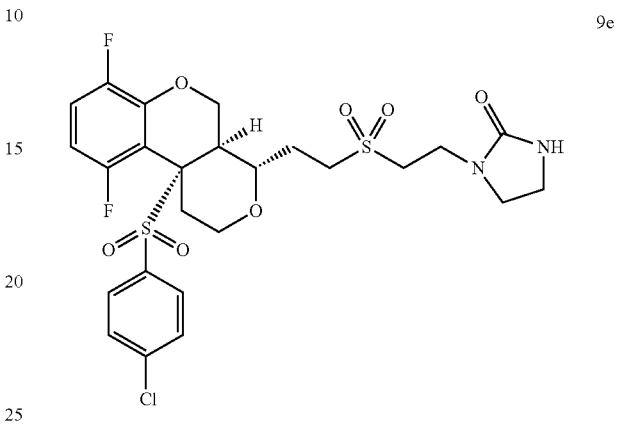
9e

¹H NMR (CDCl₃ 400 MHz) δ 7.62 (d, J=8.4H, 2H), 7.49 (d, J=8.4 Hz, 2H), 7.08 (m, 1H), 6.44 (m, 1H), 5.14 (dd, J=12.8, 2.8 Hz, 1H), 4.53 (s, 1H), 4.45 (d, J=12.8 Hz, 1H), 3.85 (m, 1H), 3.63 (t, J=6.4 Hz, 2H), 3.53 (t, J=6.4 Hz, 2H), 3.30 (m, 2H), 3.0-3.20 (m, 2H), 2.55 (m, 2H), 2.40 (m, 1H), 2.28 (m, 1H), 2.0 (m, 1H). MS: Calcd. for $C_{25}H_{28}ClF_2N_2O_7S_2$ (MH⁺), 605.1. found 605.3. Retention time: 2.61/5.5 min.

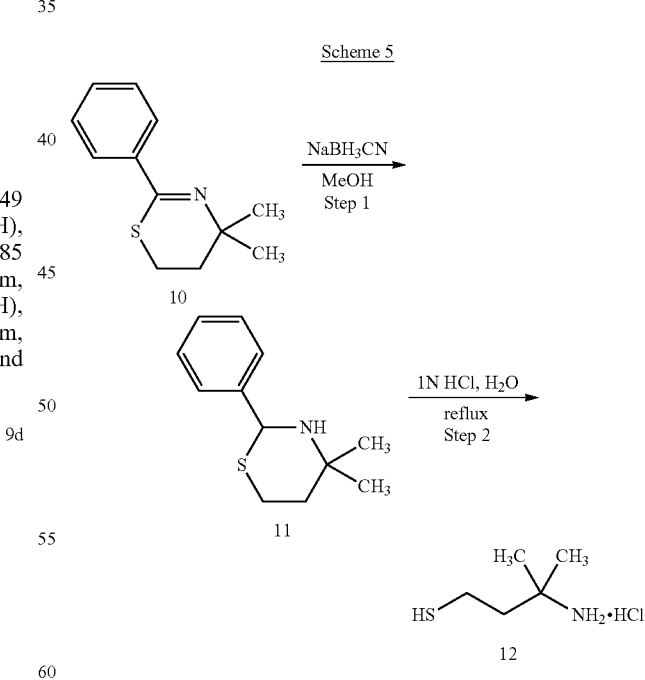

Scheme 5

Step 1

A solution of 2.06 g (10.0 mmol) of compound 10¹, 6.30 g (25.0 mmol) of pyridinium p-toluenesulfonate and 1.58 g (25.1 mmol) of sodium cyanoborohydride in 50 mL of methanol was stirred at room temperature for 18 h. The reaction was quenched with 25 mL of saturated aqueous sodium bicarbonate and extracted with three 30 mL portions of ethyl acetate. The combined extracts were dried over anhydrous magnesium sulfate, filtered, and concentrated under reduced pressure to give the crude product which was purified by column chromatography (silica, 0-20% EtOAc/heptane) to afford 0.823 g (40%) of 11 as a yellow oil: $^1$H NMR (CDCl$_3$ 500 MHz) δ 7.39-7.45 (m, 2H), 7.30-7.36 (m, 2H), 7.23-7.29 (m, 1H), 5.37 (s, 1H), 3.28-3.36 (m, 1H), 2.72 (dt, J=13.8, 3.8 Hz, 1H), 1.74 (ddd, J=13.7, 3.8, 2.8 Hz, 1H), 1.45-1.54 (m, 1H), 1.37 (s, 1H), 1.21 (s, 3H), 1.18 (s, 3H). MS: Calcd. for C$_{12}$H$_{18}$NS (MH$^+$), m/z=208.1. found 208.2.

Note 1: The preparation of 10 was previously described; see Liepa, A. J.; Saubern, S. Aust. J. Chem., 1997, 50, 755.

Step 2

A solution of 0.905 g (4.36 mmol) of compound 11 in 400 mL of 1 N hydrochloric acid was heated at reflux for 21 h. After this time, the reaction mixture was cooled to room temperature and washed with 200 mL of methylene chloride. The layers were separated and the aqueous layer was concentrated to dryness under reduced pressure. The residue was dissolved in 2 mL of methanol. To the resulting solution was added 10 mL of diethyl ether and the solvents decanted. The resulting residue was dried under high vacuum to give 0.698 g (>99%) of crude 12 as a light yellow solid which was used in the subsequent step without further purification. $^1$H NMR (CD$_3$OD 300 MHz) δ 2.53-2.59 (m, 2H), 1.91-1.96 (m, 2H), 1.34 (s, 6H).

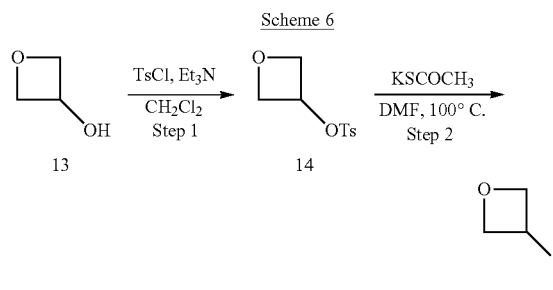

Scheme 6

Step 1

To a solution of 1.00 g (13.5 mmol) of compound 13 and 7.6 mL (54.0 mmol) of triethylamine in 27 mL of methylene chloride was added 5.15 g (27.0 mmol) of p-toluenesulfonyl chloride. The reaction mixture was stirred at room temperature overnight. After this time, the reaction was quenched with saturated 150 mL of aqueous sodium bicarbonate and extracted with three 50 mL portions of methylene chloride. The combined extracts were concentrated and the resulting residue was purified by column chromatography (silica, 0-25% EtOAc/hexanes) to give 1.22 g (94%) of 14 as white solid: $^1$H NMR (CDCl$_3$ 500 MHz) δ 7.78 (d, J=8.5 Hz, 2H), 7.36 (d, J=9.0 Hz, 2H), 5.29 (m, 1H), 4.69 (m, 4H), 2.46 (s, 3H).

Step 2

A solution of 0.50 g (2.19 mmol) of compound 14 and 0.75 g (6.57 mmol) of potassium thioacetate in 5 mL of N,N-dimethylformamide was stirred at 100° C. for 2 h. After this time the reaction mixture was cooled to room temperature and diluted with 100 mL of 5% aqueous lithium chloride. The resulting mixture was extracted with three 50 mL portions of methylene chloride. The combined extracts were dried over anhydrous sodium sulfate, filtered, and concentrated. The residue was purified by column chromatography (silica, 0-50% EtOAc/hexanes) to give 0.28 g (97%) of 15 as a yellow oil: $^1$H NMR (CDCl$_3$ 500 MHz) δ 5.06 (t, J=12.0 Hz, 2H), 4.61 (m, 3H), 2.34 (s, 3H).

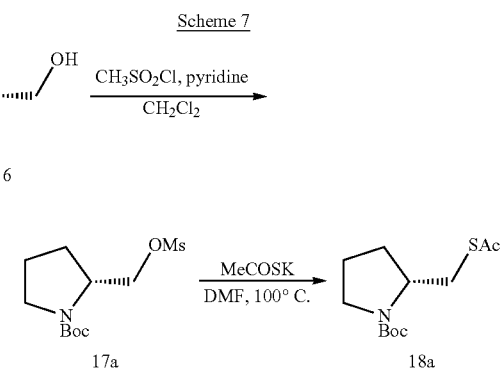

Scheme 7

Step 1

To a solution of 0.485 g (2.41 mmol) of compound 16 and 1.16 mL (14.5 mmol) of pyridine in 15 mL of methylene chloride was added 0.74 mL (9.64 mmol) of methanesulfonyl chloride at 0° C. The mixture was warmed to room temperature and stirred for 22 h under nitrogen. After this time, the reaction mixture was poured into 20 mL of H$_2$O and the layers were separated. The aqueous layer was extracted with three 20 mL portions of methylene chloride. The combined organics were washed with 15 mL of 1 N hydrochloric acid and 20 mL of brine, dried over anhydrous MgSO$_4$, filtered, and concentrated under reduced pressure. The resulting residue was purified by column chromatography (silica, 20-60% EtOAc/heptane) to afford 0.629 g (83%) of 17a as a clear oil: $^1$H NMR (CDCl$_3$ 300 MHz) δ 4.28-4.30 (m, 2H), 4.03-4.14 (m, 1H), 3.34-3.37 (m, 2H), 3.01 (s, 3H), 1.85-2.03 (m, 4H), 1.47 (s, 9H). MS: Calcd. for C$_{11}$H$_{21}$NNaO$_5$S (MNa$^+$), m/z=302.1. found 302.1. Retention time: 2.76 min.

The following compounds were prepared analogously:

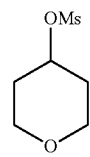

17b $^1$H NMR (CDCl$_3$ 500 MHz) δ 4.91 (ddd, J=12.7, 8.4, 4.0 Hz, 1H), 3.94 (m, 2H), 3.55 (m, 2H), 3.05 (s, 3H), 2.03-2.07 (m, 2H), 1.84-1.92 (m, 2H).

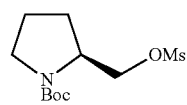

17c $^1$H NMR (CDCl$_3$ 300 MHz) δ 4.28-4.32 (m, 2H), 4.03-4.11 (m, 1H), 3.35-3.37 (m, 2H), 3.01 (s, 3H), 1.93-2.05 (m, 4H), 1.47 (s, 9H).

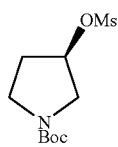

17d

¹H NMR (CDCl₃ 300 MHz) δ 5.25-5.27 (m, 1H), 3.43-3.72 (m, 4H), 3.05 (s, 3H), 2.13-2.28 (m, 2H), 1.47 (s, 9H).

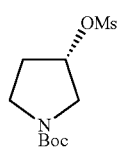

17e

¹H NMR (CDCl₃ 300 MHz) δ 5.25-5.28 (m, 1H), 3.49-3.68 (m, 4H), 3.05 (s, 3H), 2.12-2.28 (m, 2H), 1.47 (s, 9H).

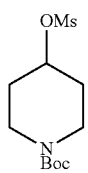

17f

¹H NMR (CDCl₃ 400 MHz) δ 4.86 (m, 1H), 3.68 (m, 2H), 3.28 (m, 2H), 3.01 (s, 3H), 1.94 (m, 2H), 1.81 (m, 2H), 1.32 (s, 9H).

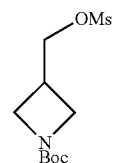

17g

¹H NMR (CD₃OD 400 MHz) δ 4.35 (d, J=6.8 Hz, 2H), 4.03 (t, J=8.4 Hz, 2H), 3.69 (m, 2H), 3.02 (s, 3H), 2.90 (m, 1H), 1.41 (s, 9H).

Step 2

A solution of 0.624 g (2.23 mmol) of compound 17a and 0.765 g (6.70 mmol) of potassium thioacetate in 12 mL of DMF was heated at 100° C. for 1 h. After this time, the reaction mixture was cooled to room temperature and diluted with 15 mL of saturated aqueous NH₄Cl and 10 mL of H₂O, and the layers separated. The aqueous layer was extracted with four 15 mL portions of methylene chloride. The combined organics were washed with two 10 mL portions of H₂O and 10 mL of brine, dried over anhydrous MgSO₄, filtered, and concentrated under reduced pressure to afford 0.570 g of crude 18a, which was used in the subsequent step without further purification. ¹H NMR (CDCl₃ 500 MHz) δ 3.88-3.95 (m, 1H), 3.26-3.42 (m, 3H), 2.88-3.15 (m, 1H), 2.34 (s, 3H), 1.90-2.00 (m, 2H), 1.76-1.81 (m, 1H), 1.69 (m, 1H), 1.49 (s, 9H). MS: Calcd. for C₁₂H₂₁NNaO₃S (MNa⁺), m/z=282.1. found 282.1. Retention time: 3.22 min.

The following compounds were prepared analogously:

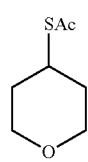

18b

¹H NMR (CDCl₃ 500 MHz) δ 3.91 (t, J=4.0 Hz, 1H), 3.88 (t, J=4.0 Hz, 1H), 3.66-3.70 (m, 1H), 3.52-3.57 (m, 2H), 2.34 (s, 3H), 1.89-1.92 (m, 2H), 1.63-1.71 (m, 2H).

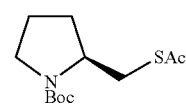

18c

MS: Calcd. for C₁₂H₂₁NNaO₃S (MNa⁺), m/z=282.1. found 282.1. Retention time: 3.04 min.

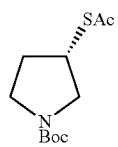

18d

¹H NMR (CD₃OD 500 MHz) δ 3.97 (m, 1H), 3.73 (m, 1H), 3.40 (m, 2H), 3.23 (m, 1H), 2.32 (s, 3H), 2.29 (m, 1H), 1.89 (m 1H), 1.45 (s, 9H).

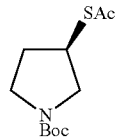

18e

MS: Calcd. for C₇H₁₂NO₃S (MH—C₄H₈⁺), m/z=190.1. found 190.1. Retention time: 2.84 min.

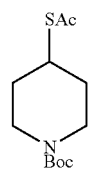

18f

¹H NMR (CD₃OD 400 MHz) δ 3.81 (m, 2H), 3.60 (m, 2H), 3.02 (m, 2H), 2.28 (s, 3H), 1.85 (m, 2H), 1.50 (m, 2H), 1.43 (s, 9H).

18g

Compound 18 g was prepared according to the procedure described in: Kazuhiko Hayashi, et al, Heterocycles 2002, 56, 433. ¹H NMR (CD₃OD 400 MHz) δ 4.57 (t, J=8.8 Hz, 1H), 3.86 (m, 1H), 4.37 (t, J=8.8 Hz, 1H), 4.20 (m, 1H), 3.95 (m, 1H), 3.85 (m, 1H), 2.32 (s, 3H), 1.82 (s, 3H). MS: Calcd. for $C_{19}H_{15}F_6O_4S$ (MH⁺), 453.1. found 0.3. Retention time: /9.0 min.

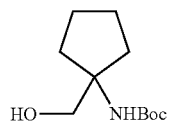

19

Compound 19 was prepared from the corresponding amino alcohol by a standard procedure of Boc protection. ¹H NMR (CD₃OD 400 MHz) δ 4.60 (br, 1H), 4.35 (s, 2H), 3.63 (d, J=5.6 Hz, 2H), 1.60-1.80 (m, 8H), 1.42 (s, 9H). MS: Calcd. for $C_{19}H_{15}F_6O_4S$ (MH⁺), 453.1. found 216.1. Retention time: 3.55/9.0 min.

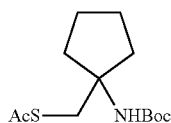

18h

¹H NMR (CD₃OD 400 MHz) δ 4.60 (br, 1H), 3.41 (m, 2H), 2.30 (s, 3H), 1.60-1.90 (m, 8H), 1.43 (s, 9H). MS: Calcd. for $C_{19}H_{15}F_6O_4S$ (MH⁺), 453.1. found 274.2. Retention time: 2.91/5.5 min.

Scheme 8

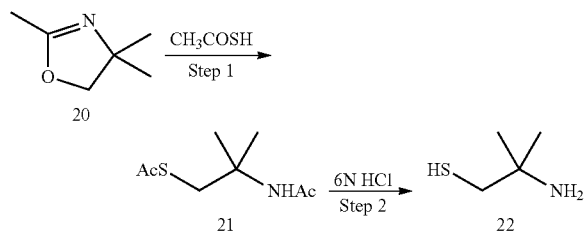

Step1

A mixture of 11.3 g (100 mmol) of 20 and 8.0 g (105 mmol) of thioacetic acid was stirred at 120° C. for 2 h. It was concentrated; the residue was distilled at reduced pressure (110-115° C./~0.5 mmHg) to give 15.1 g of compound 21 as an orange oil. ¹H NMR (CD₃OD 400 MHz) δ 5.67 (br, 1H), 3.26 (s, 2H), 2.34 (s, 3H), 1.87 (s, 3H), 1.34 (s, 6H). MS: Calcd. for $C_8H_{16}NO_2S$ (MH⁺), 190.1. found 190.3. Retention time: 1.33/5.5 min.

Step 2

A solution of 1.5 g (7.9 mmol) of compound 21 in 20 mL of 6 N HCl was stirred at reflux for 2 days. It was concentrated to give crude compound 22. ¹H NMR (CD₃OD 400 MHz) δ 8.24 (br, 1H), 4.40 (br, 2H), 2.46 (s, 2H), 1.44 (s, 6H).

Scheme 9

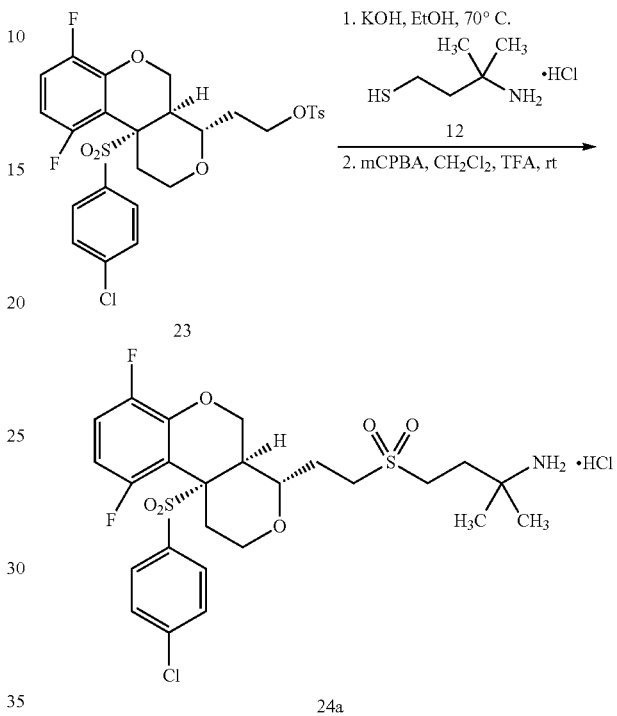

To a solution of 0.094 g (1.67 mmol) of potassium hydroxide in 1.67 mL of ethanol were added 0.13 g (0.835 mmol) of compound followed by compound 0.10 g (0.167 mmol) of 23 (WO 2009/008980) at room temperature under nitrogen. The resulting reaction mixture was stirred at room temperature for 5 min, then dipped into a preheated 70° C. oil bath and stirred at 70° C. for 1 h. After this time, the reaction mixture was cooled to room temperature and diluted with 50 mL of methylene chloride. The resulting mixture was washed with 10 mL of saturated aqueous Na₂CO₃, dried over anhydrous Na₂SO₄, filtered, and concentrated to dryness to give a white solid which was used in the subsequent step without further purification.

To a solution of the white solid obtained above in 2 mL of methylene chloride and 0.184 g (1.62 mmol) of trifluoroacetic acid was added 0.15 g (0.67 mmol) of 3-chloroperbenzoic acid (mCPBA). The resulting mixture was stirred for 4 h at room temperature. After this time, the reaction was quenched with 20 mL of 10% aqueous Na₂S₂O₃ and the resulting mixture was partitioned between 100 mL of methylene chloride and 50 mL of saturated aqueous NaHCO₃. The layers were separated and the aqueous layer was back-extracted with three 50 mL portions of methylene chloride. The combined organic layers were washed with three 50 mL portions of saturated aqueous NaHCO₃, dried over anhydrous Na₂SO₄, filtered, and concentrated under reduced pressure. The resulting residue was purified by column chromatography (silica, 20% MeOH/CH₂Cl₂) and then lyophilized (CH₃CN/HCl/water) to afford 0.071 g (69%) of 24a as an off-white solid: ¹H NMR (DMSO-d₆ 500 MHz) δ 8.10 (br s, 3H), 7.76 (d, J=9.0 Hz, 2H), 7.73 (d, J=9.0 Hz, 2H), 7.42 (ddd, J=10.0, 4.7, 4.7

Hz, 1H), 6.76 (ddd, J=12.4 Hz, 9.2, 4.0, 1H), 4.93 (dd, J=12.8, 2.6, 1H), 4.58 (d, J=12.7 Hz, 1H), 3.90-3.93 (m, 1H), 3.01-3.29 (m, 5H), 2.41-2.55 (m, 3H), 2.14-2.30 (m, 2H), 1.89-1.95 (m, 3H), 1.25 (s, 6H). MS: Calcd. for $C_{25}H_{31}ClF_2NO_6S_2$ (MH$^+$), m/z=578.1. found 578.3. Retention time: 2.33 min. LC-MS (Method 3) 96.8% (AUC), $t_R$=2.33 min. $[\alpha]^{25}_D$=−115.6° (c 0.45, MeOH).

The following compounds were prepared analogously:

24b

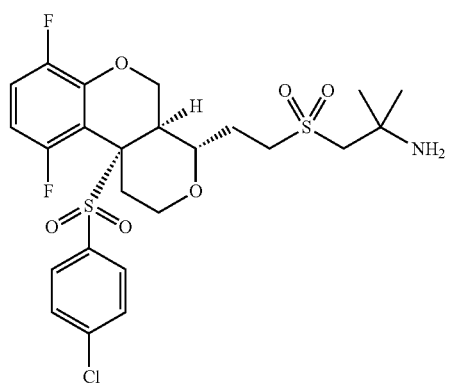

$^1$H NMR (CD$_3$OD 400 MHz) δ 7.60 (d, J=8.4H, 2H), 7.49 (d, J=8.8 Hz, 2H), 7.08 (m, 1H), 6.45 (m, 1H), 5.14 (dd, J=12.4, 2.4 Hz, 1H), 4.43 (d, J=12.4 Hz, 1H), 3.87 (dd, J=4.0, 2.0 Hz, 1H), 3.31 (m, 2H), 3.0-3.13 (m, 4H), 2.52 (m, 2H), 2.40 (m, 1H), 2.25 9m, 1H), 2.0 (m, 1H), 1.33 (m, 6H). MS: Calcd. for $C_{24}H_{29}ClF_2NO_7S_2$ (MH$^+$), 564.1. found 5643. Retention time: 3.29/7.5 min.

24c

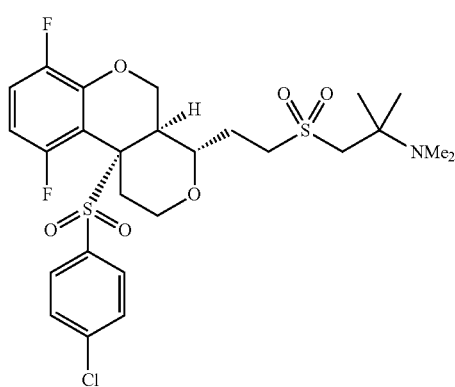

A solution of 0.07 g (0.12 mmol) of compound 24b and 0.15 g (excess) of MeI in 4 mL of acetonitrile was left at room temperature for 5 h. It was concentrated; the residue was purified by preparative TLC eluting with 8% MeOH in CH$_2$Cl$_2$ plus 1% NH$_4$OH to give 0.012 g of compound 24c. $^1$H NMR (CD$_3$OD 400 MHz) δ 7.62 (d, J=8.4H, 2H), 7.49 (d, J=8.4 Hz, 2H), 7.10 (m, 1H), 6.46 (m, 1H), 5.14 (dd, J=12.4, 2.4 Hz, 1H), 4.45 (d, J=12.4 Hz, 1H), 3.87 (d, J=12.4 Hz, 1H), 3.30 (m, 2H), 3.10 (m, 4H), 2.55 (m, 2H), 2.40 (m, 1H), 2.25 (m, 1H), 2.23 9s, 6H), 2.0 (m, 1H), 1.33 (m, 6H). MS: Calcd. for $C_{26}H_{33}ClF_2NO_6S_2$ (MH$^+$), 592.1; found 592.3. Retention time: 2.41/5.5 min.

Scheme 10

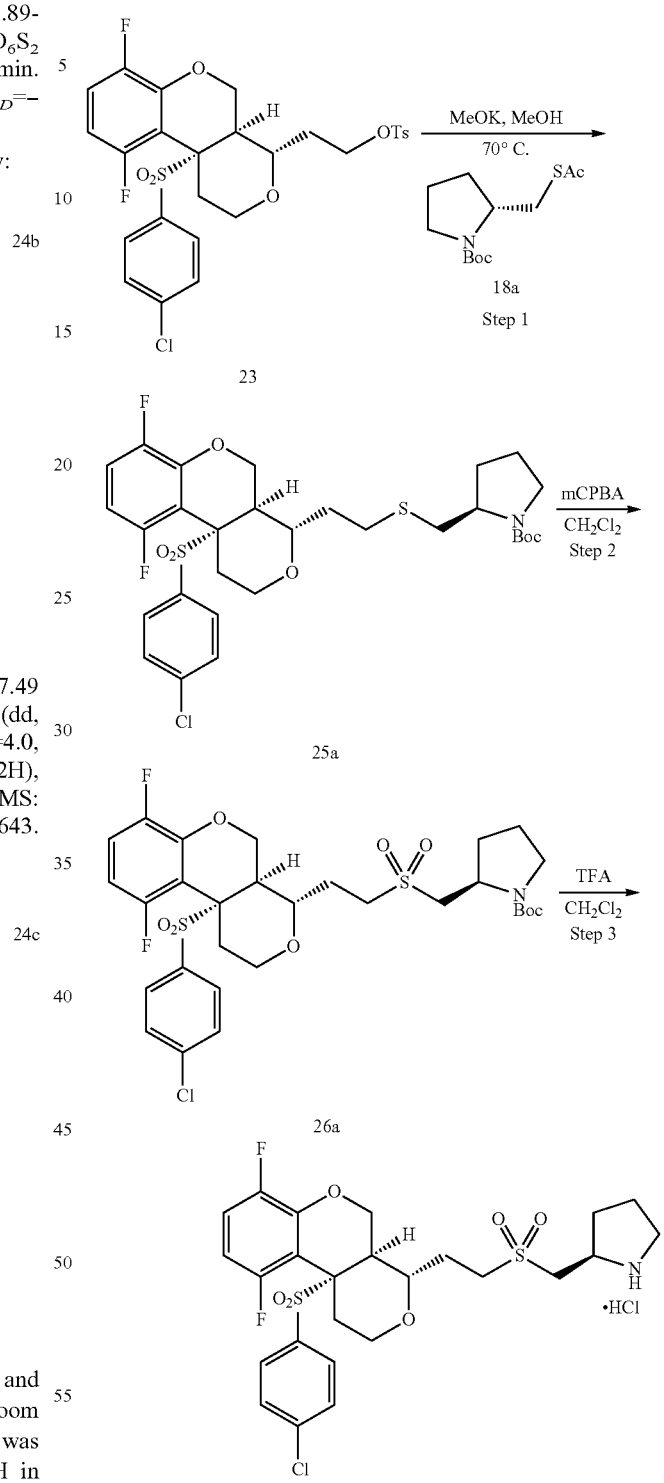

Step 1

A mixture of 0.124 g (0.48 mmol) of compound 18a and 0.067 g (0.96 mmol) of potassium methoxide in 5 mL of methanol was stirred at room temperature for 1 h. After this time, a slurry of 0.288 g (0.48 mmol) of compound 23 in 20 mL of methanol was added and the reaction mixture was heated at 70° C. for 3 h. The reaction mixture was cooled to room temperature, concentrated under reduced pressure, and then partitioned between 50 mL of saturated aqueous NH$_4$Cl and 50 mL of methylene chloride. The aqueous layer was extracted with three 15 mL portions of methylene chloride. The combined organics were dried over anhydrous MgSO$_4$, filtered, and concentrated under reduced pressure. The resulting residue was purified by column chromatography (silica, 0-40% EtOAc/heptane) to afford 0.18 g (58%) of 25a as a white solid: MS: Calcd. for C$_{30}$H$_{36}$ClF$_2$NNaO$_6$S$_2$ (MNa$^+$), m/z=666.1. found 666.3. Retention time: 4.01 min.

The following compounds were prepared analogously:

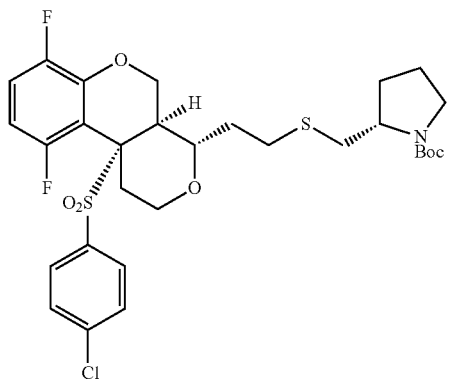

25b

MS: Calcd. for C$_{30}$H$_{36}$ClF$_2$NNaO$_6$S$_2$ (MNa$^+$), m/z=666.1. found 666.3. Retention time: 2.90 min.

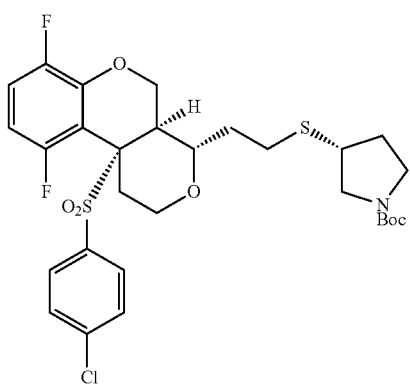

25c

MS: Calcd. for C$_{29}$H$_{35}$ClF$_2$NO$_6$S$_2$ (MH$^+$), m/z=630.2. found 630.3. Retention time: 2.62 min.

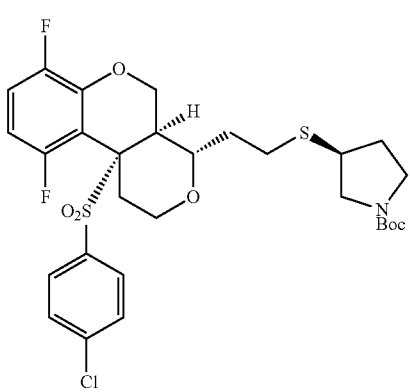

25d

MS: Calcd. for C$_{29}$H$_{35}$ClF$_2$NO$_6$S$_2$ (MH$^+$), m/z=630.2. found 630.3. Retention time: 2.62 min.

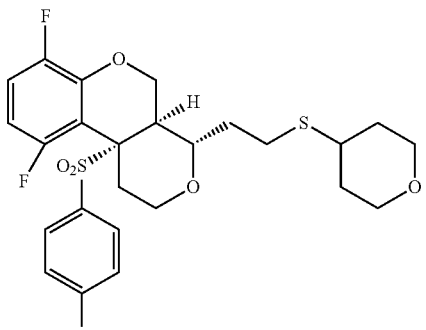

25e

MS: Calcd. for C$_{25}$H$_{27}$ClF$_2$NaO$_5$S$_2$ (MNa$^+$), m/z=567.1. found 57.1. Retention time: 3.43 min.

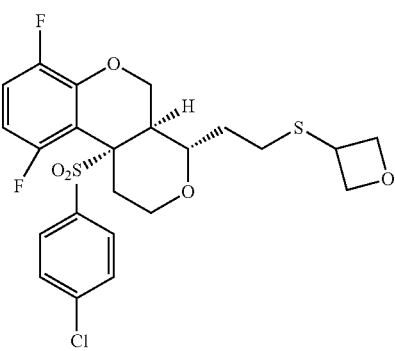

25f

MS: Calcd. for C$_{23}$H$_{25}$ClF$_2$O$_6$S$_2$ (MH$_2$O$^+$), m/z=534.1. found 534.3. Retention time: 2.30 min.

Step 2

To a solution of 0.302 g (0.469 mmol) of compound 25a in 10 mL of methylene chloride was added 0.728 (4.22 mmol) of 3-chloroperbenzoic acid (mCPBA) and the mixture was stirred at room temperature for 3 h. After this time, the reaction was quenched with 20 mL of saturated aqueous NaHCO$_3$. The layers were separated and the aqueous layer was extracted with three 15 mL portions of methylene chloride. The combined organics were dried over anhydrous MgSO$_4$, filtered, and concentrated under reduced pressure. The resulting residue was purified by column chromatography (silica, 0-15% methanol/methylene chloride) to afford 0.29 g (91%) of 26a as a clear oil: MS: Calcd. for C$_{30}$H$_{36}$ClF$_2$NNaO$_8$S$_2$(MNa$^+$), m/z=698.1. found 698.0. Retention time: 2.54 min.

The following compounds were prepared analogously:

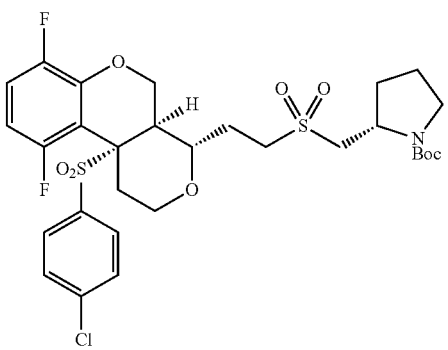

26b

MS: Calcd. for $C_{30}H_{36}ClF_2NNaO_8S_2$ (MNa⁺), m/z=698.1. found 698.3. Retention time: 2.61 min.

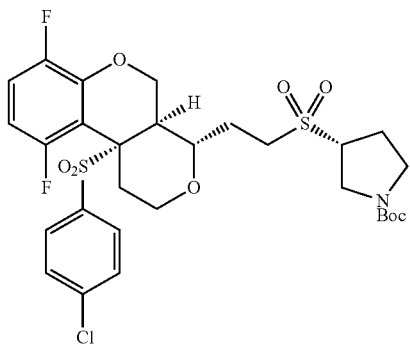

26e

¹H NMR (CDCl₃ 500 MHz) δ 7.64 (d, J=14.5 Hz, 2H), 7.51 (d, J=15.0 Hz, 2H), 7.11 (m, 1H), 6.48 (m, 1H), 5.18 (m, 1H), 4.45 (m, 1H), 3.89 (m, 1H), 3.73 (m, 2H), 3.62 (m, 2H), 3.47 (m, 2H), 3.10 (m, 2H), 2.94 (m, 1H), 2.33 (m, 6H), 2.04 (m, 1H), 1.46 (s, 9H). MS: Calcd. for $C_{29}H_{36}ClF_2NO_9S_2$ (MH₂O⁺), m/z=679.2. found 679.3. Retention time: 2.34 min.

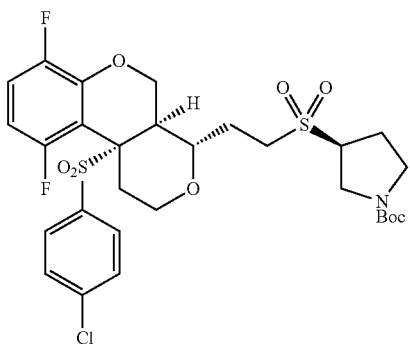

26d

¹H NMR (CDCl₃ 500 MHz) δ 7.63 (d, J=8.5 Hz, 2H), 7.51 (d, J=9.0 Hz, 2H), 7.11 (m, 1H), 6.48 (m, 1H), 5.18 (m, 1H), 4.45 (d, J=12.2 Hz, 1H), 3.89 (m, 1H), 3.75 (m, 2H), 3.61 (m, 2H), 3.42 (m, 2H), 3.18 (m, 2H), 2.95 (m, 1H), 2.55 (m, 2H), 2.30 (m, 4H), 2.05 (m, 1H), 1.46 (s, 9H). MS: Calcd. for $C_{29}H_{36}ClF_2NO_9S_2$ (MH₂O⁺), m/z=679.2. found 679.3. Retention time: 2.32 min.

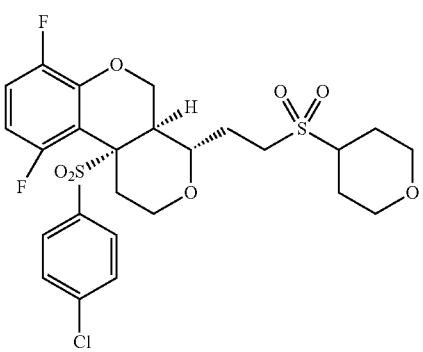

26e

¹H NMR (CDCl₃ 500 MHz) δ 7.63 (d, J=8.3 Hz, 2H), 7.51 (d, J=8.2 Hz, 2H), 7.11 (ddd, J=9.2, 4.6, 4.6 Hz, 1H), 6.47 (m, 1H), 5.17 (dd, J=12.7, 2.0 Hz, 1H), 4.46 (d, J=12.7 Hz, 1H), 4.11-4.13 (m, 2H), 3.88-3.91 (m, 1H), 3.33-3.42 (m, 3H), 3.04-3.21 (m, 3H), 2.90 (ddd, J=11.6, 4.9, 4.9 Hz, 1H), 2.27-2.58 (m, 4H), 1.88-2.08 (m, 5H). MS: Calcd. for $C_{25}H_{27}ClF_2NaO_7S_2$ (MNa⁺), m/z=599.1. found 599.1. Retention time: 3.00 min. HPLC (Method 2) 97.8% (AUC), $t_R$=15.47 min. $[α]^{25}_D$=−143.5° (c 0.23, MeOH).

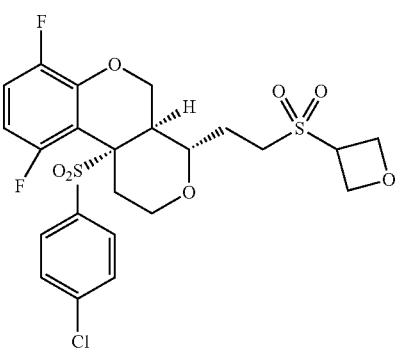

26f

¹H NMR (CDCl₃ 500 MHz) δ 7.63 (d, J=9.0 Hz, 2H), 7.51 (d, J=8.5 Hz, 2H), 7.10 (m, 1H), 6.47 (m, 1H), 5.18 (dd, J=13.0, 2.5 Hz, 1H), 4.97 (dd, J=14.0, 7.5 Hz, 2H), 4.89 (dd, J=15.5, 8.0 Hz, 2H), 4.40 (m, 2H), 3.89 (m, 1H), 3.33 (m, 1H), 3.15 (m, 2H), 2.95 (m, 1H), 2.56 (m, 2H), 2.43 (m, 1H), 2.30 (m, 1H), 2.01 (m, 1H). MS: Calcd. for $C_{23}H_{25}ClF_2O_8S_2$ (MH₂O⁺), m/z=566.1. found 566.2. Retention time: 2.13 min. HPLC: >99% (AUC), $t_R$=14.85 min.

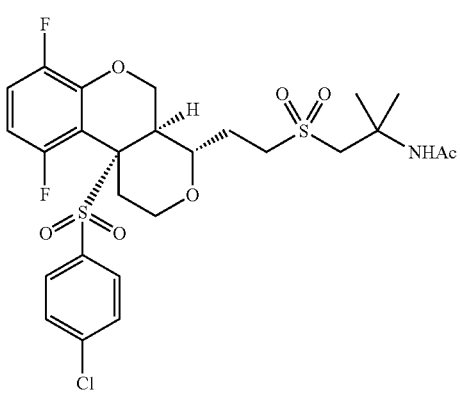

26g

¹H NMR (CD₃OD 400 MHz) δ 7.62 (d, J=8.4H, 2H), 7.50 (d, J=8.8 Hz, 2H), 7.08 (m, 1H), 6.44 (m, 1H), 5.63 (br, 1H), 5.14 (dd, J=12.8, 2.8 Hz, 1H), 4.44 (d, J=12.8 Hz, 1H), 3.86 (m, 1H), 3.58 (AB, J=14 Hz, 2H), 3.30 (m, 1H), 3.10-3.20 (m, 2H), 2.93 (m, 1H), 2.52 (t, J=12.8 Hz, 2H), 2.20-2.40 (m, 2H), 2.0 (m, 1H), 1.95 (s, 3H), 1.56 (s, 6H). MS: Calcd, for $C_{26}H_{31}ClF_2NO_7S_2$ (MH⁺), 606.1. found 606.3. Retention time: 4.32/7.5 min.

26h

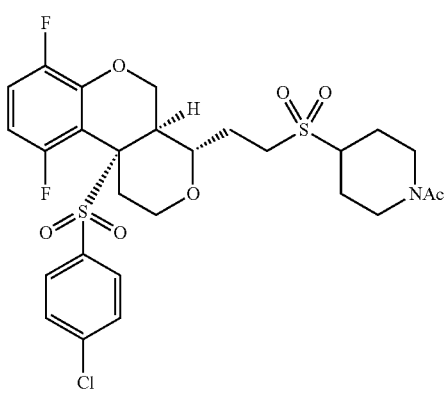

¹H NMR (CD₃OD 400 MHz) δ 7.61 (d, J=11.2H, 2H), 7.50 (d, J=11.2 Hz, 2H), 7.09 (m, 1H), 6.46 (m, 1H), 5.14 (dd, J=12.8, 2.4 Hz, 1H), 4.78 (m, 1H), 3.80-4.0 (m, 2H), 3.33 (m, 1H), 3.0-3.20 (m, 3H), 2.90 (m, 1H), 2.40-2.60 (m, 3H), 2.30 (m, 1H), 2.0-2.20 (m, 7H). MS: Calcd. for $C_{27}H_{31}ClF_2NO_7S_2$ (MH⁺), 618.1. found 618.3. Retention time: 4.10/7.5 min.

26i

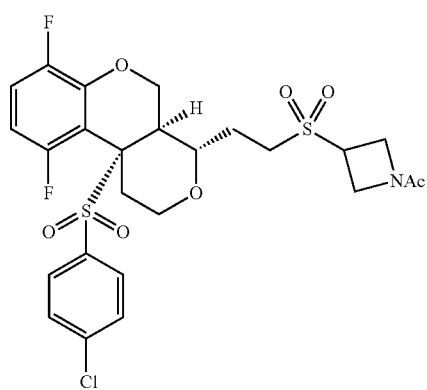

¹H NMR (CD₃OD 400 MHz) δ 7.61 (d, J=8.4H, 2H), 7.49 (d, J=8.4 Hz, 2H), 7.10 (m, 1H), 6.48 (m, 1H), 5.16 (dd, J=12.8, 2.4 Hz, 1H), 4.20-4.50 (m, 5H), 3.90 (m, 2H), 3.38 (m, 1H), 3.20 (m, 2H), 2.95 (m, 1H), 2.58 (m, 2H), 2.42 (m, 1H), 2.30 (m, 1H), 2.0 (m, 1H), 1.87 (s, 3H). MS: Calcd. for $C_{25}H_{27}ClF_2NO_7S_2$ (MH⁺), 590.1. found 590.3. Retention time: 4.79/9.0 min.

Step 3

To a solution of 0.29 g (0.43 mmol) of compound 26a in methylene chloride (4 mL) was added trifluoroacetic acid (0.4 mL) and the mixture was stirred at room temperature for 30 min. After this time, saturated aqueous NaHCO₃ was added slowly and the layers were separated. The aqueous layer was extracted with three 15 mL portions of methylene chloride. The combined organics were dried over anhydrous MgSO₄, filtered, and concentrated under reduced pressure. The residue was purified by preparative HPLC (Method 1) and then lyophilized (CH₃CN/H₂O) to afford 0.028 g (11%) of 27a as a white solid: ¹H NMR (DMSO-d₆ 300 MHz) δ 9.00 (br, 2H), 7.72-7.78 (m, 4H), 7.39-7.47 (m, 1H), 6.72-6.81 (m, 1H), 4.92-4.96 (m, 1H), 4.52-4.61 (m, 1H), 3.82-3.97 (m, 2H), 3.72-3.81 (m, 1H), 3.48-3.64 (m, 2H), 3.12-3.28 (m, 4H), 2.96-3.10 (m, 1H), 2.53-2.61 (m, 1H), 2.38-2.47 (m, 1H), 2.10-2.35 (m, 3H), 1.76-2.08 (m, 3H), 1.55-1.73 (m, 1H). MS: Calcd. for $C_{25}H_{29}ClF_2NO_6S_2$ (MH⁺), m/z=576.1. found 576.2. Retention time: 2.41 min. HPLC (Method 2) >99% (AUC), $t_R$=11.56 min. $[\alpha]^{25}_D$=−190.0° (c 0.04, MeOH).

The following compounds were prepared analogously:

27b

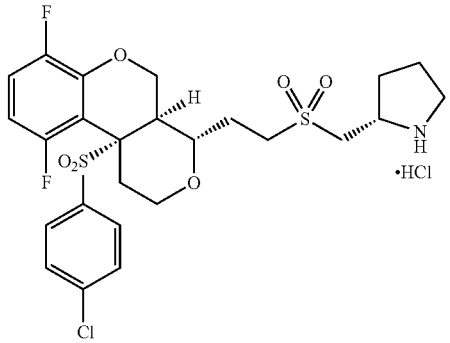

¹H NMR (CDCl₃ 500 MHz) δ 9.66 (br s, 1H), 9.58 (br s, 1H), 7.65 (d, J=8.5 Hz, 2H), 7.51 (d, J=8.6 Hz, 2H), 7.09 (td, J=9.4, 4.6 Hz, 1H), 6.43-6.54 (m, 1H), 5.13 (d, J=11.3 Hz, 1H), 4.70 (d, J=12.7 Hz, 1H), 4.35 (d, J=12.7 Hz, 1H), 4.21 (s, 1H), 3.89 (d, J=11.4 Hz, 1H), 3.28-3.57 (m, 5H), 3.09-3.24 (m, 2H), 2.49-2.68 (m, 3H), 2.39 (s, 1H), 2.28 (t, J=11.8 Hz, 1H), 1.99-2.21 (m, 3H), 1.88-1.99 (m, 1H). MS: Calcd. for $C_{25}H_{29}ClF_2NO_6S_2$ (MH⁺), m/z=576.1. found 576.0. HPLC (Method 2) 97.6% (AUC), $t_R$=11.64 min. $[\alpha]^{20}_D$=−182.0° (c 0.12, chloroform).

27c

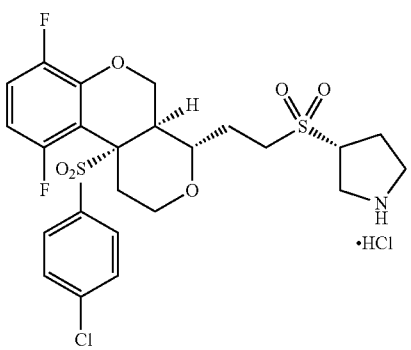

¹H NMR (DMSO-d₆ 500 MHz) δ 9.32 (br s, 1H), 9.18 (br s, 1H), 7.74 (m, 4H), 7.43 (m, 1H), 6.76 (m, 1H), 4.93 (m, 1H), 4.56 (d, J=13.0 Hz, 1H), 4.13 (m, 1H), 3.92 (m, 1H), 3.57 (m, 1H), 3.47 (m, 1H), 3.28 (m, 3H), 3.24 (m, 2H), 3.03 (t, J=11.5 Hz, 1H), 2.52 (m, 2H), 2.28 (m, 3H), 2.17 (m, 1H), 1.94 (m, 1H). MS: Calcd. for $C_{24}H_{27}ClF_2NO_6S_2$ (MH⁺), m/z=562.1. found 562.1. HPLC >99% (AUC), $t_R$=11.44 min. $[\alpha]^{25}_D$=−125.0° (c 0.039 MeOH).

27d

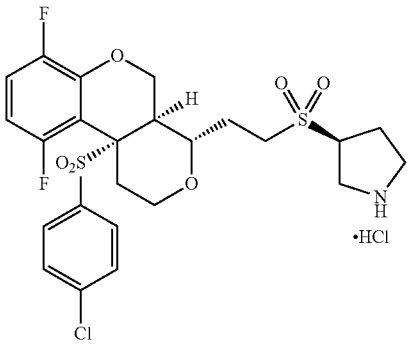

¹H NMR (DMSO-d₆ 500 MHz) δ 9.42 (br s, 1H), 9.21 (br s, 1H), 7.74 (m, 4H), 7.43 (m, 1H), 6.76 (m, 1H), 4.92 (m, 1H), 4.56 (m, 1H), 4.15 (m, 1H), 3.92 (m, 1H), 3.59 (m, 1H), 3.49 (m, 1H), 3.30 (m, 3H), 3.24 (m, 2H), 3.03 (m, 1H), 2.55 (m, 1H), 2.44 (m, 1H), 2.27 (m, 3H), 2.17 (m, 1H), 1.94 (m, 1H). MS: Calcd. for $C_{24}H_{27}ClF_2NO_6S_2$ (MH⁺), m/z=562.1. found 562.3. HPLC >99% (AUC), $t_R$=11.45 min. $[\alpha]^{25}_D$=−123.8° (c 0.068 MeOH).

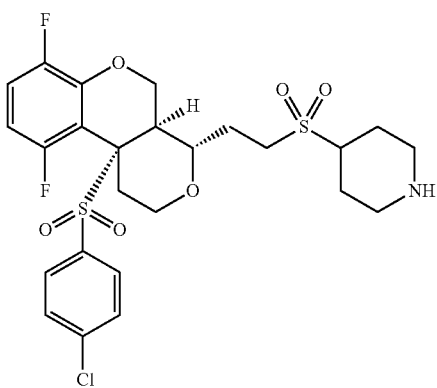

27e

¹H NMR (CD₃OD 400 MHz) δ 7.61 (d, J=8.4H, 2H), 7.49 (d, J=8.4 Hz, 2H), 7.08 (m, 1H), 6.45 (m, 1H), 5.14 (dd, J=12.4, 2.4 Hz, 1H), 4.44 (d, J=12.4 Hz, 1H), 4.43 (s, 1H), 3.88 (m, 1H), 3.10-3.35 9m, 6H), 2.80-3.30 (m, 2H), 2.62 (m, 3H), 2.54 (m, 2H), 2.20-2.44 (m, 5H), 2.03 (m, 4H), 1.77 (m, 2H). MS: Calcd. for $C_{25}H_{29}ClF_2NO_6S_2$ (MH⁺), 576.1. found 576.3. Retention time: 2.21/5.5 min.

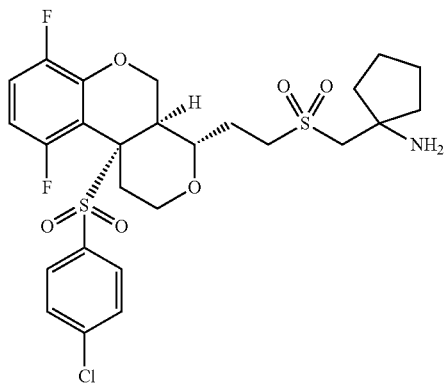

27f

¹H NMR (CD₃OD 400 MHz) δ 7.62 (d, J=8.4H, 2H), 7.50 (d, J=8.4 Hz, 2H), 7.08 (m, 1H), 6.46 (m, 1H), 5.13 (dd, J=12.8, 2.8 Hz, 1H), 4.46 (d, J=12.8 Hz, 1H), 3.86 (m, 1H), 3.44 (br, 2H), 3.38 (m, 4H), 3.0-3.20 (m, 2H), 2.57 (m, 2H), 2.40 (m, 1H), 2.30 (m, 1H), 2.0 (m, 1H), 1.60-1.90 (m, 8H). MS: Calcd. for $C_{26}H_{31}ClF_2NO_6S_2$ (MH⁺), 590.1. found 590.3. Retention time: 2.40/5.5 min.

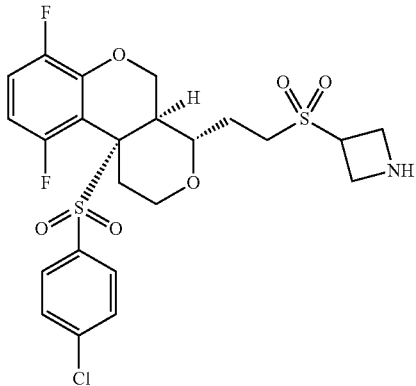

27g

A solution of 0.030 g (0.05 mmol) of compound 26i and 0.56 g (10 mmol) of KOH in 10 mL of EtOH and 3 mL of H₂O was stirred at reflux for 1 h. It was diluted with 20 mL of water, extracted with two 25 mL portions of dichloromethane. The combined organic extracts were concentrated; the residue was purified by chromatography eluting with 1% to 5% MeOH in CH₂Cl₂ plus 1% NH₄OH to give compound 27g. ¹H NMR (CD₃OD 400 MHz) δ 7.61 (d, J=8.4H, 2H), 7.50 (d, J=8.4 Hz, 2H), 7.08 (m, 1H), 6.45 (m, 1H), 5.15 (dd, J=12.8, 2.0 Hz, 1H), 4.42 (d, J=12.8 Hz, 1H), 4.10 (m, 3H), 3.80 (m, 1H), 2.54 (m, 2H), 2.40 (m, 1H), 2.28 (m, 1H), 2.0 (m, 1H). MS: Calcd. for $C_{23}H_2ClF_2NO_6S_2$ (MH⁺), 548.1. found 548.3. Retention time: 3.92/9.0 min.

Scheme 11

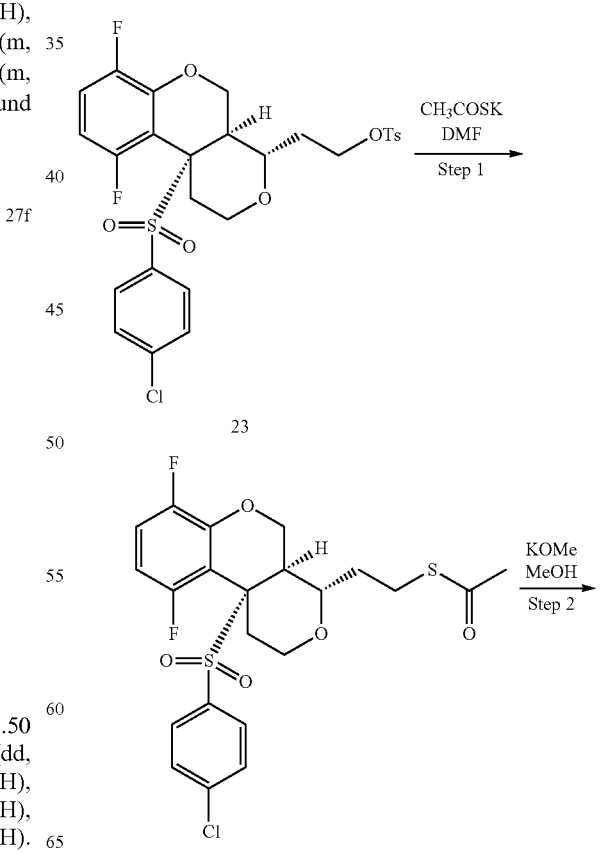

-continued

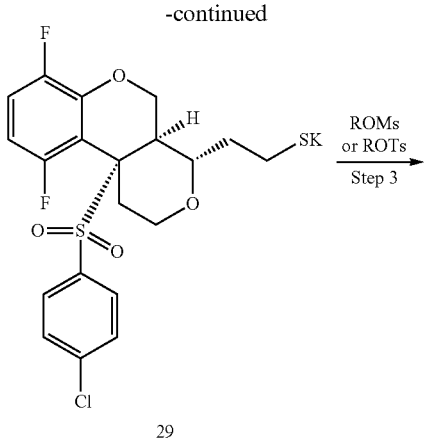

29

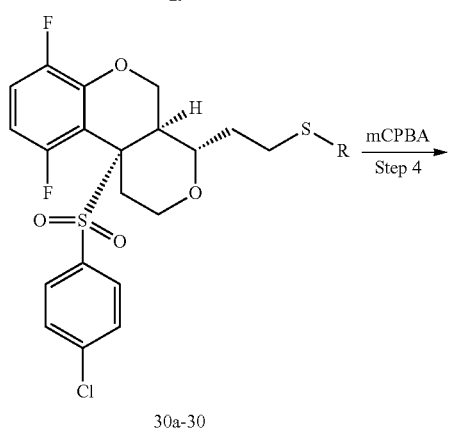

30a-30

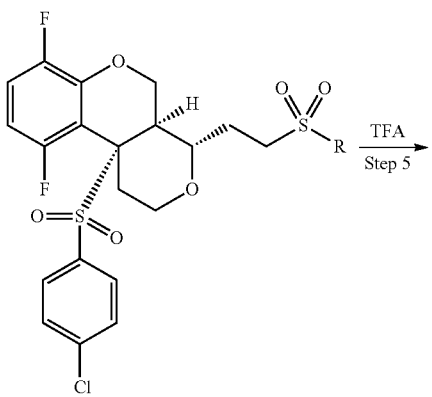

31a-31

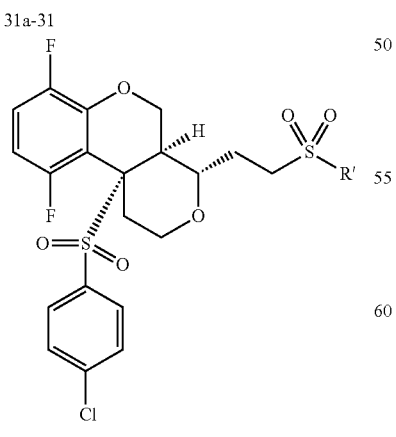

32a-32

Step 1

A mixture of 1.0 g (1.6 mmol) of compound 23 and 0.7 g (6.2 mmol) of potassium thioacetate in 10 mL of DMF was heated at 100° C. for 1.5 h, and cooled to room temperature. It was diluted with 50 mL of water, extracted with two 60 mL portions of ethyl acetate. The combined organic extracts were washed with 20 mL of brine, concentrated. The residue was purified by chromatography eluting with 0% to 50% ethyl acetate in hexanes to give 0.78 g of compound 28. $^1$H NMR (CD$_3$OD 400 MHz) δ 7.62 (d, J=8.8H, 2H), 7.49 (d, J=8.8 Hz, 2H), 7.08 (m, 1H), 6.44 (m, 1H), 5.12 (dd, J=12.8, 2.8 Hz, 1H), 4.43 (d, J=12.8 Hz, 1H), 3.88 (dq, J=10.0, 2.0 Hz, 1H), 3.28 (m, 2H), 3.10 (m, 2H), 2.83 (m, 1H), 2.55 (m, 2H), 2.30 (s, 3H), 2.25 (m, 1H), 2.04 (m, 1H), 1.83 (m, 1H). MS: Calcd. for C$_{22}$H$_{22}$ClF$_2$NO$_5$S$_2$ (MH$^+$), 503.1. found 503.3. Retention time: 5.23/7.5 min.

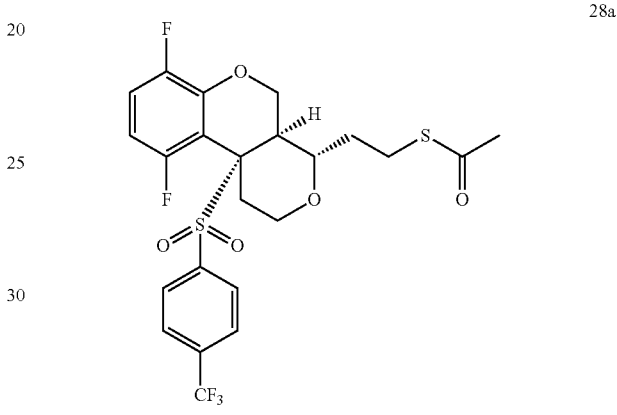

28a

Compound 28a was prepared analgously from the corresponding CF$_3$-substituted analog of 23 (WO 2009/008980). $^1$H NMR (CDCl$_3$ 400 MHz) δ 7.84 (d, J=8.4 Hz, 2H), 7.78 (d, J=8.4 Hz, 2H), 7.10 (m, 1H), 6.45 (m, 1H), 5.12 (dd, J=12.4, 2.4 Hz, 1H), 4.46 (d, J=12.4 Hz, 1H), 3.90 (m, 1H), 3.30 (m, 1H), 3.10 (m, 2H), 2.82 (m, 1H), 2.60 (d, J=10.0 Hz, 1H), 2.50 (m, 1H), 2.34 (s, 3H), 2.30 (m, 1H), 2.08 (m, 1H), 1.85 (m, 1H). LCMS: Calcd. for C$_{23}$H$_{22}$F$_5$O$_5$S$_2$, 537.1 (MH$^+$). found 537.3. Retention time: 5.00/7.5 min.

Step 2-5

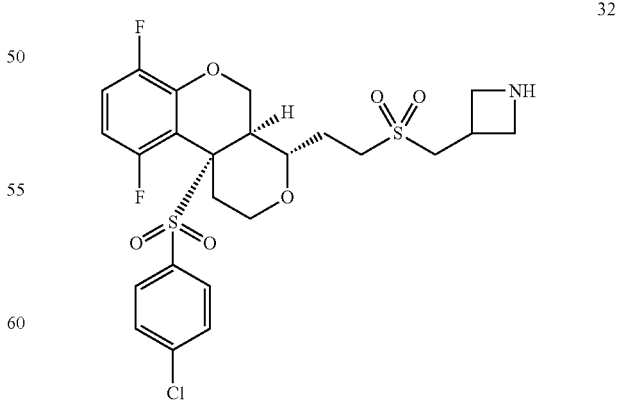

32

To a stirred suspension of 0.12 g (0.24 mmol) of compound 28 in 5 mL of anhydrous MeOH was added 0.035 g (0.5 mmol) of KOMe. After 15 min., 0.080 g (0.3 mmol) of compound was added. The mixture was stirred at 70° C. for 1.5 h, concentrated. The residue was diluted with 20 mL of water, extracted with two 25 mL portions of dichloromethane. The combined organic extracts were concentrated, the residue was dissolved in 20 mL of dichloromethane, and treated with 0.25 g (1.0 mmol) of mCPBA (70%) overnight. It was quenched with 5 mL of 10% $Na_2S_2O_3$, diluted with 20 mL of water and 3 mL of 1 N NaOH. It was extracted with two 30 mL portions of dichloromethane. The combined organic extracts were concentrated. The residue was dissolved in 10 mL of dichloromethane and 5 mL of TFA. After stirring at room temperature for 3 h, it was concentrated. The residue was purified by chromatography eluing with 0% to 10% MeOH in CH2Cl2 plus 1% NH4OH to give 0.063 g of compound 32. $^1$H NMR (CD$_3$OD 400 MHz) δ 7.61 (d, J=8.8H, 2H), 7.50 (d, J=8.8 Hz, 2H), 7.08 (m, 1H), 6.45 (m, 1H), 5.14 (dd, J=12.8, 2.4 Hz, 1H), 4.43 (d, J=12.8 Hz, 1H), 3.85 (m, 2H), 3.54 (m, 2H), 3.45 (s, 2H), 3.30 (m, 3H), 3.10 (m, 2H), 2.90 (m, 1H), 2.56 (m, 2H), 2.40 (m, 1H), 2.26 (m, 1H), 2.10 (br, 1H), 2.0 (m, 1H). MS: Calcd. for $C_{24}H_{27}ClF_2NO_6S_2$ (MH$^+$), 562.1. found 562.3. Retention time: 3.70/7.5 min.

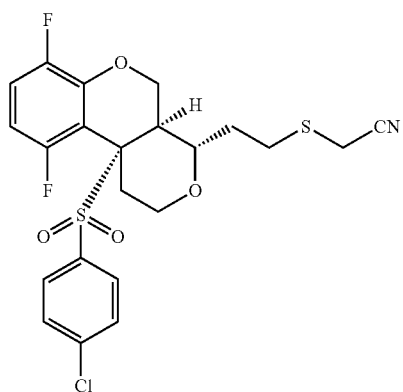

30b $^1$H NMR (CD$_3$OD 400 MHz) δ 7.62 (d, J=8.8H, 2H), 7.50 (d, J=8.8 Hz, 2H), 7.08 (m, 1H), 6.46 (m, 1H), 5.15 (dd, J=12.4, 2.4 Hz, 1H), 4.41 (d, J=12.4 Hz, 1H), 3.87 (m, 1H), 3.36 (m, 4H), 3.29 (s, 2H), 3.15 (m, 1H), 2.95 (m, 1H), 2.78 (m, 1H), 2.55 (m, 2H), 2.30 (m, 1H), 2.18 (m, 1H), 1.95 (m, 1H). MS: Calcd. for $C_{22}H_{21}ClF_2NO_4S_2$ (MH$^+$), 500.1. found 500.3. Retention time: 5.87/9.0 min.

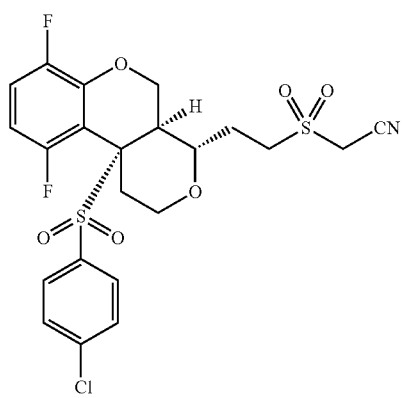

31b $^1$H NMR (CD$_3$OD 400 MHz) δ 7.62 (d, J=8.4H, 2H), 7.51 (d, J=8.8 Hz, 2H), 7.08 (m, 1H), 6.47 (m, 1H), 5.17 (dd, J=12.8, 2.8 Hz, 1H), 4.41 (d, J=12.8 Hz, 1H), 3.98 (m, 2H), 3.90 (m, 1H), 3.52 (m, 1H), 3.33 (m, 2H), 3.18 (m, 1H), 2.58 (m, 3H), 2.30 (m, 1H), 2.10 (m, 1H). MS: Calcd. for $C_{22}H_{21}ClF_2NO_6S_2$ (MH$^+$), 532.1. found 532.3. Retention time: 3.0/5.5 min.

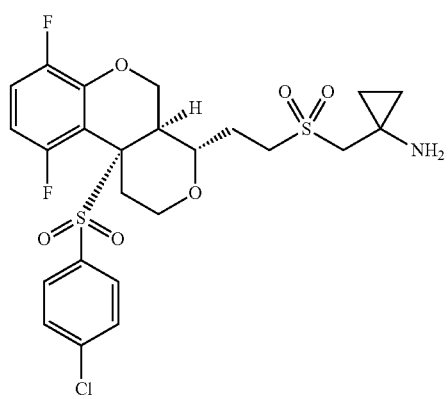

31c $^1$H NMR (CD$_3$OD 400 MHz) δ 7.61 (d, J=8.4H, 2H), 7.49 (d, J=8.4 Hz, 2H), 7.08 (m, 1H), 6.46 (m, 1H), 5.153 (dd, J=12.8, 2.8 Hz, 1H), 4.44 (d, J=12.8 Hz, 1H), 3.86 (m, 1H), 3.30 (m, 4H), 3.0-3.20 (m, 2H), 3.10 (s, 2H), 2.23-2.58 (m, 4H), 2.0 (m, 1H), 0.82 (m, 2H), 0.70 (m, 2H). MS: Calcd. for $C_{24}H_{27}ClF_2NO_6S_2$ (MH$^+$), 562.1. found 562.3. Retention time: 3.10/7.5 min.

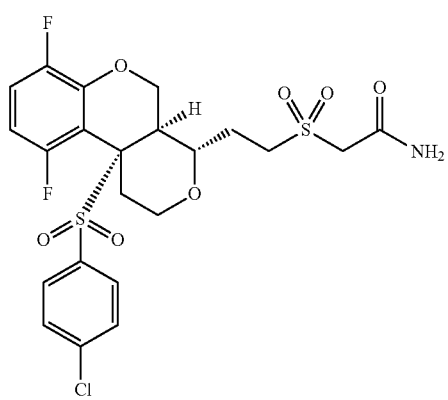

31d $^1$H NMR (CD$_3$OD 400 MHz) δ 7.61 (d, J=8.4H, 2H), 7.49 (d, J=8.4 Hz, 2H), 7.08 (m, 1H), 6.48 (s, 1H), 6.45 (m, 1H), 6.05 (s, 1H), 5.12 (dd, J=12.8, 2.8 Hz, 1H), 4.45 (d, J=12.8 Hz, 1H), 3.92 (s, 2H), 3.88 (m, 1H), 3.45 (m, 1H), 3.38 (m, 1H), 3.20 (m, 1H), 3.10 (m, 1H), 2.4-2.60 (m, 3H), 2.28 (m, 1H), 2.07 (m, 1H). MS: Calcd. for $C_{22}H_{23}ClF_2NO_7S_2$ (MH$^+$), 550.1; found 550.3. Retention time: 3.98/7.5 min.

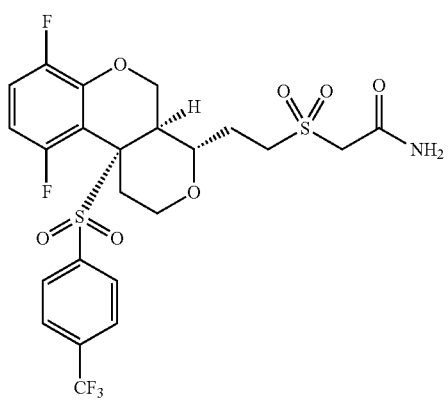

31e

¹H NMR (CDCl₃ 400 MHz) δ 7.84 (d, J=8.4 Hz, 2H), 7.79 (d, J=8.4 Hz, 2H), 7.10 (m, 1H), 6.46 (m, 2H, 1 from CONH2), 5.61 (br s, 1H), 5.18 (dd, J=12.8, 2.4 Hz, 1H), 4.46 (d, J=12.8 Hz, 1H), 3.90 (m, 2H), 3.88 (s, 2H), 3.40 (m, 2H), 3.10-3.22 (m, 2H), 2.60 (d, J=10.4 Hz, 1H), 2.48 (m, 2H), 2.35 (m, 1H), 2.08 (m, 1H). LCMS: Calcd. for C₂₃H₂₃F₅NO₇S₂, 584.1 (MH⁺); found 584.3. Retention time: 4.08/7.5 min.

Scheme 12

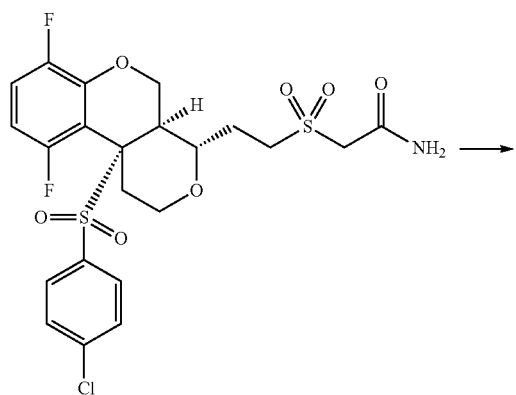

31d

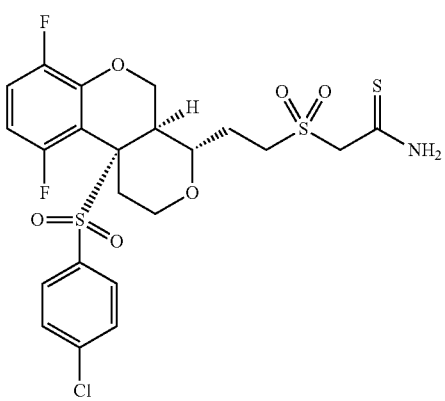

33

A solution of 0.08 g (0.15 mmol) of compound 31d and 0.04 g (0.1 mmol) of Lawesson's reagent in 4 mL of tetrahydrofuran was stirred at reflux for 2 h. It was concentrated; the residue was purified by chromatography eluting with a gradient of 0 to 5% methanol in dichloromethane to give 0.058 g of compound 33: ¹H NMR (CDCl₃, 400 MHz) δ 7.89 (br s, 1H), 7.62 (d, J=8.8 Hz, 2H), 7.60 (br s, 1H), 7.50 (d, J=8.8 Hz, 2H), 7.10 (m, 1H), 6.45 (m, 1H), 5.16 (dd, J=12.8, 2.4 Hz, 1H), 4.44 (d, J=12.8 Hz, 1H), 4.31 (AB q, J=18.8 Hz, 2H), 3.90 (m, 1H), 3.40 (m, 2H), 3.20 (m, 2H), 2.50 (m, 3H), 2.30 (m, 1H), 2.10 (m, 1H). LCMS: Calcd. for C₂₂H₂₃ClF₂NO₆S₃, 566.0 (MH⁺). found 566.3. Retention time: 4.22/7.5 min.

Scheme 13

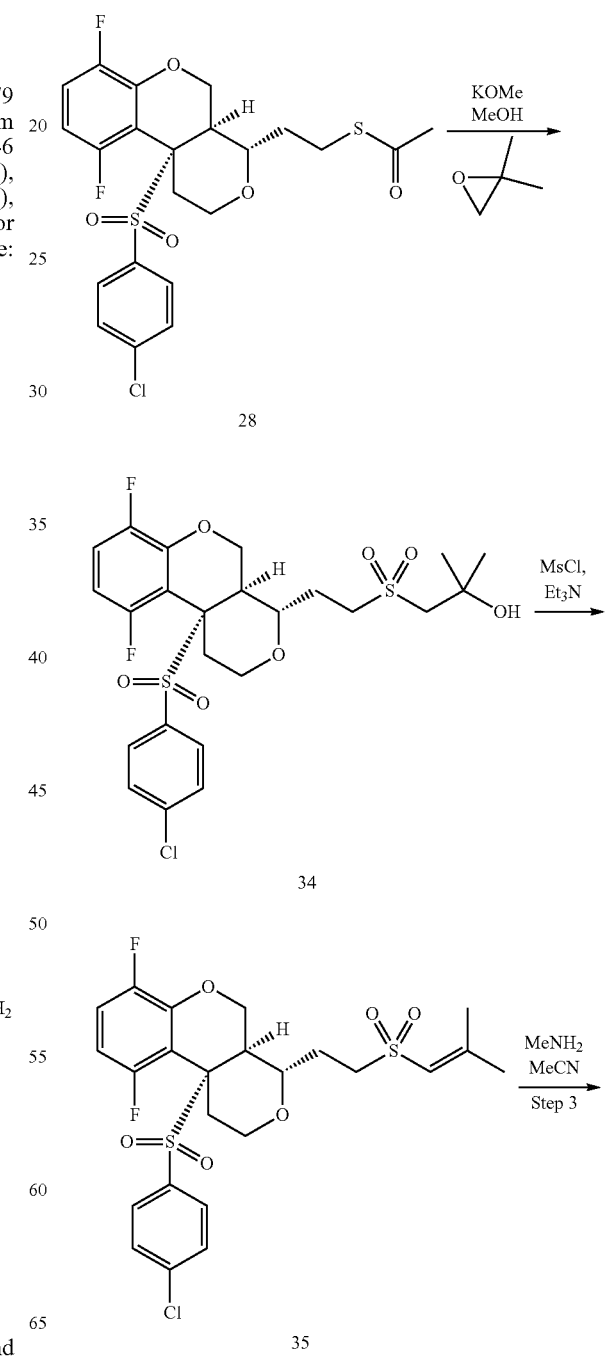

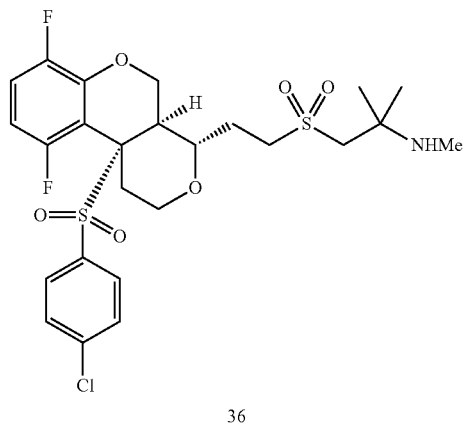 [SMILES: CNC(C)(C)CS(=O)(=O)CC[C@@H]1OCC[C@@]2(S(=O)(=O)c3ccc(Cl)cc3)c3c(F)ccc(F)c3OC[C@@H]12]

36

Step 1

Compound 34 was prepared analogously to Scheme 11, steps 2 and 3, using 2,2-dimethyloxirane as an electrophile. $^1$H NMR (CD$_3$OD 400 MHz) δ 7.62 (d, J=8.8H, 2H), 7.50 (d, J=8.8 Hz, 2H), 7.08 (m, 1H), 6.46 (m, 1H), 5.15 (dd, J=12.8, 2.4 Hz, 1H), 4.44 (d, J=12.8 Hz, 1H), 3.87 (m, 1H), 3.30 (m, 2H), 3.0-3.20 (m, 5H), 2.57 (m, 2H), 2.40 (m, 1H), 2.20 (m, 1H), 2.0 (m, 1H), 1.44 (s, 6H). MS: Calcd. for C$_{24}$H$_{27}$ClF$_2$O$_7$S$_2$ (M$^+$), 564.1. found 564.3. Retention time: 4.23/7.5 min.

Step 2

A solution of 0.25 g (0.44 mmol) of compound 34, 0.20 g (1.7 mmol) of methanesulfonyl chloride, and 0.40 g (4.0 mmol) of triethylamine in 12 mL of dichloromethane was stirred at room temperature for 20 h. It was quenched with 30 mL of saturated sodium bicarbonate, extracted with two 40 mL portions of dichloromethane. The combined organic extracts were concentrated; the residue was purified by chromatography eluting with 0% to 80% ethyl acetate in hexanes to give 0.09 g of compound 35. $^1$H NMR (CD$_3$OD 400 MHz) δ 7.61 (d, J=8.4H, 2H), 7.50 (d, J=8.4 Hz, 2H), 7.08 (m, 1H), 6.45 (m, 1H), 5.99 (m, 1H), 5.13 (dd, J=12.8, 2.8 Hz, 1H), 4.42 (d, J=12.8 Hz, 1H), 3.85 (m, 1H), 3.30 (m, 1H), 2.95-3.20 (m, 3H), 2.55 (m, 2H), 2.20-2.40 (m, 2H), 2.14 (s, 3H), 1.95 (m, 1H), 1.92 (s, 3H). MS: Calcd. for C$_{24}$H$_{26}$ClF$_2$O$_6$S$_2$ (MH$^+$), 547.1. found 547.3. Retention time: 4.67/7.5 min.

Compound 36 was prepared analogously to Scheme 3, step 2.

$^1$H NMR (CD$_3$OD 400 MHz) δ 7.61 (d, J=8.8H, 2H), 7.49 (d, J=8.8 Hz, 2H), 7.07 (m, 1H), 6.44 (m, 1H), 5.14 (dd, J=12.8, 2.8 Hz, 1H), 4.43 (d, J=12.8 Hz, 1H), 3.86 (m, 1H), 3.20-3.37 (m, 2H), 2.95-3.15 (m, 2H), 3.10 (s, 2H), 2.55 (m, 2H), 2.40 (m, 1H), 2.30 (s, 3H), 2.25 (m, 1H), 2.0 (m, 1H), 1.29 (s, 6H). MS: Calcd. for C$_{25}$H$_{31}$ClF$_2$NO$_6$S$_2$ (MH$^+$), 578.1. found 578.3. Retention time: 3.08/7.5 min.

Scheme 14

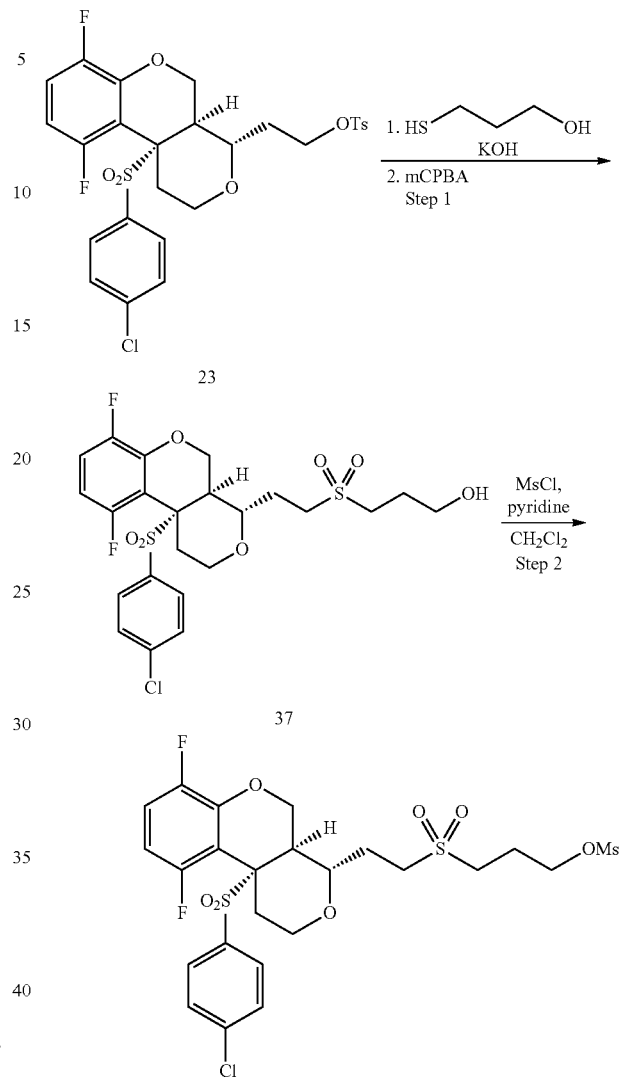

Step 1

A mixture of 1.47 g (2.45 mmol) of compound 23, 0.029 g (0.29 mmol) of 3-mercapto-1-propanol, and 3.7 mL (1M in ethanol, 3.70 mmol) of potassium hydroxide in 41 mL of ethanol was stirred at room temperature for 30 min and then concentrated. The residue was dissolved in 40 mL of water and extracted with three 50 mL portions of methylene chloride. The combined extracts were dried over anhydrous magnesium sulfate, filtered, and concentrated under reduced pressure to give the crude product.

The crude sulfide product was dissolved in 41 mL of methylene chloride and 1.70 g (9.8 mmol) of 3-chloroperoxybenozic acid (mCPBA) was added. The resulting solution was stirred at room temperature for 18 h. After this time, the reaction mixture was diluted with 40 mL of methylene chloride and washed with three 50 mL portions of saturated aqueous sodium bicarbonate, dried over anhydrous magnesium sulfate, filtered, and concentrated under reduced pressure. The residue was purified by column chromatography (silica, 5-100% EtOAc/heptane) to afford 1.05 g (79%) of compound 37 as a white solid: $^1$H NMR (CDCl$_3$ 500 MHz) δ 7.64 (d, J=8.6 Hz, 2H), 7.52 (d, J=8.8 Hz, 2H), 7.11 (td, J=9.4, 4.7 Hz, 1H), 6.44-6.51 (m, 1H), 5.17 (dd, J=12.7, 2.6 Hz, 1H), 4.46 (d, J=12.6 Hz, 1H), 3.90 (ddd, J=11.9, 4.2, 2.3 Hz, 1H), 3.80 (dd, J=11.3, 5.6 Hz, 2H), 3.35 (td, J=9.7, 2.8 Hz, 1H), 3.26 (ddd, J=14.0, 11.2, 4.7 Hz, 1H), 3.10-3.18 (m, 3H), 2.99 (ddd, J=13.9, 11.2, 5.1 Hz, 1H), 2.52-2.59 (m, 2H), 2.41-2.49 (m, 1H), 2.26-2.34 (m, 1H), 2.00-2.14 (m, 3H), 1.71 (t, J=5.3 Hz, 1H). MS: Calcd. for $C_{23}H_{25}ClF_2NaO_7S_2$ (MNa$^+$), m/z=573.1. found 573.3. Retention time: 2.06 min.

Step 2

A mixture of 0.10 g (0.18 mmol) of compound 37, 0.042 g (0.363 mmol) of methanesulfonyl chloride, and 0.043 g (0.54 mmol) of pyridine in 2.6 mL of methylene chloride was stirred at room temperature for 3 h. The reaction was quenched with 10 mL of saturated aqueous ammonium chloride and extracted with three 10 mL portions of methylene chloride. The combined extracts were washed with 40 mL of brine, dried over anhydrous magnesium sulfate, filtered, and concentrated under reduced pressure. The residue was purified by column chromatography (silica, 0-10% methanol/methylene chloride) to afford 0.090 g (79%) of 38 as a white solid: $^1$H NMR (CDCl$_3$ 500 MHz) δ 7.64 (d, J=5.4 Hz, 2H), 7.52 (d, J=8.8 Hz, 2H), 7.11 (tt, J=10.2, 5.1 Hz, 1H), 6.48 (ddd, J=12.0, 12.0, 9.1 Hz, 1H), 5.17 (dd, J=12.7, 2.6 Hz, 1H), 4.46 (d, J=12.4 Hz, 1H), 4.39 (t, J=5.9 Hz, 2H), 3.90 (ddd, J=11.9, 4.1, 2.2 Hz, 1H), 3.35 (td, J=9.7, 2.8 Hz, 1H), 3.27 (ddd, J=14.1, 11.0, 4.7 Hz, 1H), 3.08-3.20 (m, 3H), 2.96-3.07 (m, 4H), 2.51-2.60 (m, 2H), 2.40-2.49 (m, 1H), 2.25-2.36 (m, 3H), 1.98-2.09 (m, 1H). MS Calcd. for $C_{24}H_{29}ClF_2O_{10}S_3$ (MH$_2$O$^+$), m/z=646.1. found 646.3. Retention time: 2.29 min.

Scheme 15

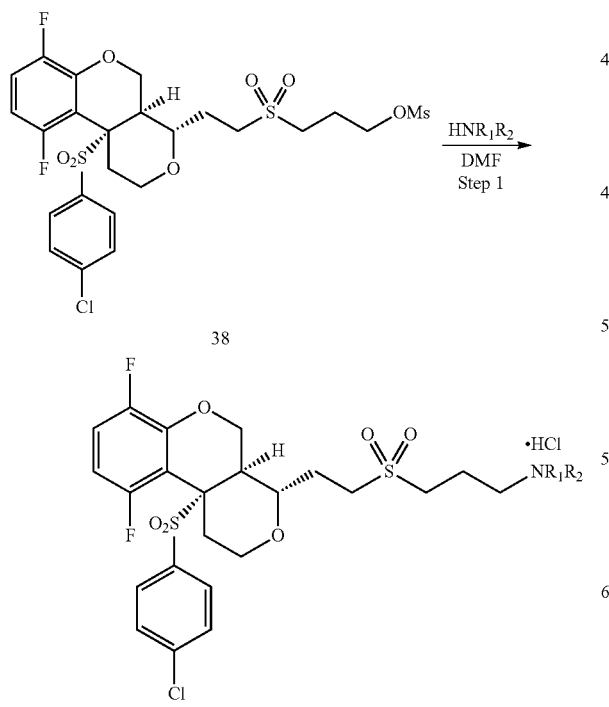

Step 1

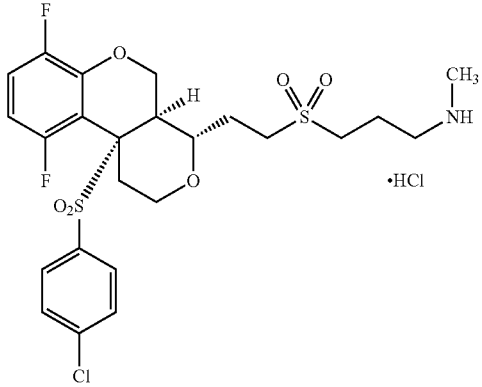

A solution of compound 38 (0.045 g, 0.072 mmol) and methylamine (40% wt. in H$_2$O, 0.031 g, 1.00 mmol) in N,N-dimethylformamide (1 mL) was stirred at 40° C. for 2 h. The mixture was cooled to room temperature and diluted with saturated aqueous sodium bicarbonate (5 mL). The resulting mixture was extracted with methylene chloride (3×10 mL). The combined extracts were washed with brine (40 mL), dried over anhydrous magnesium sulfate, filtered, and concentrated under reduced pressure. The residue was purified by column chromatography (silica, 0-20% methanol/methylene chloride) and then lyophilized (CH$_3$CN/HCl/water) to afford 39a (0.038 g, 88%) as an off-white solid: $^1$H NMR (CDCl$_3$ 500 MHz) δ 9.62 (s, 2H), 7.64 (d, J=8.4 Hz, 2H), 7.51 (d, J=8.5 Hz, 2H), 7.00-7.13 (m, 1H), 6.43-6.52 (m, 1H), 5.14 (d, J=12.1 Hz, 1H), 4.58 (d, J=13.2 Hz, 1H), 3.90 (d, J=12.3 Hz, 1H), 3.43 (s, 2H), 3.29-3.40 (m, 2H), 3.20 (m, 2H), 3.04-3.19 (m, 2H), 2.74 (s, 3H), 2.38-2.63 (m, 5H), 2.30 (s, 1H), 2.05 (d, J=11.8 Hz, 1H). HPLC (Method 2) >99% (AUC), t$_R$=11.29 min. MS Calcd. for $C_{24}H_{29}ClF_2NO_6S_2$ (MH$^+$), m/z=564.1. found 564.0. [α]$^{20}_D$=−119.0° (c 0.10, chloroform).

The following compounds were prepared analogously:

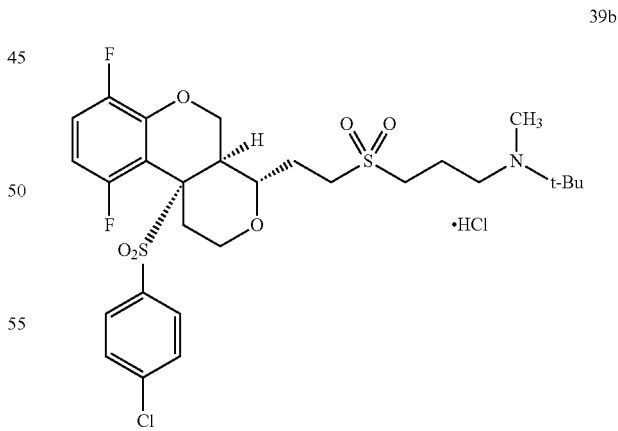

$^1$H NMR (DMSO-d$_6$ 500 MHz) δ 9.50 (s, 1H), 7.75 (m, 4H), 7.42 (td, J=9.9, 4.7 Hz, 1H), 6.70-6.84 (m, 1H), 4.94 (d, J=11.1 Hz, 1H), 4.58 (d, J=12.9 Hz, 1H), 3.92 (d, J=11.8 Hz, 1H), 3.26-3.45 (m, 4H), 3.12-3.25 (m, 2H), 3.03 (t, J=11.5 Hz, 1H), 2.87 (s, 1H), 2.70 (m, 3H), 2.53 (m, 2H), 2.42 (d, J=10.0 Hz, 1H), 2.28 (s, 1H), 2.09-2.22 (m, 2H), 2.08 (s, 1H), 1.92 (d, J=10.2 Hz, 1H), 1.28 (s, 9H). MS: Calcd. for $C_{28}H_{37}ClF_2NO_6S_2$ (MH$^+$), m/z=620.2. found 620.1. HPLC (Method 2) >99% (AUC), $t_R$=11.97 min,

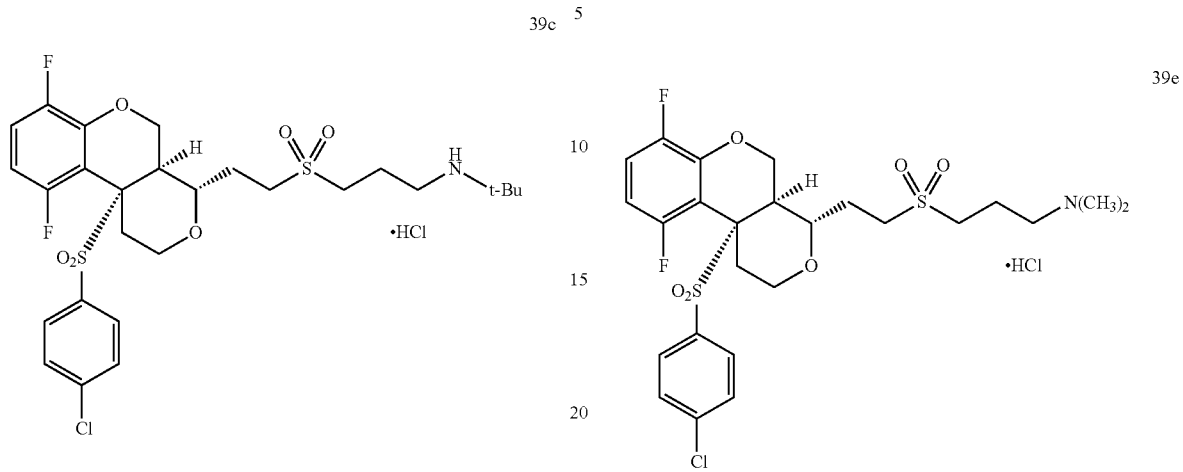

¹H NMR (CDCl₃ 500 MHz) δ 9.37 (s, 2H), 7.64 (d, J=8.5 Hz, 2H), 7.51 (d, J=8.6 Hz, 2H), 7.09 (td, J=9.4, 4.7 Hz, 1H), 6.47 (ddd, J=12.7, 9.1, 3.8 Hz, 1H), 5.14 (dd, J=12.6, 2.0 Hz, 1H), 4.56 (d, J=12.7 Hz, 1H), 3.90 (d, J=11.6 Hz, 1H), 3.30-3.37 (m, 4H), 3.04-3.17 (m, 4H), 2.51-2.64 (m, 4H), 2.47 (t, J=11.4 Hz, 1H), 2.28 (m, 1H), 2.05 (d, J=9.7 Hz, 1H), 1.48 (s, 9H). MS: Calcd. for $C_{27}H_{35}ClF_2NO_6S_2$ (MH$^+$), m/z=606.2. found 606.2. HPLC (Method 2) 98.9% (AUC), $t_R$=12.06 min. $[\alpha]^{25}_D$=−80.0° (c 0.10, chloroform).

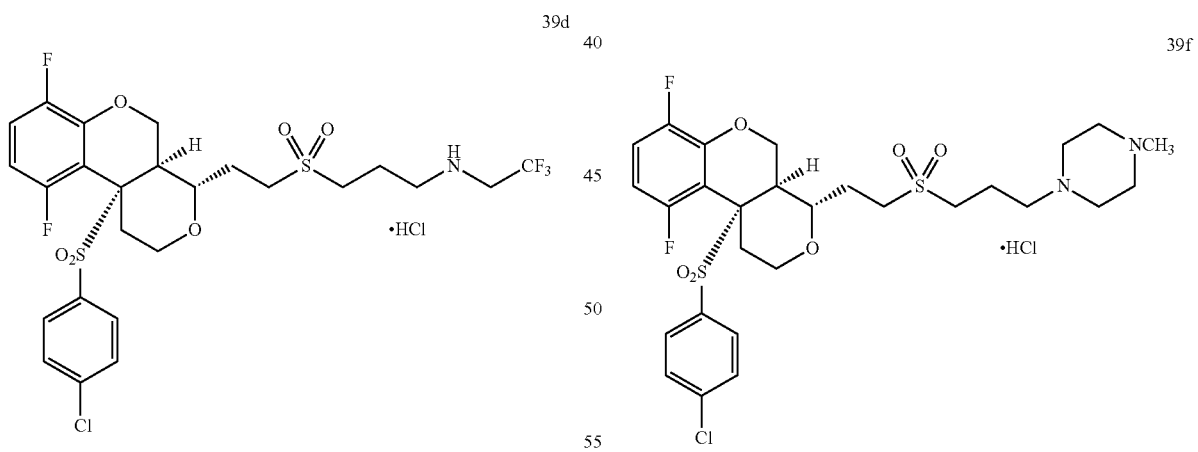

¹H NMR (CDCl₃ 500 MHz) δ 9.96-11.21 (m, 2H), 7.64 (d, J=8.4 Hz, 2H), 7.51 (d, J=8.5 Hz, 2H), 7.10 (td, J=9.3, 4.5 Hz, 1H), 6.42-6.53 (m, 1H), 5.13 (d, J=11.5 Hz, 1H), 4.55 (d, J=12.7 Hz, 1H), 3.90 (d, J=11.1 Hz, 1H), 3.76 (d, J=8.4 Hz, 2H), 3.27-3.51 (m, 6H), 3.04-3.21 (m, 2H), 2.50-2.67 (m, 4H), 2.46 (s, 1H), 2.30 (t, J=11.5 Hz, 1H), 1.98-2.13 (m, 1H). MS: Calcd. for $C_{25}H_{28}ClF_5NO_6S_2$ (MH$^+$), m/z=632.1. found 632.0. HPLC (Method 2) 97.3% (AUC), $t_R$=12.30 min. $[\alpha]^{20}_D$=−150.9° (c 0.055, chloroform).

¹H NMR (CDCl₃ 500 MHz) δ 12.65 (s, 1H), 7.65 (d, J=8.4 Hz, 2H), 7.52 (d, J=8.5 Hz, 2H), 7.11 (td, J=9.2, 4.6 Hz, 1H), 6.42-6.54 (m, 1H), 5.17 (d, J=12.2 Hz, 1H), 4.53 (d, J=12.6 Hz, 1H), 3.91 (d, J=11.7 Hz, 1H), 3.22-3.43 (m, 6H), 3.01-3.21 (m, 2H), 2.84 (s, 6H), 2.40-2.64 (m, 5H), 2.29 (t, J=12.3 Hz, 1H), 1.96-2.13 (m, 1H). MS: Calcd. for $C_{25}H_{31}ClF_2NO_6S_2$ (MH$^+$), m/z=578.1. found 578.0. HPLC (Method 2) >99% (AUC), $t_R$=11.55 min. $[\alpha]^{20}_D$=−139.2° (c 0.13, chloroform).

¹H NMR (DMSO-d₆ 500 MHz) δ 11.69 (s, 1H), 7.67-7.81 (m, 4H), 7.42 (td, J 9.7, 4.7 Hz, 1H), 6.76 (ddd, J=12.9, 9.2, 4.0 Hz, 1H), 4.93 (dd, J=12.8, 2.5 Hz, 1H), 4.59 (d, J=12.6 Hz, 1H), 3.75-4.04 (m, 4H), 3.51-3.76 (m, 4H), 3.38 (s, 1H), 3.01-3.31 (m, 7H), 3.03 (t, J=11.7 Hz, 1H), 2.82 (s, 3H), 2.53 (dd, J=14.0, 5.6 Hz, 1H), 2.42 (d, J=10.1 Hz, 1H), 2.27 (td, J=9.0, 2.8 Hz, 1H), 2.02-2.22 (m, 3H), 1.87-1.98 (m, 1H). MS: Calcd. for $C_{28}H_{36}ClF_2N_2O_6S_2$ (MH$^+$), m/z=633.2.

found 633.0. HPLC (Method 2) 98.5% (AUC), $t_R$=10.57 min. $[\alpha]^{25}_D$=−134.0° (c 0.14, DMSO).

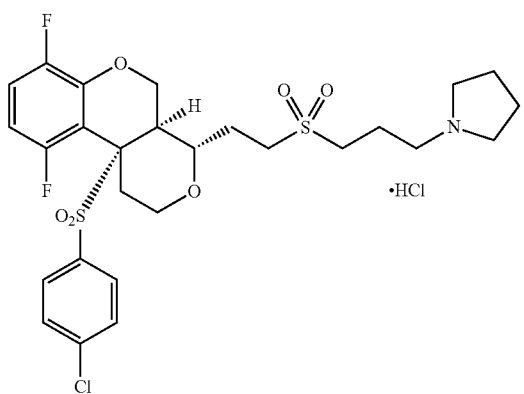

39g $^1$H NMR (CDCl$_3$ 500 MHz) δ 12.46 (s, 1H), 7.65 (d, J=8.6 Hz, 2H), 7.52 (d, J=8.7 Hz, 2H), 7.11 (td, J=9.3, 4.7 Hz, 1H), 6.44-6.52 (m, 1H), 5.17 (dd, J=12.7, 2.4 Hz, 1H), 4.53 (d, J=12.7 Hz, 1H), 3.91 (d, J=10.3 Hz, 1H), 3.83 (s, 2H), 3.25-3.41 (m, 6H), 3.14 (t, J=11.6 Hz, 1H), 3.02-3.11 (m, 1H), 2.86 (s, 2H), 2.39-2.61 (m, 4H), 2.17-2.36 (m, 3H), 1.96-2.15 (m, 4H). MS: Calcd. for C$_{27}$H$_{33}$ClF$_2$NO$_6$S$_2$ (MH$^+$), m/z=604.1. found 604.0. HPLC (Method 2) 98.7% (AUC), $t_R$=11.82 min $[\alpha]^{20}_D$=−95.6° (c 0.12, chloroform).

Scheme 16

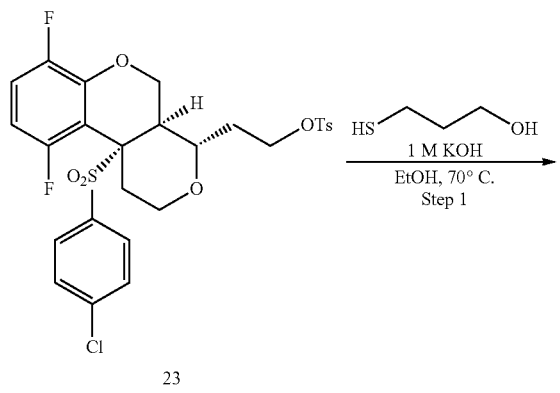

23

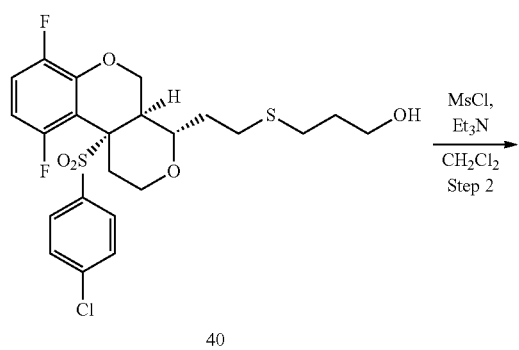

40

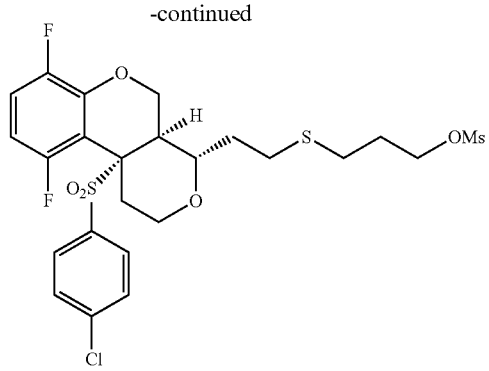

41

Step 1

To a stirred solution of 0.25 g (0.42 mmol) of compound 23 in 10 mL of EtOH was added 0.059 g (0.64 mmol) of 3-thiopropanol and a solution of KOH in EtOH (1 M, 1.0 mL, 1.00 mmol). The resulting solution was heated in a 70° C. oil bath for 2 h, after which time it was cooled to room temperature and then concentrated. The resulting residue was dissolved in 25 mL of methylene chloride and washed with 25 mL of water. The aqueous phase was back-extracted with 25 mL of methylene chloride, the combined organic phases were washed with 25 mL of brine, dried over anhydrous magnesium sulfate, filtered, and concentrated. The residue was purified by column chromatography (silica, 0-50% EtOAc/heptane) to afford 0.188 g (86%) of compound 40 as a white solid: $^1$H NMR (CDCl$_3$ 500 MHz) δ 7.63 (d, J=8.6 Hz, 2H), 7.51 (d, J=8.8 Hz, 2H), 7.11 (ddd, J=9.4, 4.7, 4.7 Hz, 1H), 6.47 (ddd, J=11.9, 9.1, 3.5 Hz, 1H), 5.16 (dd, J=12.6, 2.7 Hz, 1H), 4.45 (d, J=12.5 Hz, 1H), 3.89 (ddd, J=6.5, 5.4, 2.3 Hz, 1H), 3.73 (q, J=5.5 Hz, 2H), 3.37 (ddd, J=10.1, 2.5, 2.5 Hz, 1H), 3.14 (dd, J=11.1, 0.9 Hz, 1H), 2.72 (ddd, J=13.2, 9.0, 4.7 Hz, 1H), 2.51-2.64 (m, 5H), 2.27-2.33 (m, 1H), 2.08-2.15 (m, 1H), 1.80-1.87 (m, 3H), 1.60 (t, J=5.1 Hz, 1H). MS: Calcd. for C$_{23}$H$_{25}$ClF$_2$NaO$_5$S$_2$ (MNa$^+$), m/z=541.1; found 541.4. Retention time: 2.63 min.

Step 2

To a stirred solution of 0.188 g (0.36 mmol) of compound 40 in 40 mL of methylene chloride was added 0.073 g (0.72 mmol) of triethylamine and 0.066 g (0.58 mmol) of methanesulfonyl chloride. After stirring at room temperature for 18 h, the reaction solution was diluted with 25 mL of methylene chloride and washed with 25 mL of water. The aqueous phase was extracted with 25 mL of methylene chloride and the combined organics were washed with 10 mL of saturated aqueous sodium bicarbonate, 10 mL of 1 N hydrochloric acid, and 10 mL of brine, dried over anhydrous magnesium sulfate, filtered, and concentrated. The residue was purified by column chromatography (silica, 0-100% EtOAc/heptane) to afford 0.173 g (80%) of compound 41 as a white foam: $^1$H NMR (CDCl$_3$ 500 MHz) δ 7.63 (d, J=8.6 Hz, 2H), 7.51 (d, J=8.8 Hz, 2H), 7.10 (ddd, J=9.5, 5.0, 5.0 Hz, 1H), 6.47 (ddd, J=12.0, 9.1, 4.0 Hz, 1H), 5.15 (dd, J=12.6, 2.7 Hz, 1H), 4.43 (d, J=12.5 Hz, 1H), 4.32 (t, J=6.0 Hz, 2H), 3.88 (ddd, J=6.5, 4.2, 2.3 Hz, 1H), 3.36 (ddd, J=11.3, 10.0, 2.5 Hz, 1H), 3.14 (t, J=11.3 Hz, 1H), 3.02 (s, 3H), 2.71 (ddd, J=13.2, 9.3, 4.8 Hz, 1H), 2.62-2.65 (m, 5H), 2.27-2.33 (m, 1H), 2.07-2.13 (m, 1H), 1.98-2.04 (m, 2H), 1.80-1.86 (m, 3H). MS: Calcd. for C$_{24}$H$_{27}$ClF$_2$NaO$_7$S$_3$ (MNa$^+$), m/z=619.1; found 619.2. Retention time: 2.86 min.

SCHEME 17

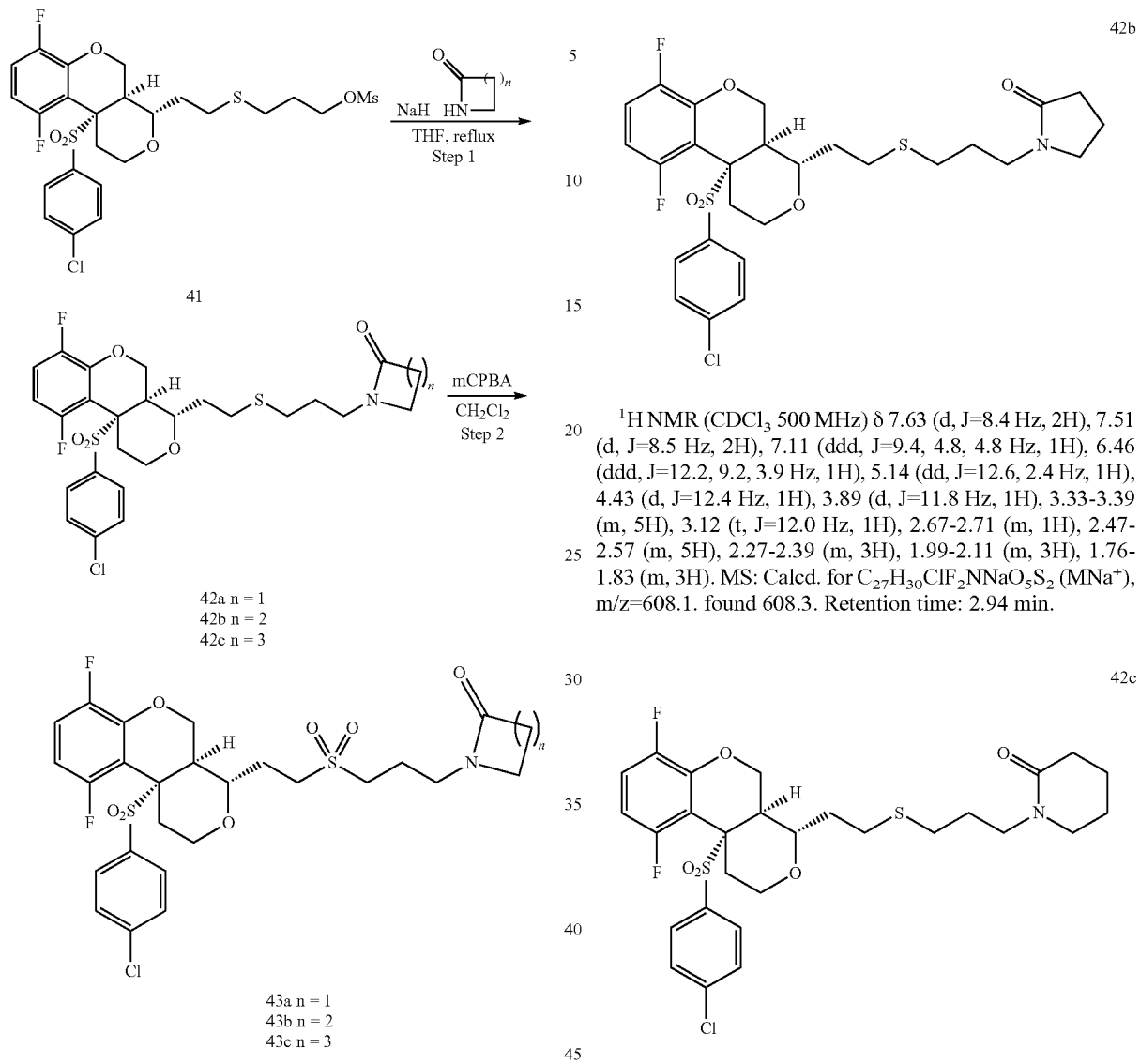

42a n = 1
42b n = 2
42c n = 3

43a n = 1
43b n = 2
43c n = 3

Step 1

To a stirred solution of 0.032 g (0.45 mmol) of 2-azetidinone in 2 mL of THF was added 0.027 g (60% in miniral oil, 0.68 mmol) of sodium hydride at room temperature under nitrogen. After 20 min, a solution of 0.162 g (0.27 mmol) of compound 41 in 3 mL of THF was added and the resulting solution heated at reflux for 18 h. After this time, the reaction mixture was cooled to room temperature and diluted with 15 mL of water. The resulting mixture was extracted with three 15 mL portions of ethyl acetate. The combined organics were washed with 15 mL of brine, dried over anhydrous magnesium sulfate, filtered, and concentrated to afford 0.126 g (82%) of compound 42a as a white solid: $^1$H NMR (CDCl$_3$ 500 MHz) δ 7.63 (d, J=8.6 Hz, 2H), 7.51 (d, J=8.5 Hz, 2H), 7.07-7.12 (m, 1H), 6.44-6.49 (m, 1H), 5.14-5.17 (m, 1H), 4.43 (d, J=12.4 Hz, 1H), 4.12 (q, J=7.2 Hz, 1H), 3.89 (ddd, J=6.3, 4.0, 2.3 Hz, 1H), 3.22-3.38 (m, 3H), 3.14 (t, J=11.5 Hz, 1H), 3.03 (ddd, J=6.0, 4.3, 1.7 Hz, 1H), 2.92 (t, J=4.1 Hz, 1H), 2.50-2.72 (m, 6H), 2.27-2.32 (m, 1H), 2.07-2.13 (m, 1H), 1.99-2.03 (m, 2H), 1.78-1.85 (m, 2H). MS: Calcd. for $C_{26}H_{28}ClF_2NNaO_3S_2$ (MNa$^+$), m/z=594.1. found 594.3. Retention time: 2.94 min.

The following compounds were prepared analogously:

$^1$H NMR (CDCl$_3$ 500 MHz) δ 7.63 (d, J=8.4 Hz, 2H), 7.51 (d, J=8.5 Hz, 2H), 7.11 (ddd, J=9.4, 4.8, 4.8 Hz, 1H), 6.46 (ddd, J=12.2, 9.2, 3.9 Hz, 1H), 5.14 (dd, J=12.6, 2.4 Hz, 1H), 4.43 (d, J=12.4 Hz, 1H), 3.89 (d, J=11.8 Hz, 1H), 3.33-3.39 (m, 5H), 3.12 (t, J=12.0 Hz, 1H), 2.67-2.71 (m, 1H), 2.47-2.57 (m, 5H), 2.27-2.39 (m, 3H), 1.99-2.11 (m, 3H), 1.76-1.83 (m, 3H). MS: Calcd. for $C_{27}H_{30}ClF_2NNaO_5S_2$ (MNa$^+$), m/z=608.1. found 608.3. Retention time: 2.94 min.

MS: Calcd. for $C_{28}H_{33}ClF_2NO_5S_2$ (MH$^+$), m/z=600.2. found 600.3. Retention time: 2.94 min.

Step 2

To a stirred solution of 0.138 g (0.24 mmol) of compound 42a in 2 mL of methylene chloride was added 0.225 g (1.0 mmol) of 3-chloroperbenzoic acid (mCPBA). After stirring at room temperature for 4 h, the reaction mixture was diluted with 20 mL of methylene chloride and washed with 10 mL of saturated aqueous sodium bicarbonate and 10 mL of brine, dried over anhydrous magnesium sulfate, filtered, and concentrated to a yellow solid. Purification by preparative HPLC (Method 1) and then lyophilization (CH$_3$CN/H$_2$O) afforded 0.040 g (28%) of 43a as a white solid: $^1$H NMR (DMSO-d$_6$ 500 MHz) δ 7.72-7.76 (m, 4H), 7.42 (ddd, J=10.1, 4.8, 4.8 Hz, 1H), 6.76 (ddd, J=12.4, 9.2, 3.9 Hz, 1H), 4.91 (dd, J=12.4, 2.5 Hz, 1H), 4.56 (d, J=12.6 Hz, 1H), 3.89-3.92 (m, 1H), 3.01-3.32 (m, 11H), 2.82 (t, J=4.0 Hz, 1H), 2.13-2.63 (m, 5H), 1.82-1.91 (m, 2H). MS: Calcd. for $C_{26}H_{28}ClF_2NNaO_7S_2$ (MNa$^+$), m/z=629.1. found 629.2. HPLC (Method 2) 97.9% (AUC), $t_R$=14.40 min. $[α]^{20}_D$=−137.0° (c 0.10, methylene chloride).

The following compounds were prepared analogously:

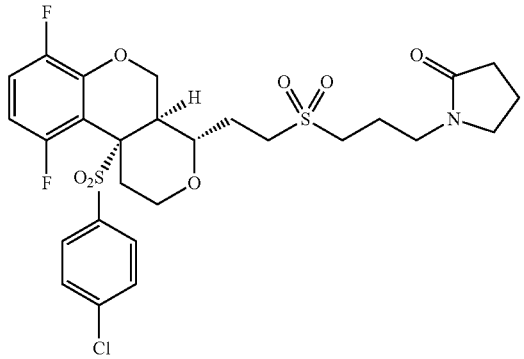
43b $^1$H NMR (CDCl$_3$ 500 MHz) δ 7.64 (d, J=8.4 Hz, 2H), 7.51 (d, J=8.5 Hz, 2H), 7.09-7.13 (m, 1H), 6.45-6.49 (m, 1H), 5.15-5.18 (m, 1H), 4.44 (d, J=12.5 Hz, 1H), 3.89-3.92 (m, 1H), 3.32-3.43 (m, 6H), 2.94-3.25 (m, 4H), 2.27-2.56 (m, 6H), 2.01-2.09 (m, 5H). MS: Calcd. for C$_{27}$H$_{30}$ClF$_2$NNaO$_7$S$_2$ (MNa$^+$), m/z=640.1. found 640.3. Retention time: 2.78 min. HPLC (Method 2) 98.0% (AUC), t$_R$=14.30 min. [α]$^{20}_D$=−112.0° (c 0.17, methylene chloride).

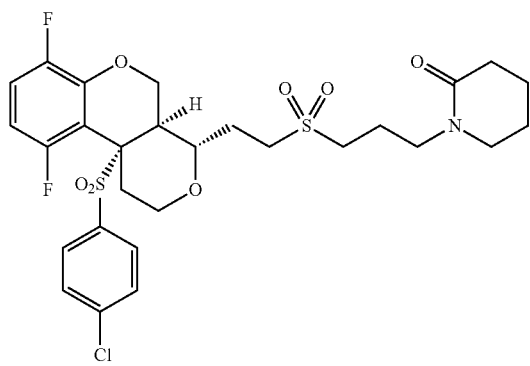
43c $^1$H NMR (DMSO-d$_6$ 500 MHz) δ 7.75 (m, 4H), 7.42 (m, 1H), 6.75 (m, 1H), 4.92 (d, J=12.5 Hz, 1H), 4.56 (d, J=12.5 Hz, 1H), 3.90 (d, J=8.0 Hz, 1H), 3.30 (m, 5H), 3.10 (m, 6H), 2.40 (d, J=10.0 Hz, 1H), 2.19 (m, 4H), 1.85 (m, 3H), 1.69 (m, 4H). MS: Calcd. for C$_{28}$H$_{33}$ClF$_2$NO$_7$S$_2$ (MH$^+$), m/z=632.1. found 632.3. Retention time: 2.75 min. HPLC: 95.3% (AUC), t$_R$=14.52 min. [α]$^{25}_D$=−351.4° (c 0.023, MeOH).

SCHEME 18

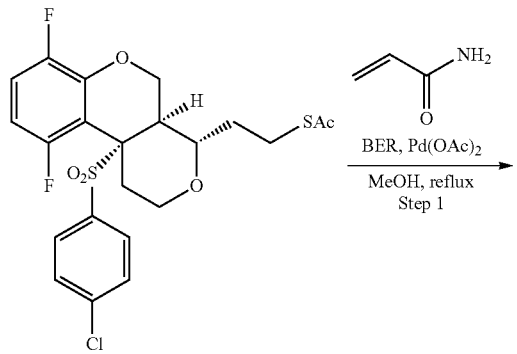
28

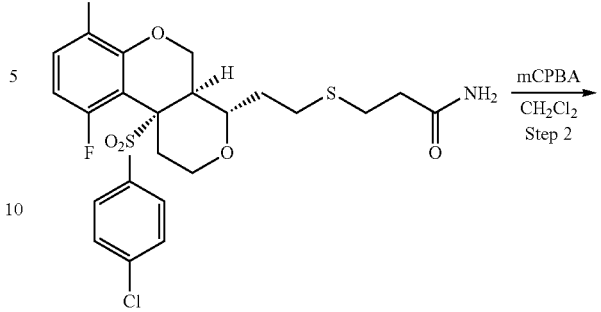
44

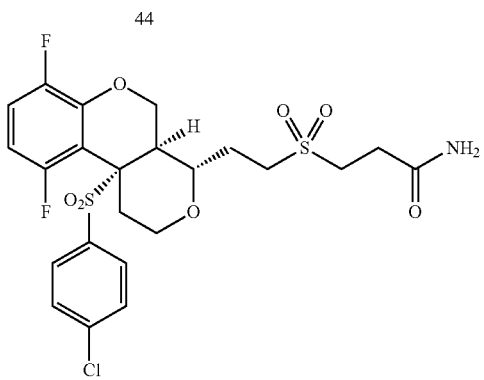
45

Step 1

To a stirred suspension of 0.10 g of borohydride exchange resin (BER) in 5 mL of methanol was added 0.005 g (0.02 mmol) of palladium acetate. The suspension was heated at reflux for 2 h and then a suspension of 0.128 g (0.25 mmol) of compound 28 in 5 mL of MeOH was added, followed by 0.02 g (0.28 mmol) of acrylamide. The resulting suspension was heated at reflux for an additional 1 h, then cooled to room temperature, filtered over Celite, and concentrated to afford 0.112 g (83%) of 44 as a white solid which was carried forward without further purification. $^1$H NMR (CDCl$_3$ 500 MHz) δ 7.63 (d, J=8.5 Hz, 2H), 7.51 (d, J=8.8 Hz, 2H), 7.10 (ddd, J=14.0, 9.3, 4.7 Hz, 1H), 6.47 (ddd, J=12.1, 9.3, 4.0 Hz, 1H), 5.60 (br s, 2H), 5.15 (dd, J=12.5, 2.5 Hz, 1H), 4.45 (d, J=12.4 Hz, 1H), 3.87-3.89 (m, 1H), 3.35-3.40 (m, 1H), 3.14 (t, J=12.0 Hz, 1H), 2.71-2.88 (m, 3H), 2.47-2.62 (m, 5H), 2.27-2.31 (m, 1H), 2.10-2.13 (m, 1H), 1.84 (ddd, J=13.8, 8.8, 4.8 Hz, 1H). MS: Calcd. for C$_{23}$H$_{24}$ClF$_2$NNaO$_5$S$_2$ (MNa$^+$), m/z=554.1. found 554.3. Retention time: 1.94 min.

Step 2

To a solution of 0.112 g (0.21 mmol) of compound 44 in 5 mL of methylene chloride was added 0.125 g (70%, 0.72 mmol) of 3-chloroperbenzoic acid (mCPBA), and the mixture was stirred at room temperature for 1 h. After this time, the reaction was quenched with 20 mL of saturated aqueous NaHCO$_3$. The layers were separated and the aqueous layer was extracted with three 15 mL portions of methylene chloride. The combined organics were dried over anhydrous MgSO$_4$, filtered, and concentrated under reduced pressure. The resulting residue was purified by preparative HPLC (Method 1) and then lyophilized (CH$_3$CN/H$_2$O) to afford 0.055 g (46%) of 45 as a white solid: $^1$H NMR (CDCl$_3$ 500 MHz) δ 7.63 (d, J=6.7 Hz, 2H), 7.51 (d, J=7.3 Hz, 2H), 7.05-7.15 (m, 1H), 6.45-6.55 (m, 1H), 5.76 (br s, 1H), 5.56 (br s, 1H), 5.15 (d, J=12.5 Hz, 1H), 4.46 (d, J=12.2 Hz, 1H), 3.87-3.89 (m, 1H), 3.20-3.36 (m, 4H), 3.03-3.14 (m, 2H), 2.75-2.81 (m, 2H), 2.27-2.61 (m, 4H), 2.10-2.13 (m, 1H). MS: Calcd. for $C_{23}H_{24}ClF_2NNaO_5S_2$ (MNa$^+$), m/z=586.1. found 586.2. Retention time: 1.96 min. HPLC (Method 2) 96.4% (AUC), $t_R$=13.20 min. $[\alpha]^{20}_D$=−111.0° (c 0.46, methylene chloride).

SCHEME 19

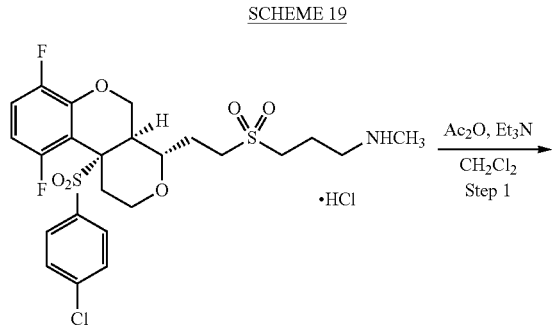

39a

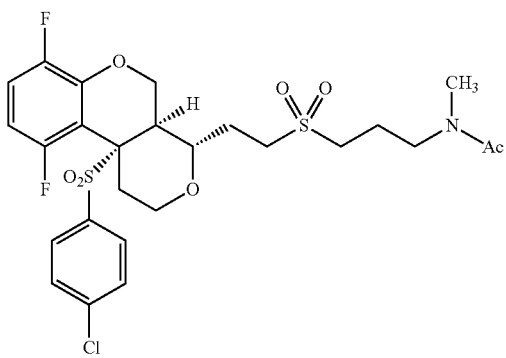

46a

Step 1

A solution of 0.116 g (0.193 mmol) of compound 39a, 0.029 g (0.29 mmol) of acetic anhydride, and 0.039 g (0.39 mmol) of triethylamine in 2 mL of methylene chloride was stirred at room temperature for 18 h. The reaction was quenched with 5 mL of saturated aqueous ammonium chloride and extracted with three 50 mL portions of methylene chloride. The combined extracts were dried over anhydrous magnesium sulfate, filtered, and concentrated under reduced pressure. The residue was purified by column chromatography (silica, 0-60% EtOAc/heptane) and lyophilized (CH$_3$CN/water) to afford 0.071 g (61%) of 46a as an off-white solid: $^1$H NMR (CDCl$_3$ 300 MHz) 5, 7.63 (d, J=7.0 Hz, 2H), 7.52 (d, J=8.8 Hz, 2H), 7.11 (td, J=9.4, 4.8 Hz, 1H), 6.41-6.55 (m, 1H), 5.17 (dd, J=12.6, 2.4 Hz, 1H), 4.45 (d, J=12.6 Hz, 1H), 3.82-3.98 (m, 1H), 3.51 (t, J=6.8 Hz, 2H), 3.34 (t, J=8.4 Hz, 1H), 3.07-3.29 (m, 2H), 2.85-3.06 (m, 5H), 2.55 (d, J=13.4 Hz, 2H), 2.36-2.50 (m, 1H), 2.22-2.36 (m, 1H), 1.94-2.20 (m, 7H). MS: Calcd. for $C_{26}H_{31}ClF_2NO_7S_2$ (MH)$^+$, m/z=606.1. found 606.1. HPLC (Method 2) 98.7% (AUC), $t_R$=14.21 min. $[\alpha]^{25}_D$=−145.0° (c 0.18, chloroform).

The following compounds were prepared analogously:

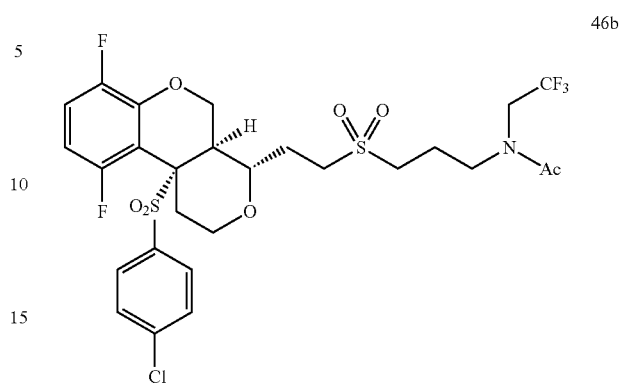

46b

Compound 46b: a mixture of rotamers (1.84:1).

Major rotamer: $^1$H NMR (CDCl$_3$ 500 MHz) δ 7.64 (d, J=8.4 Hz, 2H), 7.52 (d, J=8.7 Hz, 2H), 7.11 (td, J=9.3, 4.6 Hz, 1H), 6.48 (dd, J=14.5, 6.1 Hz, 1H), 5.11-5.26 (m, 1H), 4.45 (d, J=12.6 Hz, 1H), 3.83-3.96 (m, 3H), 3.56-3.66 (m, 2H), 3.30-3.39 (m, 1H), 3.18-3.31 (m, 1H), 3.14 (t, J=12.0 Hz, 1H), 2.91-3.05 (m, 3H), 2.49-2.63 (m, 2H), 2.38-2.49 (m, 1H), 2.23-2.37 (m, 1H), 2.07-2.24 (m, 5H), 1.97-2.07 (m, 1H).

Minor rotamer: $^1$H NMR (CDCl$_3$ 500 MHz) δ 7.64 (d, J=8.4 Hz, 2H), 7.52 (d, J=8.7 Hz, 2H), 7.11 (td, J=9.3, 4.6 Hz, 1H), 6.48 (dd, J=14.5, 6.1 Hz, 1H), 5.11-5.26 (m, 1H), 4.45 (d, J=12.6 Hz, 1H), 4.04 (m, 3H), 3.56-3.66 (m, 2H), 3.30-3.39 (m, 1H), 3.18-3.31 (m, 1H), 3.14 (t, J=12.0 Hz, 1H), 2.91-3.05 (m, 3H), 2.49-2.63 (m, 2H), 2.38-2.49 (m, 1H), 2.23-2.37 (m, 1H), 2.07-2.24 (m, 5H), 1.97-2.07 (m, 1H). MS: Calcd. for $C_{27}H_{29}ClF_5NNaO_7S_2$ (MNa$^+$), m/z=696.1. found 696.2. HPLC (Method 2) >99% (AUC), $t_R$=15.93 min. $[\alpha]^{20}_D$=−119.0° (c 0.11, chloroform).

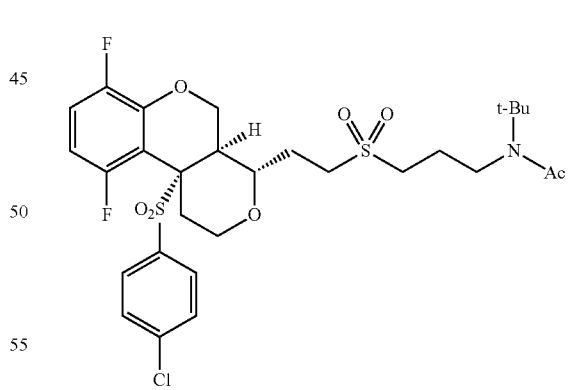

46c $^1$H NMR (CDCl$_3$ 300 MHz) δ 7.64 (d, J=8.7 Hz, 2H), 7.52 (d, J=8.8 Hz, 2H), 7.12 (td, J=9.4, 4.8 Hz, 1H), 6.48 (ddd, J=11.9, 9.1, 4.0 Hz, 1H), 5.18 (dd, J=12.7, 2.6 Hz, 1H), 4.45 (d, J=12.5 Hz, 1H), 3.84-3.97 (m, 1H), 3.41-3.54 (m, 2H), 3.06-3.39 (m, 3H), 2.90-3.06 (m, 3H), 2.49-2.62 (m, 2H), 2.36-2.48 (m, 1H), 2.23-2.35 (m, 1H), 1.96-2.17 (m, 6H), 1.45 (s, 9H). MS: Calcd. for $C_{29}H_{37}ClF_2NO_7S_2$ (MH$^+$) m/z=648.2. found 647.9. HPLC (Method 2) 95.7% (AUC), $t_R$=15.93 min. $[\alpha]^{20}_D$=−140.0° (c 0.11, chloroform).

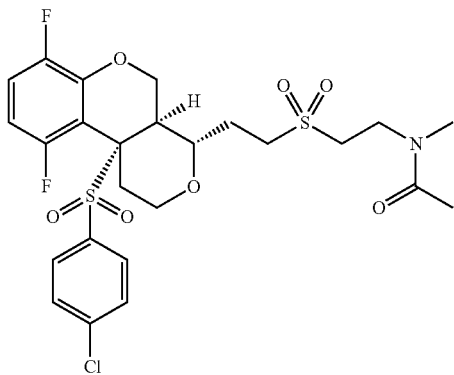

46d $^1$H NMR (CDCl$_3$ 400 MHz) δ 7.62 (d, J=8.8H, 2H), 7.50 (d, J=8.8 Hz, 2H), 7.08 (m, 1H), 6.45 (m, 1H), 5.14 (dd, J=12.8, 2.8 Hz, 1H), 4.44 (d, J=12.8 Hz, 1H), 3.85 (m, 1H), 3.78 (m, 2H), 3.10-3.38 (m, 4H), 3.12 (s, 3H), 3.0 (m, 2H), 2.41 (m, 1H), 2.25 (m, 1H), 2.06 (s, 3H), 2.0 (m, 1H). MS: Calcd. for C$_{25}$H$_{29}$ClF$_2$NO$_7$S$_2$ (MH$^+$), 592.1. found 592.3. Retention time: 4.10/7.5 min.

under reduced pressure. The residue was lyophilized (H$_2$O/HCl/CH$_3$CN) to afford 0.069 g (93%) of 47 as an off-white solid [mixture of rotomers (54:46)]: Major rotomer: $^1$H NMR (DMSO-d$_6$ 500 MHz) 11.22 (s, 1H), 7.71-7.79 (m, 4H), 7.39-7.47 (m, 1H), 6.76 (ddd, 13.0, 9.2, 4.0 Hz, 2H), 4.93 (dd, J=12.8, 2.4 Hz, 1H), 4.57 (d, J=12.6 Hz, 1H), 4.13-4.24 (m, 0.66H), 3.89-3.96 (m, 3H), 3.77 (s, 2H), 3.59 (s, 1H), 3.31 (t, J=7.9 Hz, 3H), 3.03 (t, J=11.6 Hz, 1H), 2.84 (s, 3H), 2.54 (d, J=13.9 Hz, 1H), 2.45 (d, J=10.1 Hz, 1H), 2.22-2.34 (m, 1H), 2.17 (t, J=12.1 Hz, 1H), 1.94 (ddd, J=14.8, 12.7, 7.6 Hz, 1H).

Minor rotomer: $^1$H NMR (DMSO-d$_6$ 500 MHz) δ 10.43 (s, 0.4H), 7.71-7.79 (m, 4H), 7.39-7.47 (m, 1H), 6.76 (ddd, J=13.0, 9.2, 4.0 Hz, 2H), 4.93 (dd, J=12.8, 2.4 Hz, 1H), 4.57 (d, J=12.6 Hz, 1H), 4.29 (s, 0.47H), 3.89-3.96 (m, 3H), 3.77 (s, 2H), 3.51 (s, 1H), 3.31 (t, J=7.9 Hz, 3H), 3.03 (t, J=11.6 Hz, 1H), 2.84 (s, 3H), 2.54 (d, J=13.9 Hz, 1H), 2.45 (d, J=10.1 Hz, 1H), 2.22-2.34 (m, 1H), 2.17 (t, J=12.1 Hz, 1H), 1.94 (ddd, J=14.8, 12.7, 7.6 Hz, 1H). MS: Calcd. for C$_{25}$H$_{29}$ClF$_2$NO$_6$S$_2$ (MH$^+$), m/z=576.1. found 576.0. HPLC (Method 2) >99% (AUC), t$_R$=11.57 min.

SCHEME 20

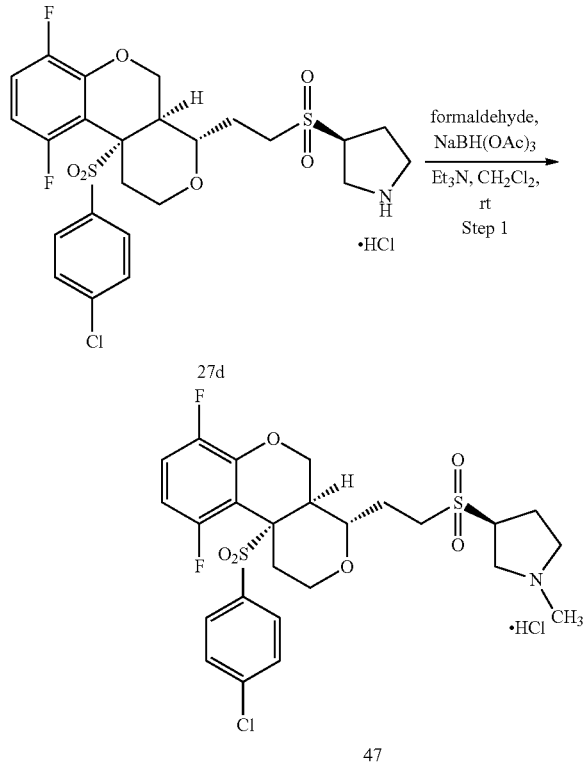

SCHEME 21

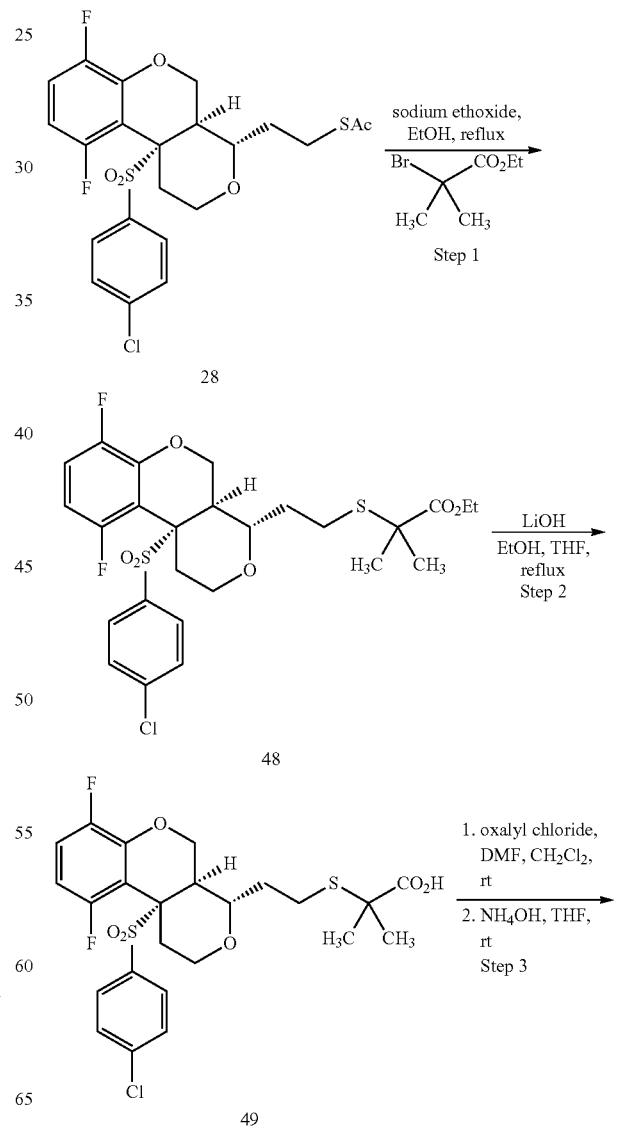

A solution of 0.072 g (0.121 mmol) of compound 27d, 0.004 g (37% wt in H$_2$O, 0.121 mmol) of formaldehyde, 0.036 g (0.169 mmol) of sodium triacetoxy borohydride and 0.024 g (0.242 mmol) of triethylamine in 1.5 mL of methylene chloride was stirred at room temperature for 2 h. The reaction was then quenched with 5 mL of saturated aqueous sodium bicarbonate and extracted with three 10 mL portions of methylene chloride. The combined extracts were dried over anhydrous magnesium sulfate, filtered, and concentrated -continued

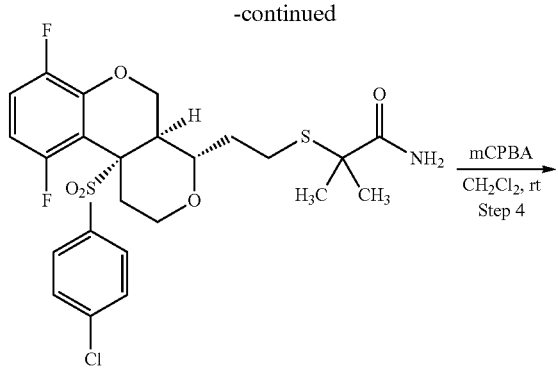

50a

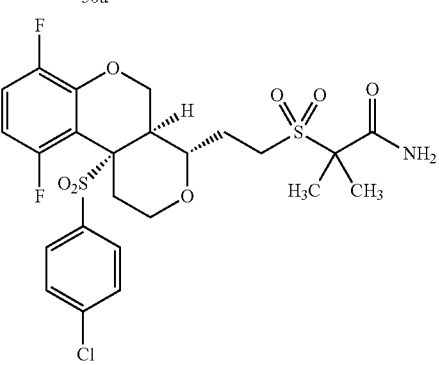

51a

Step 1

A solution of freshly prepared sodium ethoxide (Na, 10 mg, 0.440 mmol in 3 mL of absolute ethanol) was added to a suspension of 0.22 g (0.437 mmol) of compound 28 in 4 mL of absolute ethanol at room temperature. The mixture was heated at reflux for 5 h and then allowed to cool to room temperature overnight. The solvent was removed, 10 mL of water was added, and the resulting mixture was extracted with two 15 mL portions of ethyl acetate. The combined extracts were dried over anhydrous sodium sulfate, filtered, and concentrated under reduced pressure. The residue was purified by column chromatography (silica, 0-35% EtOAc/heptane) to provide 0.226 g (89%) of compound 48 as an off-white semi-solid: $^1$H NMR (CDCl$_3$ 300 MHz) δ 7.63 (d, J=8.6 Hz, 2H), 7.51 (d, J=8.6 Hz, 2H), 7.08 (m, 1H), 6.45 (m, 1H), 5.13 (d, J=12.4 Hz, 1H), 4.43 (d, J=12.4 Hz, 1H), 4.16 (q, J=14.1 Hz, 2H), 3.87 (m, 1H), 3.31 (m, 1H), 3.12 (t, J=11.1 Hz, 1H), 2.73 (m, 1H), 2.62 (m, 1H), 2.54 (m, 2H), 2.28 (m, 1H), 2.06 (m, 1H), 1.75 (m, 1H), 1.48 (d, J=2.4 Hz, 6H), 1.28 (m, 3H).

Step 2

To a solution of 0.53 g (0.92 mmol) of compound 48 in 18 mL of ethanol and 18 mL of THF was added a solution of 0.19 g (4.62 mmol) of lithium hydroxide in 10 mL of water at room temperature. The resulting solution was then heated at reflux for 24 h and then concentrated to dryness. The residue was acidified to pH 1 with 1 N hydrochloric acid and the product was extracted with three 25 mL portions of EtOAc. The combined extracts were dried over anhydrous sodium sulfate and filtered. The solvent was removed under reduced pressure to provide 0.45 g (89%) of compound 49 as a clear colorless film: $^1$H NMR (CDCl$_3$ 300 MHz) 7.63 (d, J=8.6 Hz, 2H), 7.51 (d, J=8.6 Hz, 2H), 7.09 (m, 1H), 6.46 (m, 1H), 5.14 (d, J=12.1 Hz, 1H), 4.43 (d, J=12.3 Hz, 1H), 3.90 (m, 1H), 3.37 (m, 1H), 3.13 (t, J=11.1 Hz, 1H), 2.86 (m, 1H), 2.65 (m, 1H), 2.54 (m, 2H), 2.28 (m, 1H), 2.09 (m, 1H), 1.83 (m, 1H), 1.50 (s, 6H).

Step 3

To a solution of 0.21 g (0.38 mmol) of compound 49 and 0.01 mL of DMF in 15 mL of methylene chloride was slowly added 0.10 mL (1.10 mmol) of oxalyl chloride under nitrogen at room temperature. After 1 h, the solvent was removed under reduced pressure and the residue was taken up in 15 mL of THF. Concentrated ammonium hydroxide (1.3 mL, 19.0 mmol) was then added at room temperature and the reaction mixture was allowed to stir for 15 h under nitrogen. The reaction mixture was partitioned between 10 mL of water and 25 mL of EtOAc. The layers were separated and the aqueous layer was extracted with two 25 mL portions of EtOAc. The combined organic layers were dried over anhydrous sodium sulfate and filtered. The solvent was removed under reduced pressure to provide 0.21 g of crude compound 50a, which was used without further purification: $^1$H NMR (CDCl$_3$ 300 MHz) δ 7.64 (d, J=8.6 Hz, 2H), 7.49 (d, J=8.6 Hz, 2H), 7.10 (m, 1H), 6.68 (s, 1H), 6.46 (m, 1H), 5.15 (d, J=12.2 Hz, 1H), 4.43 (d, J=12.2 Hz, 1H), 3.87 (m, 1H), 3.33 (m, 1H), 3.11 (t, J=11.1 Hz, 1H), 2.75 (m, 1H), 2.59 (m, 3H), 2.27 (m, 1H), 2.11 (m, 1H), 1.75 (m, 1H), 1.48 (s, 6H). MS: Calcd. for C$_{24}$H$_{26}$ClF$_2$NNaO$_5$S$_2$(MNa$^+$), m/z=568.1. found 568.2. Retention time: 3.03 min.

The following compounds were prepared analogously:

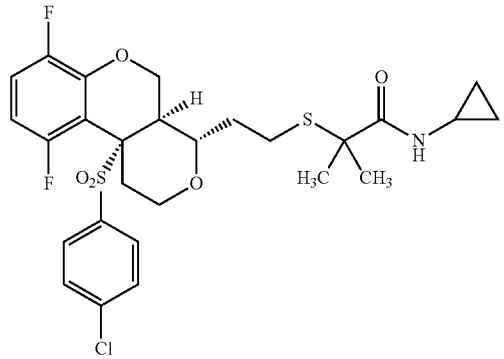

50b $^1$H NMR (CDCl$_3$ 500 MHz) δ 7.63 (d, J=8.6 Hz, 2H), 7.50 (d, J=8.6 Hz, 2H), 7.10 (m, 1H), 6.97 (s, 1H), 6.47 (m, 1H), 5.14 (d, J=12.2 Hz, 1H), 4.41 (d, J=12.2 Hz, 1H), 3.88 (m, 1H), 3.28 (m, 1H), 3.11 (m, 1H), 2.69 (m, 1H), 2.53 (m, 3H), 2.29 (m, 1H), 2.06 (m, 1H), 1.77 (m, 1H), 1.44 (m, 6H), 0.76 (m, 2H), 0.46 (m, 2H). MS: Calcd. for C$_{27}$H$_{30}$ClF$_2$NNaO$_5$S$_2$ (MNa$^+$), m/z=608.1. found 608.2. Retention time: 3.26 min.

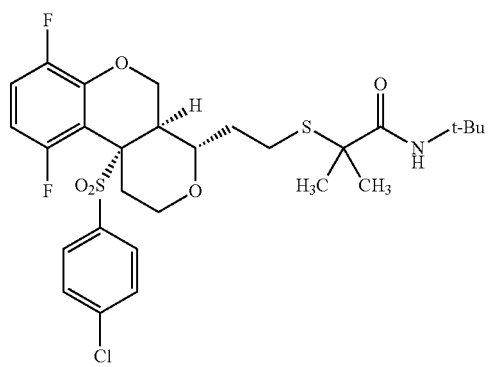

50c $^1$H NMR (CDCl$_3$ 500 MHz) δ 7.63 (d, J=8.6 Hz, 2H), 7.50 (d, J=8.6 Hz, 2H), 7.10 (m, 1H), 6.85 (s, 1H), 6.51 (m, 1H), 5.14 (d, J=12.2 Hz, 1H), 4.41 (d, J=12.2 Hz, 1H), 3.82 (m,

1H), 3.23 (m, 1H), 3.12 (m, 1H), 2.63 (m, 1H), 2.53 (m, 3H), 2.30 (m, 1H), 2.04 (m, 1H), 1.79 (m, 1H), 1.48 (m, 6H), 1.32 (s, 9H). MS: Calcd. for $C_{28}H_{34}ClF_2NNaO_5S_2(MNa^+)$, m/z=624.1; found 624.1. Retention time: 3.68 min.

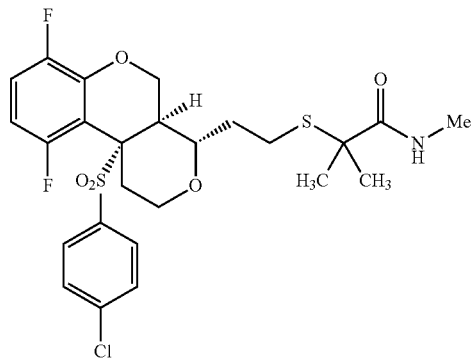

50d

MS: Calcd. for $C_{25}H_{28}ClF_2NNaO_5S_2(MNa^+)$, m/z=582.1. found 582.1. Retention time: 3.10 min.

Step 4

To a solution of 0.21 g of compound 50a in 10 mL of methylene chloride was added 0.27 g (1.56 mmol) of 3-chloroperbenzoic acid (mCPBA) at room temperature. The reaction mixture was stirred for 3 h and then quenched with 10 mL of saturated aqueous sodium bicarbonate. The mixture was stirred for 1 h after which time the layers were separated and the aqueous layer was extracted with three 15 mL portions of methylene chloride. The combined organic extracts were dried over anhydrous sodium sulfate and filtered. The solvent was removed under reduced pressure and the residue was purified by preparative HPLC (Method 1) and then lyophilized ($CH_3CN/H_2O$) to provide compound 51a (0.070 g, 32% over two steps) as an off-white solid: $^1$H NMR (DMSO-$d_6$ 500 MHz) δ 7.74 (s, 4H), 7.51 (s, 1H), 7.45 (s, 1H), 7.08 (m, 1H), 7.41 (m, 1H), 6.74 (m, 1H), 4.93 (d, J=12.4 Hz, 1H), 4.52 (d, J=12.4 Hz, 1H), 3.90 (m, 1H), 3.87 (m, 1H), 3.23 (m, 1H), 3.02 (t, J=11.7 Hz, 1H), 2.52 (m, 1H), 2.36 (m, 1H), 2.24 (m, 1H), 2.17 (m, 1H), 1.87 (m, 1H), 1.48 (m, 6H). MS: Calcd. for $C_{24}H_{26}ClF_2NNaO_7S_2(MNa^+)$, m/z=600.1. found 600.0. Retention time: 3.11 min. HPLC (Method 2) 98.4% (AUC), $t_R$=7.40 min. $[α]25_D$=−111.0° (c 0.10, methylene chloride).

The following compounds were prepared analogously:

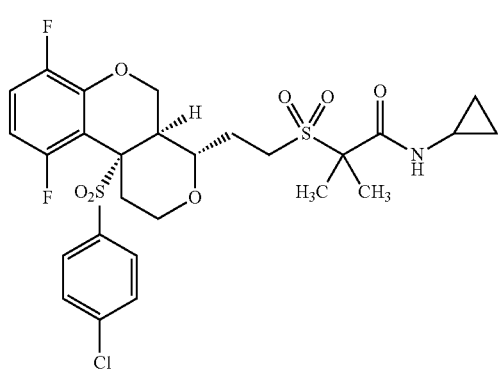

51b $^1$H NMR (CDCl$_3$ 300 MHz) δ 7.63 (d, J=8.6 Hz, 2H), 7.51 (d, J=8.6 Hz, 2H), 7.10 (m, 1H), 6.72 (s, 1H), 6.47 (m, 1H), 5.15 (d, J=12.2 Hz, 1H), 4.44 (d, J=12.2 Hz, 1H), 3.89 (m, 1H), 3.28 (m, 2H), 3.12 (m, 1H), 2.96 (m, 1H), 2.74 (m, 1H), 2.53 (m, 2H), 2.43 (m, 1H), 2.29 (m, 1H), 2.04 (m, 1H), 1.59 (s, 6H), 0.79 (m, 2H), 0.50 (m, 2H). MS: Calcd. for $C_{27}H_{30}ClF_2NNaO_7S_2(MNa^+)$, m/z=640.1. found 640.1. Retention time: 3.38 min HPLC (Method 2) >99% (AUC), $t_R$=16.50 min. $[α]^{25}_D$=−111.0° (c 0.10, methylene chloride).

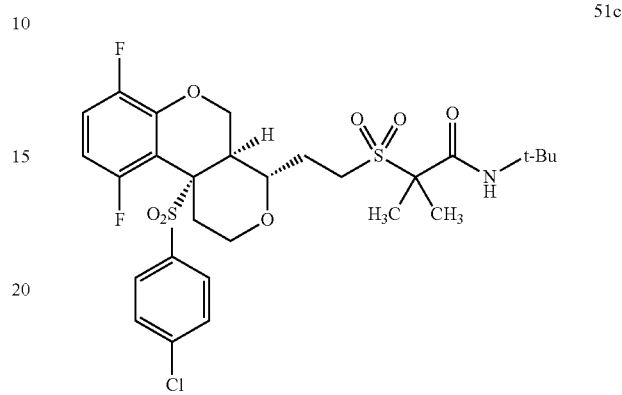

51c $^1$H NMR (DMSO-$d_6$ 500 MHz) δ 7.74 (s, 4H), 7.42 (m, 1H), 6.88 (m, 1H), 6.77 (m, 1H), 4.96 (d, J=12.4 Hz, 1H), 4.53 (d, J=12.4 Hz, 1H), 3.93 (m, 1H), 3.23 (m, 3H), 3.07 (m, 1H), 2.58 (m, 1H), 2.42 (m, 1H), 2.28 (m, 1H), 2.17 (m, 1H), 1.93 (m, 1H), 1.51 (s, 3H), 1.49 (s, 3H), 1.26 (s, 9H). MS: Calcd. for $C_{28}H_{34}ClF_2NNaO_7S_2(MNa^+)$, m/z=656.1. found 656.1. Retention time: 3.40 min. HPLC (Method 2) >99% (AUC), $t_R$=17.80 min. $[α]^{25}_D$=109.0° (c 0.10, methylene chloride).

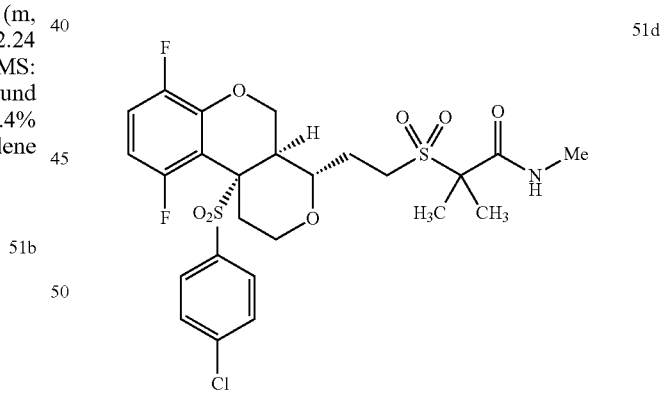

51d $^1$H NMR (CDCl$_3$ 300 MHz) δ 7.63 (d, J=8.6 Hz, 2H), 7.51 (d, J=8.6 Hz, 2H), 7.10 (m, 1H), 6.66 (s, 1H), 6.47 (m, 1H), 5.17 (d, J=12.2 Hz, 1H), 4.45 (d, J=12.2 Hz, 1H), 3.87 (m, 1H), 3.29 (m, 2H), 3.12 (m, 1H), 2.96 (m, 1H), 2.86 (d, J=4.8 Hz, 3H), 2.53 (m, 2H), 2.43 (m, 1H), 2.29 (m, 1H), 2.04 (m, 1H), 1.63 (s, 6H). MS: Calcd. for $C_{25}H_{28}ClF_2NNaO_7S_2$ $(MNa^+)$, m/z=614.1. found 614.2. Retention time: 3.44 min. HPLC (Method 2) >99% (AUC), $t_R$=17.10 min. $[α]^{25}_D$=−117.0° (c 0.10, methylene chloride).

SCHEME 22

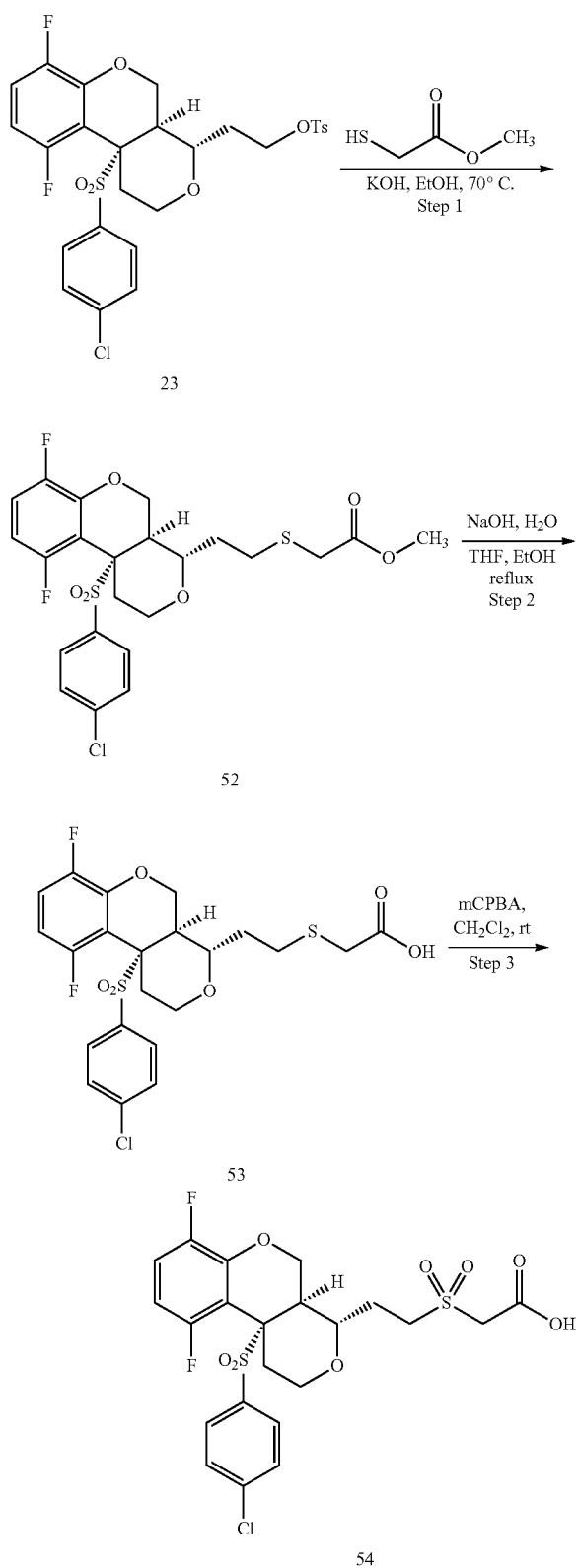

ethanol was added a solution of 0.67 mL (1 M, 0.67 mmol) of potassium hydroxide in ethanol and the resulting mixture was stirred at 70° C. for 2 h. After this time, the solvent was removed under reduced pressure and the resulting residue was dissolved in 15 mL of methylene chloride, washed with 100 mL of saturated aqueous sodium bicarbonate and 25 mL of water, dried over anhydrous sodium sulfate, filtered, and concentrated under reduced pressure. The residue was purified by preparative thin layer chromatography (30% EtOAc/hexanes) to give 0.176 g (99%) of 52 as a white solid: MS: Calcd. for $C_{23}H_{25}ClF_2O_7S_2$ $(MH_2O^+)$, m/z=550.1. found 550.2. Retention time: 2.33 min.

Step 2

To a stirred solution of 0.176 g (0.33 mmol) of compound 52 in 2 mL of ethanol and 2 mL of THF was added a solution of 0.033 g (0.83 mmol) of sodium hydroxide in 2 mL of water and the reaction mixture stirred at reflux for 1 h. The reaction mixture was allowed to cool to room temperature and acidified with 50 mL of 1 N hydrochloric acid. The product was extracted with three 15 mL portions of methylene chloride. The combined extracts were dried over anhydrous sodium sulfate, filtered, and concentrated under reduced pressure to give 0.165 g (96%) of 53 as a yellow oil: MS: Calcd. for $C_{22}H_{23}ClF_2O_7S_2(MH_2O^+)$, m/z=536.1. found 536.2. Retention time: 2.11 min.

Step 3

A solution of 0.165 g (0.32 mmol) of compound 53 and 0.36 g (1.59 mmol) of 3-chloroperoxybenzoic acid (mCPBA) in 3 mL of methylene chloride was stirred at room temperature for 1 h. After this time, the reaction mixture was diluted with 10 mL of methylene chloride and washed with 100 mL of saturated aqueous sodium bicarbonate. The aqueous layer was back extracted with three 15 ml, portions of methylene chloride. The combined organic layers were dried over anhydrous sodium sulfate, filtered, and concentrated. The residue was purified by preparative thin layer chromatography (9% MeOH/$CH_2Cl_2$) to give 0.089 g (51%) of 54 as a white solid: $^1$H NMR (DMSO-$d_6$ 500 MHz) δ 13.53 (br s, 1H), 7.75 (m, 4H), 7.41 (m, 1H), 6.75 (m, 1H), 4.91 (m, 1H), 4.57 (d, J=12.5 Hz, 1H), 4.13 (m, 2H), 3.91 (m, 1H), 3.40 (m, 1H), 3.27 (m, 2H), 3.04 (t, J=12.0 Hz, 1H), 2.52 (m, 1H), 2.39 (m, 1H), 2.27 (m, 1H), 2.15 (m, 1H), 1.92 (m, 1H). MS: Calcd. for $C_{22}H_{23}ClF_2O_9S_2$ $(MH_2O^+)$, m/z=568.0. found 568.2. Retention time: 2.00 min. HPLC (Method 2) >99% (AUC), $t_R$=14.47 min. $[α]^{25}{}_D$=−146.3° (c 0.054 MeOH).

SCHEME 23

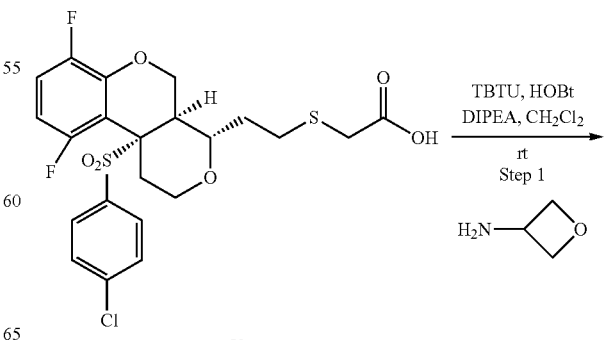

Step 1

To a stirred solution of 0.20 g (0.33 mmol) of compound 23 and 0.06 g (0.67 mmol) of methyl thioglycolate in 2 mL of

73

-continued

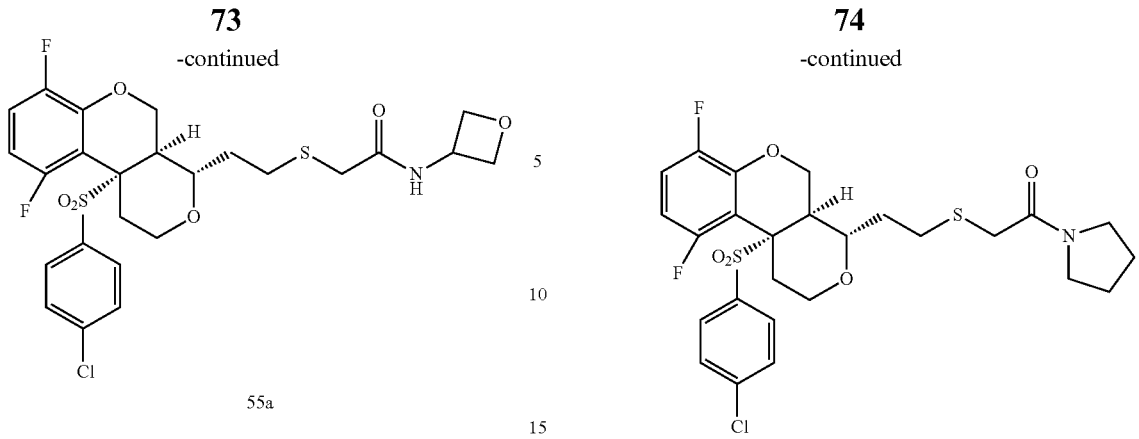

55a

Step 1

To a stirred solution of 0.183 g (0.332 mmol) of compound 53 in 5 mL of methylene chloride under nitrogen was added 0.16 g (0.50 mmol) of TBTU, 0.067 g (0.50 mmol) of HOBT, 0.3 mL (1.66 mmol) of diisopropylethylamine, and 0.048 g (0.664 mmol) of oxetan-3-amine. The reaction was stirred at room temperature for 3 h. After this time, the reaction was diluted with 25 mL of methylene chloride and washed with 50 mL of water (50 mL). The aqueous layer was separated and extracted with three 25 mL portions of methylene chloride. The combined organics were dried over anhydrous magnesium sulfate, filtered, and concentrated. The residue was purified by flash chromatography (silica, 0-10% methanol/methylene chloride) to afford 0.20 g (99%) of 55a as a white solid: MS: Calcd. for $C_{25}H_{27}ClF_2NO_6S_2$ (MH$^+$), m/z=574.1. found 574.1. Retention time: 2.11 min.

The following compound was prepared analogously:

55b

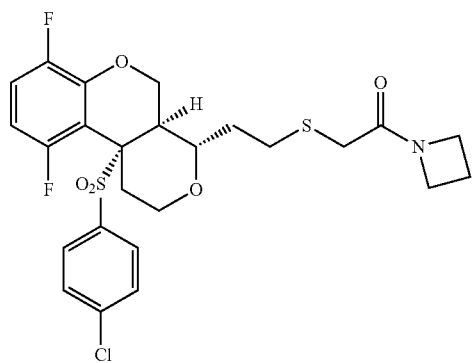

MS Calcd. for $C_{25}H_{23}ClF_2NO_5S_2$ (MH$^+$), m/z=558.1. found 558.1. Retention time 2.18 min.

SCHEME 24

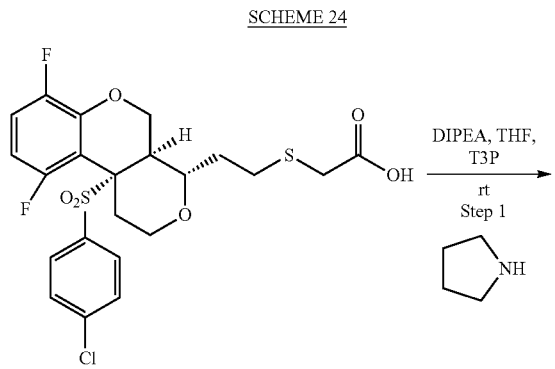

53

74

-continued

55c

Step 1

To a stirred solution of 0.023 g (0.044 mmol) of compound 53 in 0.5 mL of THF was added 7 (0.089 mmol) of pyrrolidine, 0.03 mL (0.17 mmol) of diisopropylethylamine, and 0.08 mL (50% in DMF, 0.266 mmol) of T3P. The reaction was stirred at room temperature overnight. After this time, the reaction was diluted with 20 mL of methylene chloride and washed with 20 mL of saturated aqueous sodium bicarbonate. The aqueous layer was separated and extracted with three 20 mL portions of methylene chloride. The combined organics were dried over anhydrous sodium sulfate, filtered, and concentrated. The residue was dissolved in 25 mL of ethyl acetate and washed with 50 mL of 5% aqueous lithium chloride and 50 mL of brine. The organic layer was separated, dried over anhydrous sodium sulfate, filtered, and concentrated to afford 0.024 g (94%) of 55c as an off-white solid: MS: Calcd. for $C_{26}H_{29}ClF_2NO_5S_2$ (MH$^+$), m/z=572.1. found 572.2. Retention time: 2.22 min.

The following compounds were prepared analogously:

55d

MS: Calcd. for $C_{26}H_{31}ClF_2NO_5S_2$ (MH$^+$), m/z=574.1. found 574.2. Retention time: 2.32 min.

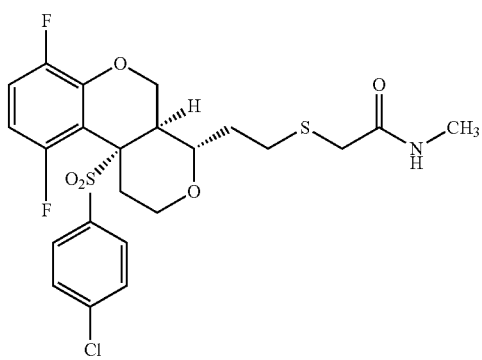

MS: Calcd. for $C_{23}H_{25}ClF_2NO_5S_2$ (MH+), m/z=532.1. found 532.2. Retention time: 2.02 min.

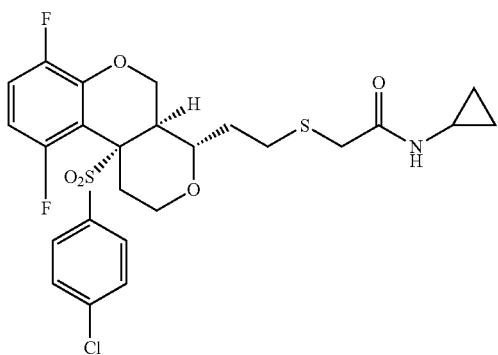

MS: Calcd. for $C_{25}H_{27}ClF_2NO_5S_2$ (MH+), m/z=558.1. found 558.2. Retention time: 2.11 min.

SCHEME 25

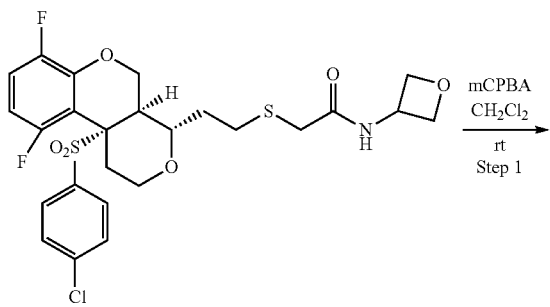

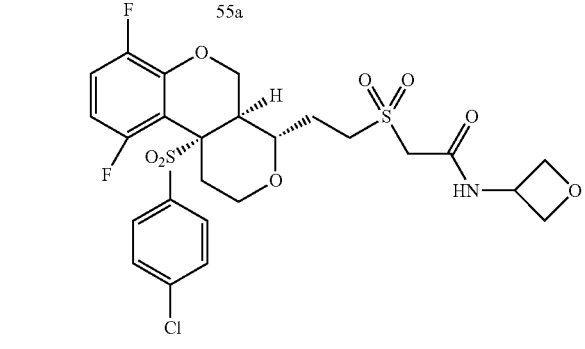

Step 1

To a stirred solution of 0.20 g (0.35 mmol) of compound 55a in 4.5 mL of methylene chloride was added 0.607 g (70%, 3.52 mmol) of 3-chloroperbenzoic acid. The reaction was stirred at room temperature for 3 h. After this time, the reaction was diluted with 40 mL of methylene chloride and washed with 50 mL of 10% sodium thiosulfate and 50 mL of saturated aqueous sodium bicarbonate. The organic layer was separated, dried over anhydrous sodium sulfate, filtered, and concentrated. The residue was purified by preparative HPLC (Method 1) and lyophilized ($CH_3CN/H_2O$) to afford 0.115 g (57%) of 56a as a white solid: $^1$H NMR ($CDCl_3$ 500 MHz) δ 7.64 (d, J=8.3 Hz, 2H), 7.57-7.46 (m, 2H), 7.20-7.01 (m, 2H), 6.59-6.35 (m, 1H), 5.18 (d, J=12.7 Hz, 1H), 5.10-4.97 (m, 1H), 4.97-4.83 (m, 2H), 4.65-4.51 (m, 2H), 4.46 (d, J=12.7 Hz, 1H), 4.05-3.78 (m, 3H), 3.50-3.39 (m, 1H), 3.37 (t, J=9.5 Hz, 1H), 3.27-3.05 (m, 2H), 2.75-2.50 (m, 2H), 2.45 (t, J=12.2 Hz, 1H), 2.30 (t, J=12.0 Hz, 1H), 2.16-2.03 (m, 1H). MS: Calcd. for $C_{25}H_{27}ClF_2NO_8S_2$ (MH+), m/z=606.1. found 606.1. HPLC (Method 2) 97.8% (AUC), $t_R$=14.10 min. $[\alpha]^{25}_D$=−130.0° (c 0.090, Methanol).

The following compounds were prepared analogously:

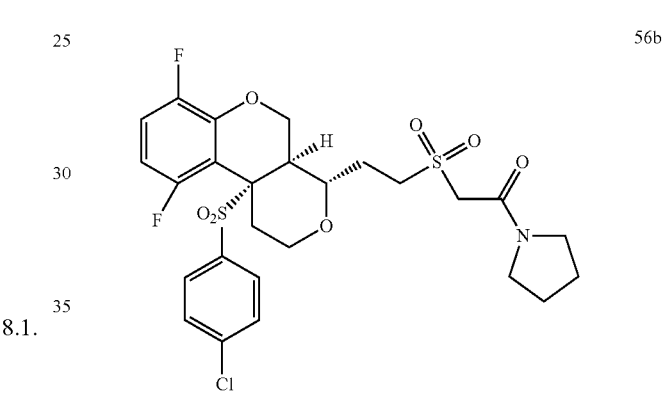

$^1$H NMR (DMSO-$d_6$ 500 MHz) δ 7.80-7.71 (m, 4H), 7.48-7.38 (m, 1H), 6.81-6.70 (m, 1H), 4.92 (dd, J=12.8, 2.5 Hz, 1H), 4.57 (d, J=12.5 Hz, 1H), 4.32 (s, 2H), 3.91 (d, J=11.9 Hz, 1H), 3.52 (t, J=6.8 Hz, 2H), 3.45-3.37 (m, 1H), 3.31-3.16 (m, 3H), 3.04 (t, J=11.6 Hz, 1H), 2.54 (d, J=13.7 Hz, 2H), 2.39 (d, J=10.6 Hz, 1H), 2.33-2.24 (m, 1H), 2.16 (t, J=11.7 Hz, 1H), 2.01-1.88 (m, 1H), 1.88-1.83 (m, 2H), 1.83-1.72 (m, 2H). MS: Calcd. for $C_{26}H_{29}ClF_2NO_7S_2$ (MH+), m/z=604.1. found 604.0. Retention time 2.97 min. HPLC (Method 2) 98.8% (AUC), $t_R$=15.42 min. $[\alpha]^{25}_D$=−78.7° (c 0.050, Methanol).

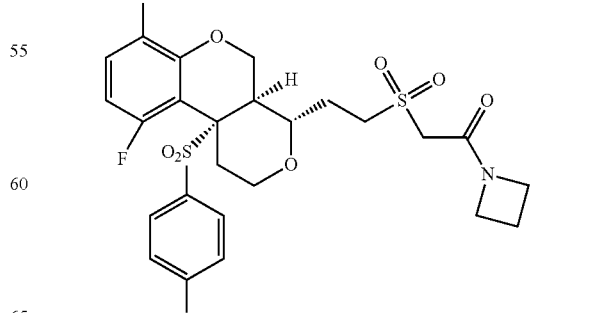

¹H NMR (CDCl₃ 500 MHz) δ 7.64 (d, J=8.5 Hz, 2H), 7.51 (d, J=8.7 Hz, 2H), 7.16-7.05 (m, 1H), 6.52-6.42 (m, 1H), 5.17 (dd, J=12.7, 2.5 Hz, 1H), 4.49 (d, J=12.5 Hz, 1H), 4.44-4.29 (m, 2H), 4.10 (t, J=7.8 Hz, 2H), 3.94-3.85 (m, 1H), 3.73 (s, 2H), 3.60-3.49 (m, 1H), 3.41-3.34 (m, 1H), 3.34-3.24 (m, 1H), 3.13 (t, J=11.7 Hz, 1H), 2.61-2.49 (m, 2H), 2.49-2.39 (m, 1H), 2.39-2.23 (m, 3H), 2.15-2.03 (m, 1H). MS: Calcd. for C₂₅H₂₆ClF₂NNaO₇S₂ (MNa⁺), m/z=612.1; found 612.1. Retention time 2.85 min. HPLC (Method 2) 95.4% (AUC), t$_R$=14.78 min. [α]²⁵$_D$=119.0° (c 0.110, Methanol).

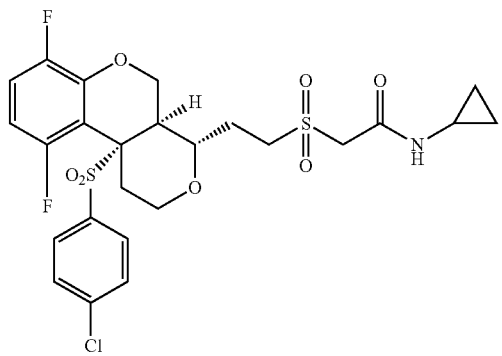

56f

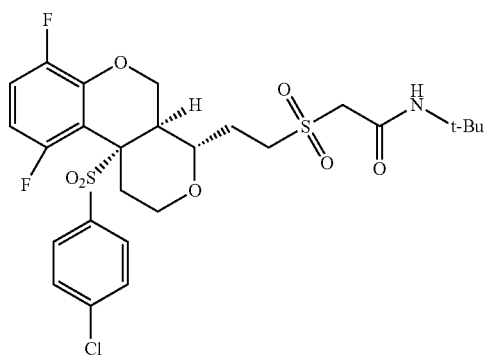

56d

¹H NMR (CDCl₃ 500 MHz) δ 7.64 (d, J=8.6 Hz, 2H), 7.51 (d, J=8.8 Hz, 2H), 7.17-7.06 (m, 1H), 6.53-6.42 (m, 1H), 6.12 (s, 1H), 5.17 (dd, J=12.7, 2.6 Hz, 1H), 4.46 (d, J=12.6 Hz, 1H), 3.97-3.83 (m, 1H), 3.74 (q, J=14.4 Hz, 2H), 3.47-3.28 (m, 2H), 3.22-3.06 (m, 2H), 2.55 (t, J=12.1 Hz, 2H), 2.50-2.38 (m, 1H), 2.29 (t, J=12.0 Hz, 1H), 2.13-2.02 (m, 1H), 1.37 (s, J=4.0 Hz, 9H). MS: Calcd. for C₂₆H₃₁ClF₂NO₇S₂ (MH⁺), m/z=606.1. found 606.1. Retention time: 3.19 min. HPLC (Method 2) >99% (AUC), t$_R$=16.50 min. [α]²⁵$_D$=−132.0° (c 0.001, Methanol).

¹H NMR (CDCl₃ 500 MHz) δ 7.63 (d, J=8.5 Hz, 2H), 7.51 (d, J=8.5 Hz, 2H), 7.12-7.11 (m, 1H), 6.48-6.44 (m, 1H), 6.40 (br s, 1H), 5.17 (dd, J=12.5, 2.5 Hz, 1H), 4.46 (d, J=12.5 Hz, 1H), 3.92-3.89 (m, 1H), 3.83-3.75 (m, 2H), 3.42-3.34 (m, 2H), 3.17-3.14 (m, 2H), 2.77-2.75 (m, 1H), 2.58-2.52 (m, 2H), 2.45-2.40 (m, 1H), 2.32-2.25 (m, 1H), 2.07-1.99 (m, 1H), 0.85-0.81 (m, 2H), 0.59-0.57 (m, 2H). MS: Calcd. for C₂₅H₂₆ClF₂NNaO₇S₂ (MNa⁺), m/z=612.1; found 612.0. Retention time: 2.90 min. HPLC (Method 2) 98.7% (AUC), t$_R$=18.43 min.

SCHEME 26

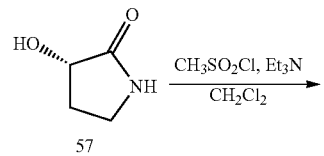

57

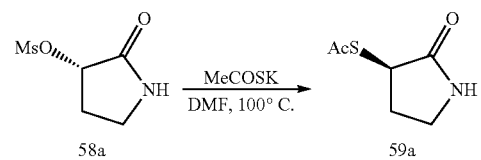

58a     59a

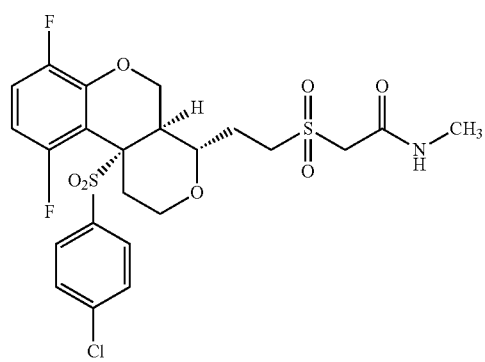

56e

¹H NMR (CDCl₃ 500 MHz) δ 7.63 (d, J=8.5 Hz, 2H), 7.51 (d, J=9.0 Hz, 2H), 7.12-7.11 (m, 1H), 6.49-6.45 (m, 1H), 6.33 (br s, 1H), 5.17 (dd, J=12.5, 2.5 Hz, 1H), 4.45 (d, J=12.5 Hz, 1H), 3.91-3.88 (m, 1H), 3.87-3.80 (m, 2H), 3.44-3.34 (m, 2H), 3.19-3.11 (m, 2H), 2.89-2.88 (m, 3H), 2.58-2.52 (m, 2H), 2.45-2.30 (m, 1H), 2.30-2.29 (m, 1H), 2.08-2.06 (m, 1H). MS: Calcd. for C₂₃H₂₄ClF₂NNaO₇S₂ (MNa⁺), m/z=586.1. found 586.4. Retention time: 2.70 min. HPLC (Method 2) >99% (AUC), t$_R$=17.61 min.

Step 1

To a stirred solution of 0.50 (4.95 mmol) of compound 57 and 1.4 g (9.90 mmol) of triethylamine in 50 mL of methylene chloride was added 0.6 mL (7.42 mmol) of methanesulfonyl chloride at 0° C. under nitrogen. The reaction mixture was warmed to room temperature and stirred for 3 days. After this time, the reaction mixture was poured into 20 mL of water and the layers were separated. The aqueous layer was extracted with three 20 mL portions of methylene chloride. The combined organics were washed with 15 mL of 1 N hydrochloric acid and 20 mL of brine, dried over anhydrous magnesium sulfate, filtered, and concentrated to afford 0.518 g (58%) of 58a as a white solid: MS: Calcd. for C₅H₁₀NO₄S (MH⁺), m/z=180.0. found 180.1. Retention time: 1.02 min.

The following compounds were prepared analogously:

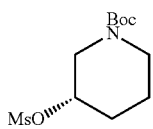

58b

MS: Calcd. for $C_{11}H_{21}NNaO_5S$ (MNa⁺), m/z=302.1. found 302.0. Retention time: 2.68 min

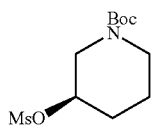

58c

MS: Calcd. for $C_{11}H_{21}NNaO_5S$ (MNa⁺), m/z=302.1. found 302.0. Retention time: 2.65 min.

Step 2

A solution of 0.25 g (1.40 mmol) of compound 58a and 0.49 g (3.49 mmol) of potassium thioacetate in 5 mL of DMF was heated at 100° C. for 1 h. After this time, the reaction mixture was cooled to room temperature and diluted with 15 mL of saturated aqueous ammonium chloride and 10 mL of water. The resulting mixture was extracted with four 15 mL portions of methylene chloride. The combined organics were washed with two 10 mL portions of water and 10 mL of brine, dried over anhydrous magnesium sulfate, filtered, and concentrated to afford crude 0.570 g 59a, which was used in the subsequent step without further purification: MS: Calcd. for $C_6H_{10}NO_2S$ (MH⁺), m/z=160.0. found 160.3.

The following compounds were prepared analogously:

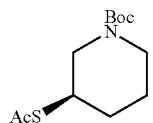

59b

MS: Calcd. for $C_{12}H_{21}NNaO_3S$ (MNa⁺), m/z=282.1. found 282.1. Retention time: 3.00 min.

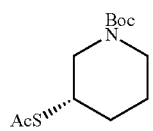

59c

MS: Calcd. for $C_{12}H_{21}NNaO_3S$ (MNa⁺), m/z=282.1. found 282.0. Retention time: 3.04 min.

SCHEME 27

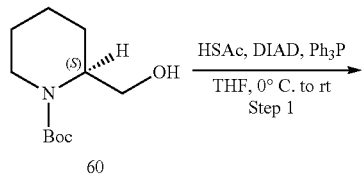

60

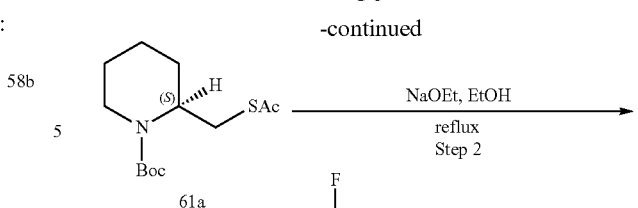

61a

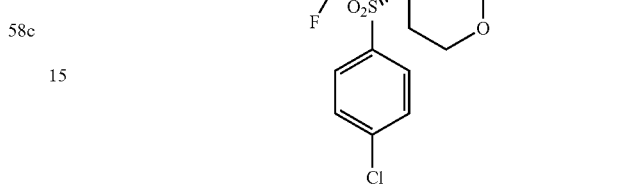

23

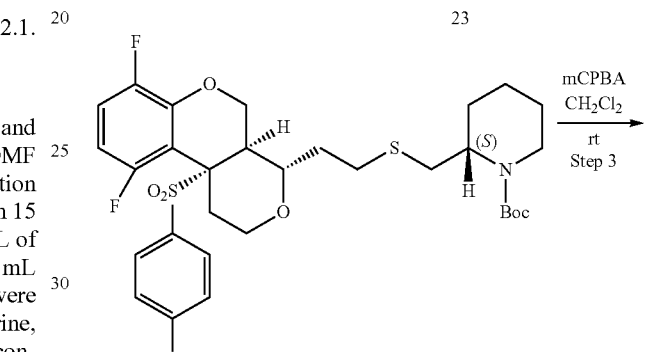

62a

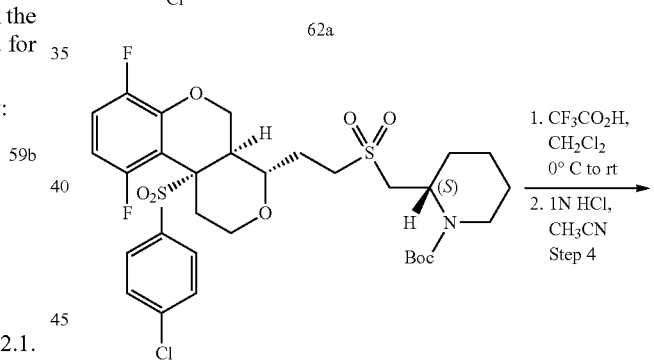

63a

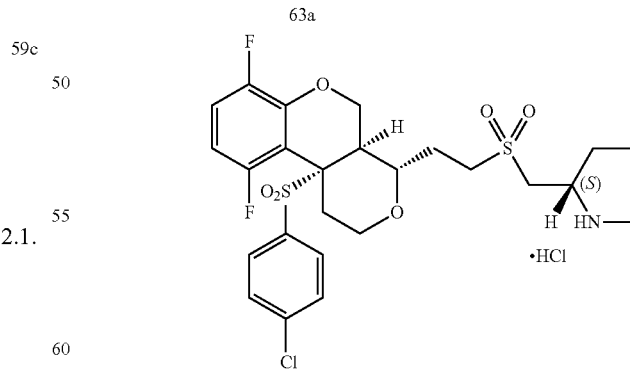

64a

Step 1

To a stirred solution of 0.365 g (1.40 mmol) of triphenylphosphine in 5 mL of THF was added 0.27 mL (1.40 mmol) of DIAD. The solution was cooled to 0° C. and stirred for 20 min. A solution of 0.25 g (1.16 mmol) of compound 60 in 2.5 mL of THF and 0.1 mL (1.40 mmol) of thioacetic acid were added and the reaction was warmed to room temperature and stirred overnight. After this time, the reaction was concentrated and the residue was purified by flash chromatography (silica, 0-55% ethyl acetate/heptane) to afford 0.255 g (80%) of 61a as a white solid: $^1$H NMR (CDCl$_3$ 300 MHz) δ 4.34 (s, 1H), 3.99 (d, J=11.7 Hz, 1H), 3.24-3.00 (m, 2H), 2.85-2.68 (m, 1H), 2.33 (s, 3H), 1.69-1.54 (m, 4H), 1.46 (s, 9H), 1.43-1.06 (m, 2H).

The following compounds were prepared analogously:

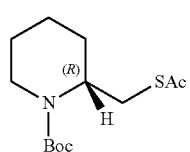

61b $^1$H NMR (CDCl$_3$ 300 MHz) δ 4.34 (s, 1H), 3.99 (d, J=11.8 Hz, 1H), 3.30-2.99 (m, 2H), 2.87-2.67 (m, 1H), 2.33 (s, 3H), 1.71-1.56 (m, 4H), 1.46 (s, 9H), 1.43-1.06 (m, 2H).

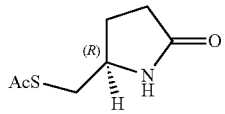

61c $^1$H NMR (CDCl$_3$ 300 MHz) δ 6.65 (br s, 1H), 3.94-3.75 (m, 1H), 3.14 (dd, J=13.9, 5.4 Hz, 1H), 2.94 (dd, J=13.9, 6.1 Hz, 1H), 2.49-2.16 (m, 6H), 1.88-1.66 (m, 1H).

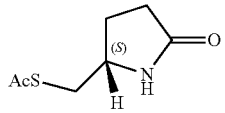

61d $^1$H NMR (CDCl$_3$ 300 MHz) δ 6.96 (br s, 1H), 3.95-3.73 (m, 1H), 3.13 (dd, J=13.8, 5.5 Hz, 1H), 2.96 (dd, J=13.8, 6.1 Hz, 1H), 2.50-2.17 (m, 6H), 1.92-1.68 (m, 1H).

Step 2

To a stirred solution of 0.104 g (0.38 mmol) of compound 61a and 0.150 g (0.25 mmol) of compound 23 in 2.5 mL of ethanol was added 0.026 g (0.38 mmol) of sodium ethoxide in 2.5 mL of ethanol. The reaction was heated at reflux and stirred overnight. After this time, the reaction was cooled to room temperature, concentrated, and the residue was partitioned between 10 mL of water and 10 mL of ethyl acetate. The aqueous layer was separated and extracted with two 15 mL portions of ethyl acetate. The combined organics were dried over anhydrous sodium sulfate, filtered, and concentrated. The residue was purified by flash chromatography (silica, 0-50% ethyl acetate/heptane) to afford 0.111 g (68%) of 62a as a white solid: MS: Calcd. for C$_{31}$H$_{38}$ClF$_2$NNaO$_6$S$_2$ (MNa$^+$), m/z=680.2. found 680.1. Retention time: 4.10 min.

The following compounds were prepared analogously:

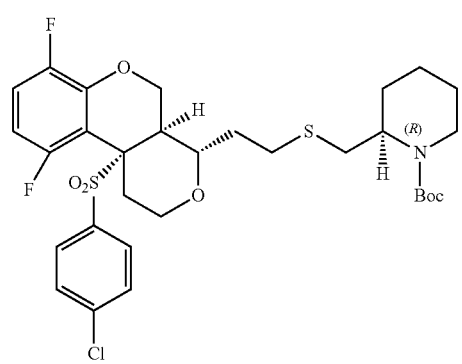

62b

MS: Calcd. for C$_{31}$H$_{38}$ClF$_2$NNaO$_6$S$_2$(MNa$^+$), m/z=680.2. found 680.3. Retention time: 4.01 min.

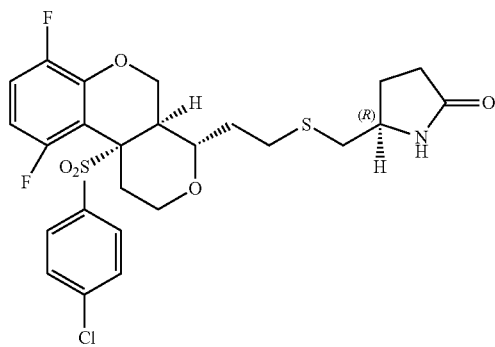

62c $^1$H NMR (CDCl$_3$ 300 MHz) δ 7.64 (d, J=8.7 Hz, 2H), 7.51 (d, J=8.8 Hz, 2H), 7.20-7.03 (m, 1H), 6.54-6.39 (m, 1H), 6.01 (s, 1H), 5.16 (dd, J=12.6, 2.6 Hz, 1H), 4.43 (d, J=12.3 Hz, 1H), 3.96-3.84 (m, 1H), 3.84-3.68 (m, 1H), 3.40-3.27 (m, 1H), 3.14 (t, J=11.5 Hz, 1H), 2.79-2.23 (m, 9H), 2.21-2.06 (m, 1H), 1.97-1.73 (m, 2H), 1.68 (s, 1H).

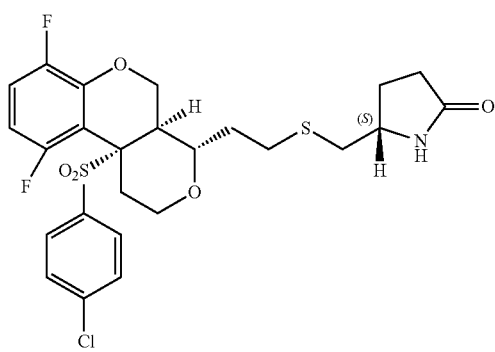

62d $^1$H NMR (CDCl$_3$ 300 MHz) δ 7.64 (d, J=8.6 Hz, 2H), 7.52 (d, J=8.8 Hz, 2H), 7.20-7.03 (m, 1H), 6.57-6.37 (m, 1H), 6.02 (s, 1H), 5.16 (dd, J=12.6, 2.6 Hz, 1H), 4.43 (d, J=12.4 Hz, 1H), 4.01-3.84 (m, 1H), 3.84-3.69 (m, 1H), 3.44-3.27 (m, 1H), 3.14 (t, J=11.5 Hz, 1H), 2.84-2.21 (m, 9H), 2.21-2.05 (m, 1H), 1.91-1.69 (m, 2H), 1.64 (s, 1H).

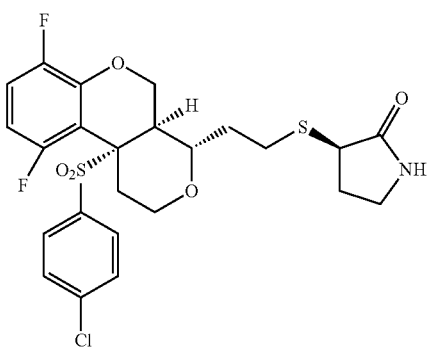

62e

MS: Calcd. for $C_{24}H_{24}ClF_2NNaO_5S_2$ (MNa$^+$), m/z=566.1. found 566.1. Retention time: 2.16 min.

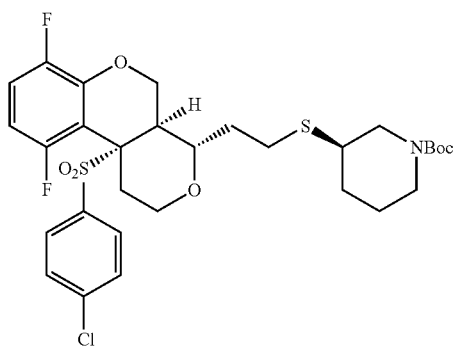

62f

MS: Calcd. for $C_{30}H_{36}ClF_2NNaO_6S_2$ (MNa$^+$), m/z=666.2. found 666.1. Retention time: 3.90 min.

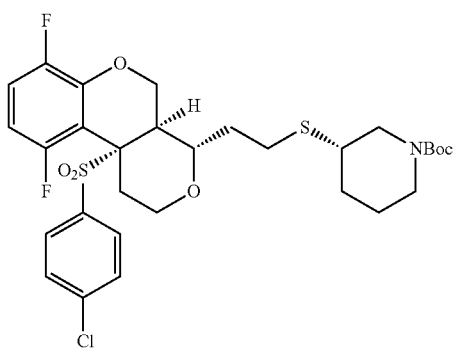

62g

MS: Calcd. for $C_{30}H_{36}ClF_2NNaO_6S_2$ (MNa$^+$), m/z=666.2. found 666.2. Retention time: 2.69 min.

Step 3

To a stirred solution of 0.111 g (0.17 mmol) of compound 62a in 10 mL of methylene chloride was added 0.117 g (0.68 mmol) of 3-chloroperbenzoic acid. The reaction was stirred at room temperature for 3 h. After this time, the reaction mixture was diluted with 20 mL of methylene chloride and washed with 20 mL of saturated aqueous sodium bicarbonate. The aqueous layer was separated and extracted with three 20 mL portions of methylene chloride. The combined organics were dried over anhydrous sodium sulfate, filtered, and concentrated to afford 0.123 g (98%) of 63a as a white solid: $^1$H NMR (CDCl$_3$ 300 MHz) δ 7.64 (d, J=8.6 Hz, 2H), 7.58-7.47 (m, 2H), 7.17-7.03 (m, 1H), 6.56-6.39 (m, 1H), 5.16 (dd, J=12.8, 2.4 Hz, 1H), 4.82 (s, 1H), 4.50 (d, J=12.6 Hz, 1H), 4.02 (s, 1H), 3.94-3.81 (m, 1H), 3.52-3.28 (m, 2H), 3.21-3.06 (m, 4H), 2.79-2.60 (m, 1H), 2.60-2.50 (m, 2H), 2.50-2.37 (m, 1H), 2.37-2.20 (m, 1H), 2.16-1.96 (m, 1H), 1.86 (t, J=14.2 Hz, 1H), 1.80-1.58 (m, 3H), 1.45 (s, 9H), 1.34-1.09 (m, 2H).

The following compounds were prepared analogously:

MS: Calcd. for $C_{31}H_{38}ClF_2NNaO_8S_2$ (MNa$^+$), m/z=712.2. found 712.2. Retention time: 3.50 min.

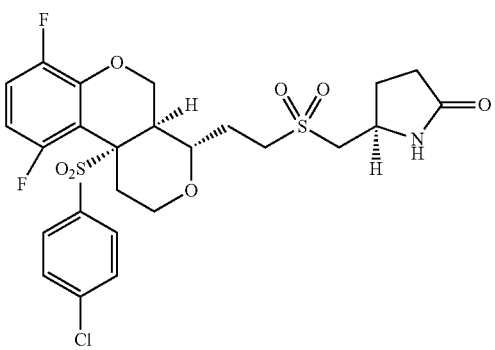

63c $^1$H NMR (CDCl$_3$ 300 MHz) δ 7.64 (d, J=8.6 Hz, 2H), 7.52 (d, J=8.7 Hz, 2H), 7.18-7.06 (m, 1H), 6.57-6.43 (m, 1H), 6.39 (s, 1H), 5.19 (dd, J=12.8, 2.5 Hz, 1H), 4.44 (d, J=12.9 Hz, 1H), 4.33-4.18 (m, 1H), 3.96-3.83 (m, 1H), 3.41-2.97 (m, 6H), 2.65-2.22 (m, 7H), 2.13-1.95 (m, 1H), 1.92-1.74 (m, 1H). MS: Calcd. for $C_{25}H_{26}ClF_2NNaO_7S_2$ (MNa$^+$), m/z=612.1. found 612.2. Retention time: 2.72 min. HPLC (Method 2) 97.8% (AUC), $t_R$=13.85 min. [α]25$_D$=−135.0° (c 0.150, Methylene Chloride).

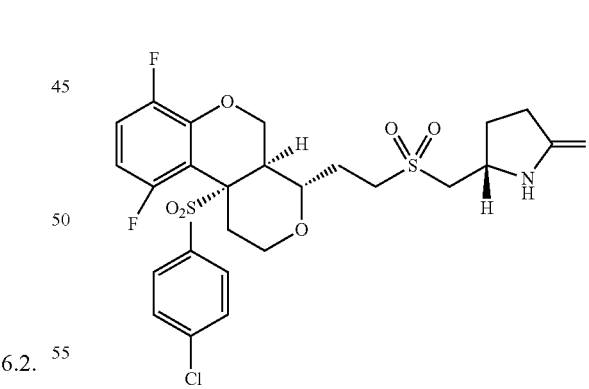

63d $^1$H NMR (CDCl$_3$ 300 MHz) δ 7.64 (d, J=8.6 Hz, 2H), 7.52 (d, J=8.7 Hz, 2H), 7.21-7.04 (m, 1H), 6.57-6.43 (m, 1H), 6.38 (s, 1H), 5.18 (dd, J=12.8, 2.5 Hz, 1H), 4.44 (d, J=12.7 Hz, 1H), 4.35-4.16 (m, 1H), 3.99-3.85 (m, 1H), 3.41-2.92 (m, 6H), 2.66-2.21 (m, 7H), 2.13-1.94 (m, 1H), 1.94-1.74 (m, 1H). MS: Calcd. for $C_{25}H_{27}ClF_2NO_7S_2$ (MH$^+$), m/z=590.1. found 590.3. Retention time: 2.72 min. HPLC (Method 2) 96.5% (AUC), $t_R$=13.86 min. [α]$^{25}$$_D$=−112.0° (c 0.150, Methylene Chloride).

63e

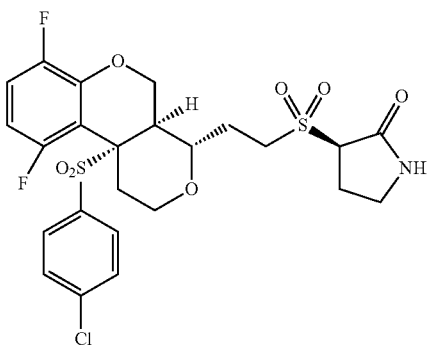

¹H NMR (DMSO-d₆ 500 MHz) δ 8.28 (s, 1H), 7.86-7.63 (m, 4H), 7.42 (td, J=9.5, 4.4 Hz, 1H), 6.75 (t, J=10.3 Hz, 1H), 4.93 (d, J=10.6 Hz, 1H), 4.66-4.48 (m, 1H), 4.27 (td, J=10.2, 6.5 Hz, 1H), 3.91 (d, J=10.1 Hz, 1H), 3.64-3.34 (m, 2H), 3.29-3.14 (m, 2H), 3.05 (t, J=11.7 Hz, 1H), 2.70-2.52 (m, 1H), 2.47-2.30 (m, 3H), 2.31-2.11 (m, 2H), 2.11-1.95 (m, 1H), 1.95-1.77 (m, 1H). MS: Calcd. for $C_{24}H_{24}ClF_2NNaO_7S_2$ (MNa⁺) m/z=598.0. found 597.9. Retention time: 2.80 min. HPLC (Method 2) 97.9% (AUC), $t_R$=14.24 min. $[\alpha]^{20}_D$=−82.5° (c 0.200, DMSO).

63f

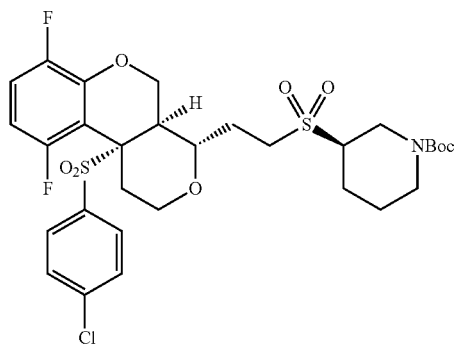

MS: Calcd. for $C_{30}H_{36}ClF_2NNaO_8S_2$ (MNa⁺), m/z=698.1. found 698.1. Retention time: 3.44 min.

63g

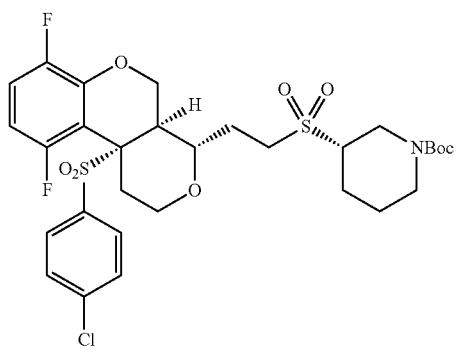

MS: Calcd. for $C_{30}H_{36}ClF_2NNaO_8S_2$ (MNa⁺), m/z=698.1. found 698.2. Retention time: 2.39 min.

Step 4

To a stirred solution of 0.123 g (0.18 mmol) of 63a in 10 mL of methylene chloride was added 0.13 mL (1.80 mmol) of TFA, and the reaction was stirred at room temperature for 14 h. After this time, the reaction was concentrated and the residue was purified by preparative HPLC (Method 1) to afford 0.058 g (55%) of 64a as an off-white solid: ¹H NMR (CD₃OD 300 MHz) δ 7.71 (d, J=8.8 Hz, 2H), 7.65 (d, J=8.8 Hz, 2H), 7.23 (td, J=9.6, 4.7 Hz, 1H), 6.65-6.48 (m, 1H), 5.13 (dd, J=12.8, 2.6 Hz, 1H), 4.57 (d, 12.7 Hz, 1H), 4.03-3.90 (m, 1H), 3.82 (br s, 1H), 3.58 (dd, J=14.8, 4.7 Hz, 1H), 3.51-3.34 (m, 4H), 3.35-3.27 (m, 1H), 3.26-3.00 (m, 2H), 2.59 (t, J=12.4 Hz, 2H), 2.53-2.25 (m, 2H), 2.19-1.96 (m, 2H), 1.90 (d, J=9.8 Hz, 2H), 1.81-1.58 (m, 3H). MS: Calcd. for $C_{26}H_{31}ClF_2NO_6S_2$ (MH⁺), m/z=590.1. found 590.1. Retention time: 2.18 min. HPLC (Method 2) >99% (AUC), $t_R$=11.92 min. $[\alpha]^{25}_D$=−226.0° (c 0.100, Methylene Chloride).

The following compounds were prepared analogously:

64b

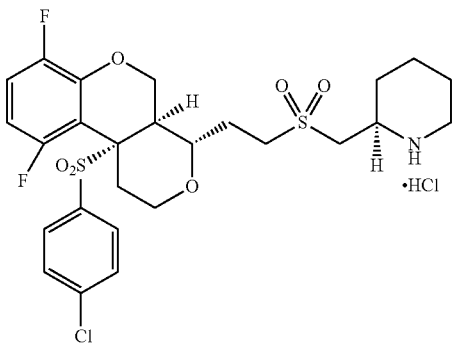

¹H NMR (CD₃OD 300 MHz) δ 7.71 (d, J=8.8 Hz, 2H), 7.64 (d, J=8.9 Hz, 2H), 7.34-7.15 (m, 1H), 6.67-6.50 (m, 1H), 5.13 (dd, J=12.8, 2.7 Hz, 1H), 4.55 (d, J=12.7 Hz, 1H), 4.01-3.87 (m, 1H), 3.81 (br s, 1H), 3.58 (dd, J=14.9, 4.5 Hz, 1H), 3.51-3.34 (m, 4H), 3.34-3.25 (m, 1H), 323-2.98 (m, 2H), 2.58 (t, J=12.2 Hz, 2H), 2.53-2.40 (m, 1H), 2.34 (dd, J=16.9, 7.2 Hz, 1H), 2.17-1.96 (m, 2H), 1.96-1.79 (m, 2H), 1.77-1.53 (m, 3H). MS: Calcd. for $C_{26}H_{31}ClF_2NO_6S_2$ (MH⁺), m/z=590.1. found 590.1. Retention time: 2.16 min. HPLC (Method 2) >99% (AUC), $t_R$=11.98 min. $[\alpha]^{25}_D$=−158.0° (c 0.100, Methylene Chloride).

64c

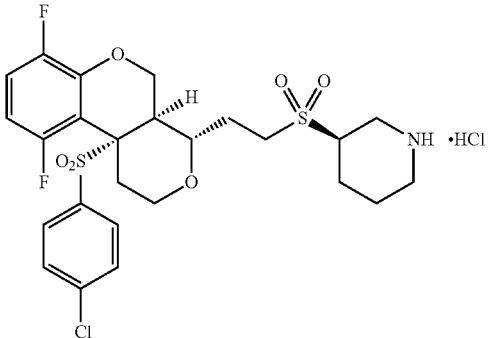

¹H NMR (DMSO-d₆ 500 MHz) δ 7.82-7.68 (m, 4H), 7.49-7.35 (m, 1H), 6.81-6.72 (m, 1H), 4.93 (dd, J=12.8, 2.6 Hz, 1H), 4.58 (d, J=12.6 Hz, 1H), 3.99-3.88 (m, 1H), 3.69-3.55 (m, 2H), 3.40 (s, 1H), 3.35-3.15 (m, 4H), 3.08-2.94 (m, 2H), 2.88 (s, 1H), 2.60-2.52 (m, 1H), 2.44 (d, J=10.2 Hz, 1H), 2.33-2.22 (m, 1H), 2.22-2.04 (m, 2H), 1.97-1.85 (m, 2H), 1.81-1.59 (m, 2H). MS: Calcd. for $C_{25}H_{29}ClF_2NO_6S_2$ (MH$^+$), m/z=576.1. found 576.0. HPLC (Method 2) >99% (AUC), $t_R$=11.76 min. $[\alpha]^{20}_D$=−93.2° (c 0.250, DMSO).

64d

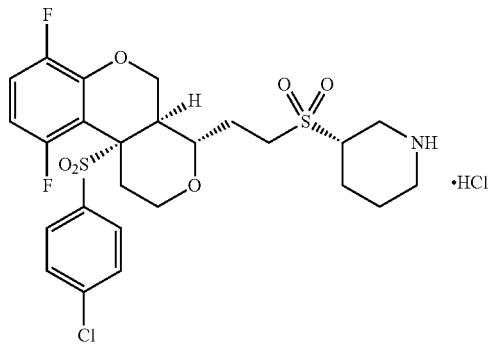

$^1$H NMR (DMSO-d$_6$ 500 MHz) δ 9.18 (s, 2H), 7.81-7.63 (m, 4H), 7.42 (td, J=9.7, 4.7 Hz, 1H), 6.81-6.70 (m, 1H), 4.93 (dd, J=12.8, 2.6 Hz, 1H), 4.57 (d, J=12.6 Hz, 1H), 3.99-3.85 (m, 1H), 3.65-3.50 (m, 2H), 3.31-3.18 (m, 3H), 3.08-2.93 (m, 2H), 2.94-2.80 (m, 1H), 2.59-2.51 (m, 1H), 2.45 (d, J=10.1 Hz, 1H), 2.31-2.06 (m, 3H), 2.02-1.86 (m, 2H), 1.79-1.60 (m, 2H). MS: Calcd. for $C_{25}H_{29}ClF_2NO_6S_2$ (MH$^+$), m/z=576.1. found 576.0. Retention time: 2.15 min. HPLC (Method 2) >99% (AUC), $t_R$=11.78 min.

SCHEME 28

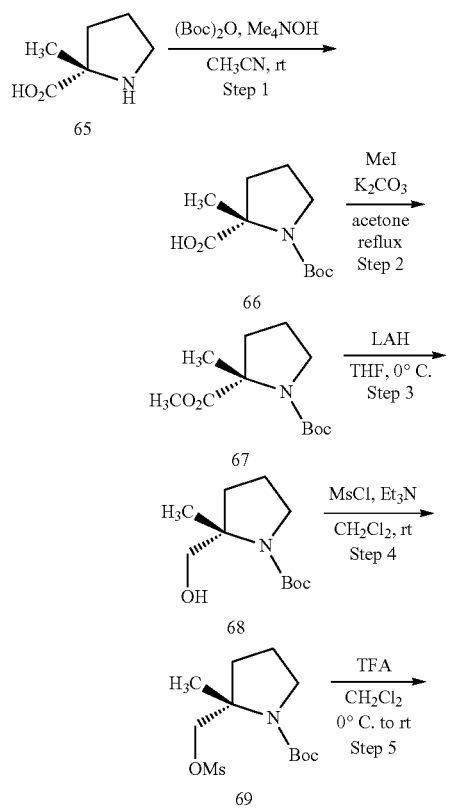

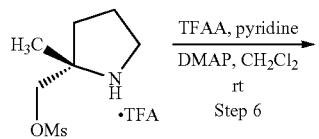

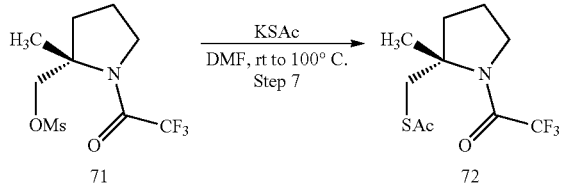

Step 1

To a solution of 2.00 g (15.5 mmol) of compound 65 in 150 mL of acetonitrile was added 14 mL (15.5 mmol) of tetramethylammonium hydroxide and 5.10 g (23.2 mmol) of di-tert-butyldicarbonate and the mixture was stirred at room temperature for 2 days. After this time, another portion of di-tert-butyldicarbonate (2.50 g, 11.5 mmol) was added and the mixture was stirred at room temperature for an additional 24 h. After this time, the third portion of di-tert-butyldicarbonate (2.50 g, 11.5 mmol) was added and the mixture was stirred at room temperature for 24 h. After this time, the mixture was concentrated, and partitioned between 200 mL of 1 N hydrochloric acid and 200 mL of methylene chloride. The aqueous layer was separated and extracted with three 100 mL portions of methylene chloride. The combined organics were dried over anhydrous magnesium sulfate, filtered, and concentrated to afford 3.60 g of crude 66, which was used in the subsequent step without further purification: MS: Calcd. for $C_7H_{12}NO_4$ (MH$^+$—$C_4H_8$), m/z=174.1. found 174.2. Retention time: 2.22 min.

Step 2

A mixture of 3.60 g (20.7 mmol) of crude 66, 2.40 g (17.3 mmol) of potassium carbonate and 1.1 mL (17.3 mmol) of iodomethane in 80 mL of acetone was heated at reflux overnight. The reaction mixture was cooled to room temperature, filtered and concentrated. The residue was partitioned between 50 mL of saturated aqueous ammonium chloride and 50 mL of methylene chloride. The aqueous layer was separated and extracted with three 15 mL portions of methylene chloride. The combined organics were dried over anhydrous magnesium sulfate, filtered, and concentrated to afford 3.65 g of crude 67, which was used in the subsequent step without further purification: MS: Calcd. for $C_8H_{14}NO_4$ (MH$^+$—$C_4H_8$), m/z=188.1. found 188.3. Retention time: 3.35 min.

Step 3

To a solution of 3.65 g of crude 67 in 75 mL of THF was added 0.850 g (22.5 mmol) of lithium aluminium hydride and the mixture was stirred at 0° C. under nitrogen for 30 min. After this time, 1 mL of methanol was added slowly, then 10 mL of water. The resulting mixture was extracted with three 10 mL portions of methylene chloride. The combined organics were dried over anhydrous magnesium sulfate, filtered, and concentrated to afford 3.23 g of crude 68, which was used in the subsequent step without further purification: MS: Calcd. for $C_7H_{14}NO_3$ (MH$^+$—$C_4H_8$), m/z=160.1. found 160.2. Retention time: 1.21 min.

Step 4

To a solution of 3.07 g of crude 68 and 4 mL (28.5 mmol) of triethylamine in 70 mL of methylene chloride was added 1.7 mL (21.4 mmol) of methanesulfonyl chloride at 0° C. The mixture was warmed to room temperature and stirred overnight under nitrogen. After this time, the reaction mixture was poured into 20 mL of water and the layers were separated. The aqueous layer was extracted with three 20 mL portions of methylene chloride. The combined organics were washed with 15 mL of 1 N hydrochloric acid and 20 mL of brine, dried over anhydrous magnesium sulfate, filtered, and concentrated to afford crude 69 (4.18 g) which was used in the subsequent step without further purification: MS: Calcd. for $C_8H_{16}NO_5S$ ($MH^+$—$C_4H_8$), m/z=238.1. found 238.0. Retention time: 2.75 min.

Step 5

To a solution of 4.40 g of crude 69 in 75 mL of methylene chloride was added 7.5 mL of trifluoroacetic acid and the mixture was stirred at room temperature for 30 min. After this time, 50 mL of saturated aqueous sodium bicarbonate was added slowly and the layers were separated. The aqueous layer was extracted with three 15 mL portions of methylene chloride. The combined organics were dried over anhydrous magnesium sulfate, filtered, and concentrated to afford 4.36 g of crude 70, which was used in the subsequent step without further purification: MS: Calcd. for $C_7H_{16}NO_3S$ ($MH^+$), m/z=194.1. found 194.1. Retention time: 0.47 min.

Step 6

To a stirred solution of 2.18 g of crude 70 in 75 mL of methylene chloride was added 5.4 mL (18.8 mmol) of trifluoroacetic anhydride, 2.1 mL (26.3 mmol) of pyridine, and 4-dimethylaminopyridine (catalytic). The reaction was stirred at room temperature overnight. After this time, the reaction was diluted with 20 mL of methylene chloride and washed with 20 mL of 1 N sodium hydroxide. The aqueous layer was extracted with three 20 mL portions of methylene chloride. The combined organics were dried over anhydrous sodium sulfate, filtered, and concentrated. The residue was dissolved in 25 mL of ethyl acetate and washed with 50 mL of 5% aqueous lithium chloride and 50 mL of brine. The organic layer was separated and dried over anhydrous sodium sulfate, filtered, and concentrated to afford 1.82 g (84% over 7 steps) of 71: MS: Calcd. for $C_9H_{15}F_3NO_4S$ ($MH^+$), m/z=290.1. found 290.0. Retention time: 2.51 min.

Step 7

A solution of 0.91 g (3.15 mmol) of compound 71 and 0.90 g (7.86 mmol0 of potassium thioacetate in 15 mL of DMF was heated at 100° C. for 1 h. After this time, the reaction mixture was cooled to room temperature and diluted with 15 mL of saturated aqueous ammonium chloride and 10 mL of water, and the layers were separated. The aqueous layer was extracted with four 15 mL portions of methylene chloride. The combined organics were washed with two 10 mL portions of water and 10 mL of brine, dried over anhydrous magnesium sulfate, filtered, and concentrated. The residue was purified by flash chromatography (silica, 0-40% ethyl acetate/heptane) to afford 0.32 g (38%) of 72: MS: Calcd. for $C_{10}H_{15}F_3NO_2S$ ($MH^+$), m/z=270.1. found 270.0. Retention time: 2.12 min.

SCHEME 29

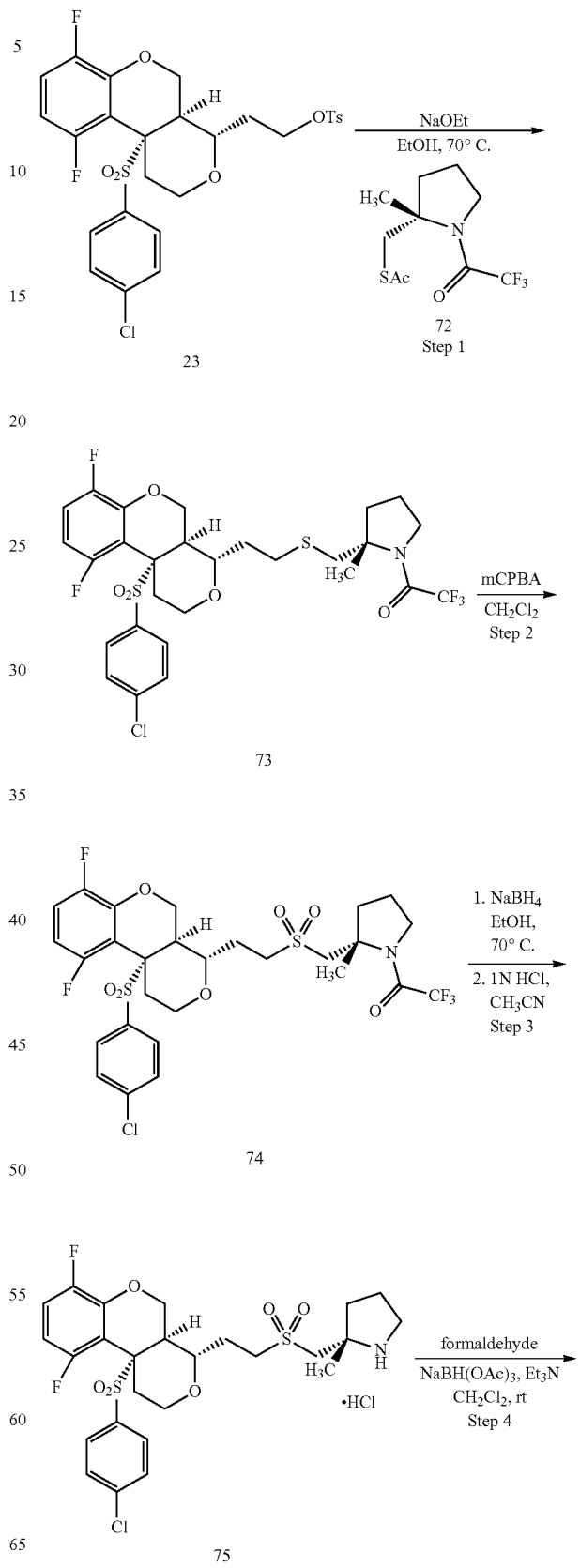

76a

Step 1

A mixture of 0.14 g (0.52 mmol) of compound 72, and 0.06 g (2.60 mmol) of sodium ethoxide in 6 mL of ethanol was stirred at room temperature for 30 min. After this time, 0.312 g (0.52 mmol) of compound 23 was added and the reaction mixture was heated at 70° C. for 2 h. The reaction mixture was cooled to room temperature, concentrated, and partitioned between 50 mL of saturated aqueous ammonium chloride and 50 mL of methylene chloride. The aqueous layer was extracted with three 15 mL portions of methylene chloride. The combined organics were dried over anhydrous magnesium sulfate, filtered, and concentrated. The residue was purified by flash chromatography (silica, 0-50% ethyl acetate/heptane) to afford 0.235 g (69%) of 73 as a white solid: MS: Calcd. for $C_{28}H_{33}ClF_5N_2O_3S_2$ (MNH$_4^+$), m/z=671.1. found 671.2. Retention time: 2.64 min.

Step 2

To a stirred solution of 0.235 g (0.359 mmol) of compound 73 in 7.2 mL of methylene chloride was added 0.31 g (1.80 mmol) of 3-chloroperbenzoic acid (mCPBA) and the mixture was stirred at room temperature for 3 h. After this time, the reaction was quenched with 20 mL of saturated aqueous sodium bicarbonate. The layers were separated and the aqueous layer was extracted with three 15 mL portions of methylene chloride. The combined organics were dried over anhydrous magnesium sulfate, filtered, and concentrated. The residue was purified by flash chromatography (silica, 0-20% ethyl acetate/heptane) to afford 0.23 g (93%) of 74 as a white solid: MS: Calcd. for $C_{28}H_{33}ClF_5N_2O_7S_2$ (MNH$_4^+$), m/z=703.1. found 703.2. Retention time: 2.41 min.

Step 3

To a stirred solution of 0.23 g (0.335 mmol) of compound 74 in 3.4 mL of ethanol was added 0.076 g (2.01 mmol) of sodium borohydride and the mixture was heated at reflux for 1 h. After this time, the reaction mixture was cooled to room temperature, diluted with 15 mL of saturated aqueous ammonium chloride and 10 mL of water, and the layers were separated. The aqueous layer was extracted with four 15 mL portions of methylene chloride. The combined organics were washed with two 10 mL portions of water and 10 mL of brine, dried over anhydrous magnesium sulfate, filtered, and concentrated. The residue was purified by flash chromatography (silica, 0-10% methanol/methylene chloride) and then lyophilized (CH$_3$CN/1 N HCl) to afford 0.137 g (65%) of 75 as a white solid: $^1$H NMR (DMSO-d$_6$ 500 MHz) 7.84-7.60 (m, 4H), 7.42 (td, J=9.9, 4.7 Hz, 1H), 6.84-6.63 (m, 1H), 5.08-4.80 (m, 1H), 4.61 (d, J=13.0 Hz, 1H), 3.92 (d, J=13.6 Hz, 1H), 3.87-3.63 (m, 2H), 3.51-3.14 (m, 6H), 3.04 (t, J=11.8 Hz, 1H), 2.64-2.52 (m, 1H), 2.41 (d, J=10.2 Hz, 1H), 2.38-2.21 (m, 1H), 2.17 (t, J=11.8 Hz, 1H), 2.08-1.77 (m, 5H), 1.52 (s, 3H). MS: Calcd. for $C_{26}H_{31}ClF_2NO_6S_2$ (MH$^+$), m/z=590.1. found 590.0. HPLC (Method 2) >99% (AUC), t$_R$=11.67 min. $[\alpha]^{20}_D$=−77.6° (c 0.250, DMSO).

Step 4

A solution of 0.08 g (0.128 mmol) of compound 75, 10 µL (0.128 mmol) of formaldehyde (37% wt. in water), 0.038 g (0.18 mmol) of sodium triacetoxy borohydride, and 10 µL (0.128 mmol), triethylamine in 1.3 mL of methylene chloride was stirred at room temperature for 2 h. The reaction was then quenched with 5 mL of saturated aqueous sodium bicarbonate and extracted with three 10 mL portions of methylene chloride. The combined extracts were dried over anhydrous magnesium sulfate, filtered, and concentrated. The residue was lyophilized (H$_2$O/HCl/CH$_3$CN) to afford 0.0609 g (93%) of 76a as an off-white solid: $^1$H NMR (DMSO-d$_6$ 500 MHz) 7.83-7.67 (m, 4H), 7.52-7.33 (m, 1H), 6.85-6.69 (m, 1H), 4.93 (dd, J=12.9, 2.8 Hz, 1H), 4.59 (d, J=12.9 Hz, 1H), 3.96-3.85 (m, 1H), 3.77 (d, J=13.2 Hz, 1H), 3.72-3.46 (m, 3H), 3.38-2.99 (m, 5H), 2.71-2.58 (m, 3H), 2.54 (d, J=13.9 Hz, 1H), 2.42 (d, J=10.2 Hz, 1H), 2.33 (t, J=16.6 Hz, 1H), 2.24-2.10 (m, 2H), 2.10-1.84 (m, 3H), 1.66 (s, 1H), 1.40 (s, 2H). MS: Calcd. for $C_{27}H_{33}ClF_2NO_6S_2$ (MH$^+$), m/z=604.1. found 604.0. HPLC (Method 2) 99.0% (AUC), t$_R$=11.96 min. $[\alpha]^{20}_D$=−81.0° (c 0.210, DMSO).

The following compound was prepared analogously:

76b $^1$H NMR (DMSO-d$_6$ 500 MHz) δ 7.75 (br s, 4H), 7.42 (br s, 1H), 6.76 (br s, 1H), 4.93 (d, J=11.2 Hz, 1H), 4.58 (d, J=12.7 Hz, 1H), 3.93 (d, J=8.1 Hz, 1H), 3.77 (d, J=7.8 Hz, 1H), 3.66 (br s, 1H), 3.32-3.16 (m, 5H), 3.18-2.97 (m, 2H), 2.92 (br s, 1H), 2.80 (s, 3H), 2.46-2.36 (m, 1H), 2.29 (br s, 1H), 2.24-2.04 (m, 2H), 2.00-1.24 (m, 4H). MS: Calcd. for $C_{26}H_{31}ClF_2NO_6S_2$ (MH$^+$), m/z=590.1. found 590.1. Retention time: 2.14 min. HPLC (Method 2) >99 (AUC), t$_R$=11.89 min. $[\alpha]^{25}_D$=−100.5° (c 0.420, DMSO).

SCHEME 30

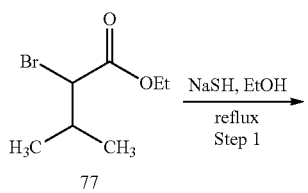

77

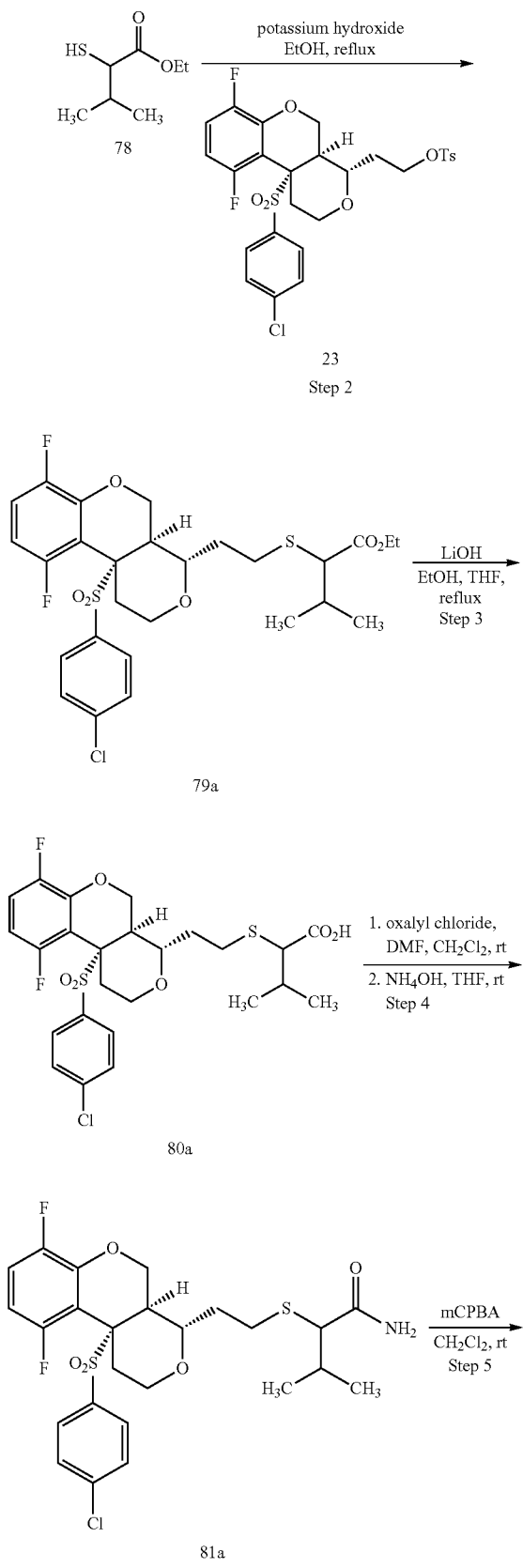

23
Step 2

79a

80a

81a

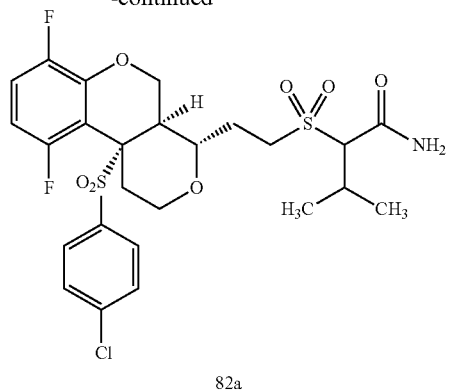

82a

Step 1

To a stirred solution of 0.25 g (1.20 mmol) of compound 77 in 20 mL of ethanol at room temperature under nitrogen was added 0.336 g (6.00 mmol) of sodium hydrogen sulfide. The reaction mixture was heated at reflux for 30 min and then cooled to room temperature. The reaction mixture was concentrated and the residue was partitioned between 20 mL of ethyl acetate and 20 mL of water. The layers were separated and the aqueous layer was extracted with two 15 mL portions of ethyl acetate. The combined organics were dried over anhydrous sodium sulfate, filtered, and concentrated to afford 0.195 g (100%) of crude 78 as an oil, which was used in the subsequent step without further purification.

Step 2

To a stirred solution of 0.195 g (1.20 mmol) of compound 78 and 1.20 mL (1 M in ethanol, 1.20 mmol) of potassium hydroxide in 5 mL of ethanol was added 0.24 g (0.40 mmol) of compound 23. The reaction mixture was stirred for 10 min at room temperature under nitrogen and then heated at reflux for 1 h. The reaction was cooled to room temperature and concentrated. The residue was partitioned between 15 mL of water and 15 mL of ethyl acetate. The layers were separated and the aqueous layer was extracted with two 15 mL portions of ethyl acetate. The combined organics were dried over anhydrous sodium sulfate, filtered, and concentrated. The residue was purified by flash chromatography (silica, 0-40% ethyl acetate/heptane) to afford 0.114 g (48%) of 79a as a clear foam: MS: Calcd. $C_{27}H_{31}ClF_2NaO_6S_2$ (MNa$^+$), m/z=611.1; found 611.1. Retention time: 3.85 min.

The following compounds were prepared analogously:

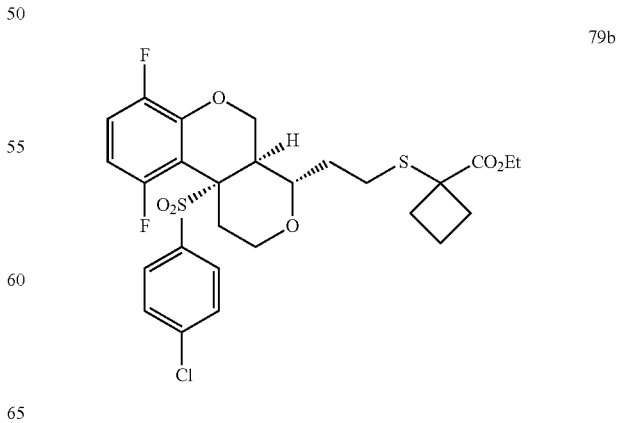

79b

MS: Calcd. for $C_{27}H_{29}ClF_2NaO_6S_2$ (MNa$^+$), m/z=609.1. found 609.0. Retention time: 3.75 min.

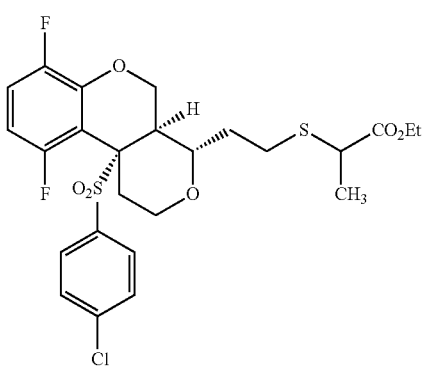

MS: Calcd. for $C_{25}H_{31}ClF_2NO_6S_2$ ($MNH_4^+$), m/z=578.1. found 578.2. Retention time: 2.56 min.

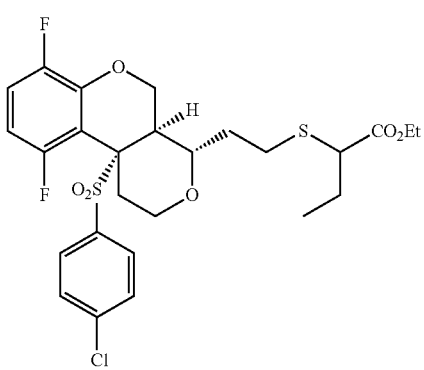

MS: Calcd. $C_{26}H_{29}ClF_2NaO_6S_2$ ($MNa^+$), m/z=597.1. found 597.2. Retention time: 2.65 min.

Step 3

To a stirred solution of 0.114 g (0.190 mmol) of compound 79a in 7 mL of ethanol and 7 mL of THF was added a solution of 0.041 g (0.98 mmol) of lithium hydroxide in 6 mL of water at room temperature. The reaction was heated at reflux for 24 h, cooled to room temperature, and concentrated. The residue was acidified to pH 1 with 1 N hydrochloric acid and extracted with three 20 mL portions of ethyl acetate. The combined organics were dried over anhydrous sodium sulfate, filtered, and concentrated to afford 0.106 g (99%) of 80a as a clear colorless film: MS: Calcd. for $C_{25}H_{27}ClF_2NaO_6S_2$ ($MNa^+$), m/z=583.1. found 583.1. Retention time: 3.31 min.

The following compounds were prepared analogously:

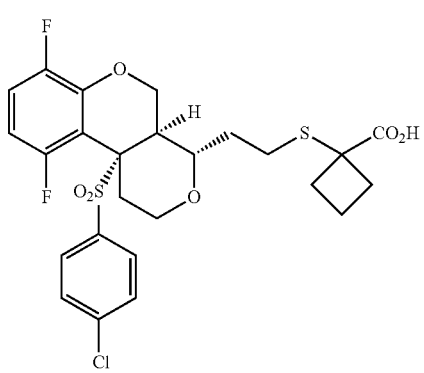

MS: Calcd. for $C_{25}H_{25}ClF_2NaO_6S_2$ ($MNa^+$), m/z=581.1. found 580.9. Retention time: 3.27 min.

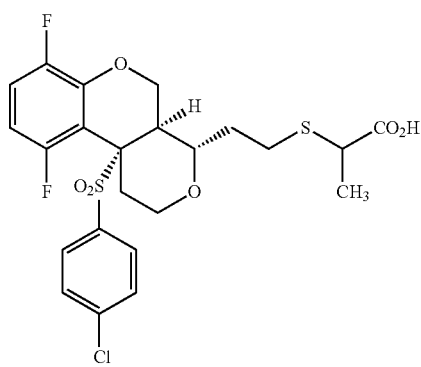

MS: Calcd. for $C_{23}H_{27}ClF_2NO_6S_2$ ($MNH_4^+$), m/z 550.1. found 550.2. Retention time: 2.26 min.

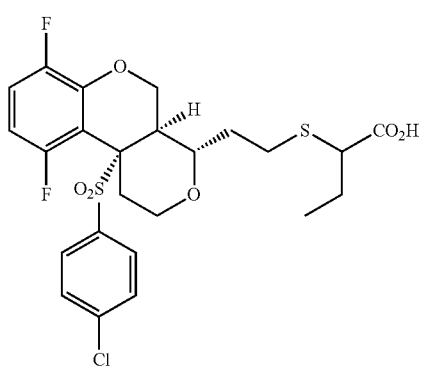

MS: Calcd. for $C_{24}H_{25}ClF_2NaO_6S_2$ ($MNa^+$), m/z=569.1. found 569.1. Retention time: 2.31 min.

Step 4

To a stirred solution of 0.106 g (0.19 mmol) of compound 80a in 0.01 mL of DMF and 10 mL of methylene chloride was slowly added 0.05 mL (0.57 mmol) of oxalyl chloride under nitrogen at room temperature. After 1 h, the reaction was concentrated and the residue was dissolved in 10 mL of THF. Concentrated ammonium hydroxide (0.650 mL, 9.50 mmol) was added and the reaction mixture was stirred for 15 h at room temperature. The reaction mixture was then partitioned between 10 mL of water and 10 mL of ethyl acetate. The layers were separated and the aqueous layer was extracted with two 25 mL portions of ethyl acetate. The combined organics were dried over anhydrous sodium sulfate, filtered, and concentrated to afford 0.106 g of crude 81a, which was used without further purification: MS:

Calcd. for $C_{25}H_{28}ClF_2NNaO_5S_2$($MNa^+$), m/z=582.1. found 582.0. Retention time: 3.06 min.

The following compounds were prepared analogously:

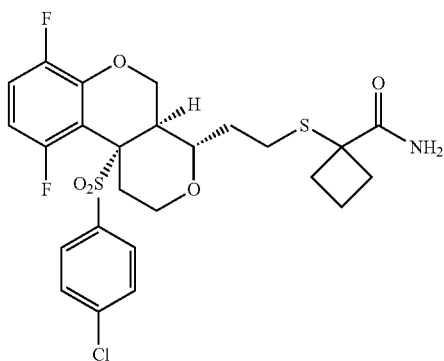
81b

MS: Calcd. for $C_{25}H_{26}ClF_2NNaO_5S_2$ (MNa$^+$), m/z=580.1. found 579.9. Retention time: 3.08 min.

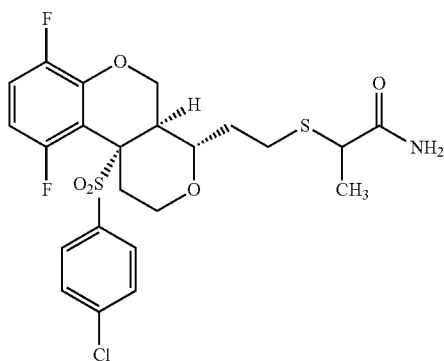
81c

MS: Calcd. for $C_{23}H_{24}ClF_2NNaO_5S_2$ (MNa$^+$), m/z=554.1. found 554.1. Retention time: 2.12 min,

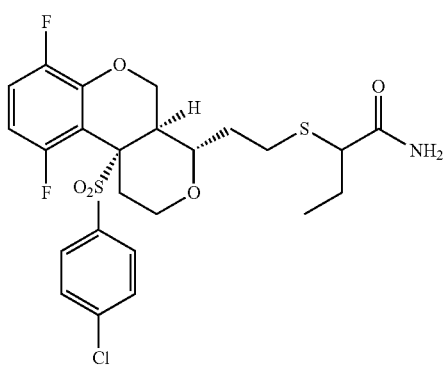
81d

MS: Calcd. for $C_{24}H_{26}ClF_2NNaO_5S_2$ (MNa$^+$), m/z=568.1. found 568.1. Retention time: 2.16 min.

Step 5

To a stirred solution of 0.106 g of crude 81a in 10 mL of methylene chloride was added 0.132 g (0.76 mmol) of 3-chloroperbenzoic acid (mCPBA) at room temperature. The reaction mixture was stirred for 16 h and then quenched with 20 mL of saturated aqueous sodium bicarbonate and 2 g of sodium thiosulfate. The mixture was stirred for 1 h after which time the layers were separated and the aqueous layer was extracted with three 15 mL portions of methylene chloride. The combined organics were dried over anhydrous sodium sulfate, filtered, and concentrated. The residue was purified by flash chromatography (0-5% methanol/methylene chloride) to afford 0.061 g (54% over two steps) of 82a as an off-white solid: $^1$H NMR (CDCl$_3$, 300 MHz) δ 7.64 (d, J=8.5 Hz, 2H), 7.52 (d, J=8.6 Hz, 2H), 7.11 (td, J=9.5, 4.8 Hz, 1H), 6.59-6.40 (m, 2H), 5.65 (br s, 1H), 5.17 (dd, J=12.8, 2.5 Hz, 1H), 4.46 (d, J=12.6 Hz, 1H), 3.95-3.79 (m, 1H), 3.55-3.24 (m, 3H), 3.24-2.96 (m, 2H), 2.72-2.36 (m, 4H), 2.28 (t, J=12.4 Hz, 1H), 2.19-1.91 (m, 1H), 1.25 (dd, J=6.7, 1.3 Hz, 3H), 1.16 (dd, J=6.7, 2.6 Hz, 3H). MS: Calcd. for $C_{25}H_{28}ClF_2NNaO_7S_2$ (MNa$^+$), m/z=614.1. found 614.0. Retention time: 2.91 min. HPLC (Method 2) 96.5% (AUC), $t_R$=14.97 min. [α]$^{25}_D$=−196.0° (c 0.100, Methylene Chloride).

The following compounds were prepared analogously:

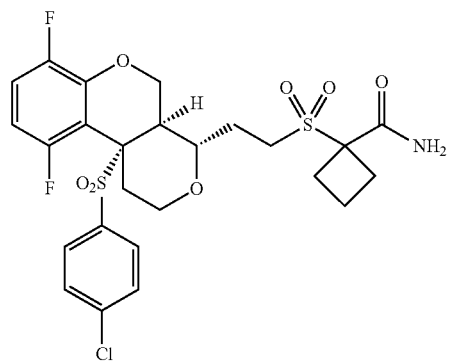
82b $^1$H NMR (CDCl$_3$, 500 MHz) δ 7.63 (d, J=8.6 Hz, 2H), 7.51 (d, J=8.8 Hz, 2H), 7.10 (td, J=9.4, 4.7 Hz, 1H), 6.54-6.40 (m, 2H), 5.55 (s, 1H), 5.16 (dd, J=12.7, 2.6 Hz, 1H), 4.44 (d, J=12.6 Hz, 1H), 3.97-3.76 (m, 1H), 3.32 (td, J=9.7, 2.8 Hz, 1H), 3.25-3.14 (m, 1H), 3.10 (t, J=11.6 Hz, 1H), 2.99-2.88 (m, 1H), 2.88-2.75 (m, 2H), 2.75-2.60 (m, 2H), 2.53 (t, J=11.0 Hz, 2H), 2.46-2.36 (m, 1H), 2.35-2.21 (m, 1H), 2.19-1.93 (m, 3H). MS: Calcd. for $C_{25}H_{26}ClF_2NNaO_7S_2$ (MNa$^+$), m/z=612.1. found 612.0. Retention time: 2.90 min. HPLC (Method 2) 97.1% (AUC), $t_R$=14.92 min. [α]$^{25}_D$=−155.0° (c 0.100, Methylene Chloride).

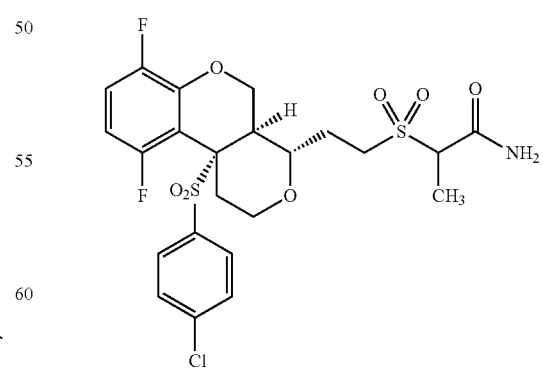
82c $^1$H NMR (CDCl$_3$, 500 MHz) δ 7.63 (d, J=8.4 Hz, 2H), 7.51 (d, J=8.5 Hz, 2H), 7.13-7.08 (m, 1H), 6.50-6.40 (m, 2H), 5.57 (br s, 1H), 5.17 (d, J=11.4 Hz, 1H), 4.45 (d, J=12.6 Hz, 1H), 3.90-3.74 (m, 2H), 3.38-3.31 (m, 2H), 3.15-3.03 (m, 2H), 2.57-2.38 (m, 3H), 2.31-2.26 (m, 1H), 2.10-2.00 (m, 1H), 1.65 (d, J=7.2 Hz, 3H). MS: Calcd. for $C_{23}H_{25}ClF_2NO_7S_2$ (MH+), m/z=564.1. found 564.1. HPLC (Method 2) 98.8% (AUC), $t_R$=14.07 min. $[\alpha]^{23}_D$=−135.0° (c 0.090, Methanol).

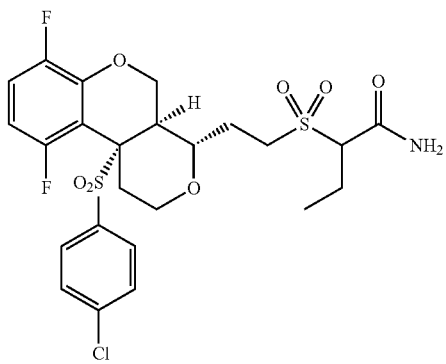

82d $^1$H NMR (CDCl$_3$ 500 MHz) δ 7.63 (d, J=8.5 Hz, 2H), 7.51 (d, J=8.7 Hz, 2H), 7.11 (td, J=9.4, 4.7 Hz, 1H), 6.50-6.45 (m, 1H), 6.31-6.28 (m, 1H), 5.58 (br s, 1H), 5.16 (dd, J=12.7, 2.5 Hz, 1H), 4.45 (d, J=12.8 Hz, 1H), 3.90-3.87 (m, 1H), 3.53 (td, J 10.9, 3.7 Hz, 1H), 3.39-3.35 (m, 2H), 3.14-3.06 (m, 2H), 2.56-2.52 (m, 2H), 2.50-2.43 (m, 1H), 2.31-2.27 (m, 1H), 2.22-2.17 (m, 1H), 2.08-2.01 (m, 2H), 1.12-1.08 (m, 3H); MS: Calcd. for $C_{24}H_{26}ClF_2NNaO_7S_2$ (MNa+), m/z=600.1. found 599.9. Retention time: 2.83 min. HPLC (Method 2) 98.6% (AUC), $t_R$=14.43 min. $[\alpha]^{23}_D$=381.0° (c 0.03, Methanol).

J=8.8 Hz, 2H), 7.10 (m, 1H), 6.47 (m, 1H), 5.17 (dd, J=12.8, 2.4 Hz, 1H), 4.42 (d, J=12.8 Hz, 1H), 3.90 (m, 1H), 3.45 (m, 4H), 3.35 (m, 2H), 3.10 (m, 2H), 3.05 (s, 3H), 2.40-2.60 (m, 3H), 2.30 (m, 1H), 2.05 (m, 1H). LCMS: Calcd. for $C_{23}H_{26}ClF_2O_8S_3$, 599.1 (MH+). found 599.3. Retention time: 4.24/7.5 min.

Step 2

To a suspension of 0.07 g (0.14 mmol) of compound 28 in 5 mL of anhydrous methanol was added 0.05 g (0.71 mmol) of potassium methoxide at room temperature. After 15 min., 0.03 g (0.31 mmol) of methyl chloromethylsulfide was added, and the stirring was continued for additional 3 h. It was concentrated; the residue was dissolved in 15 mL of dichloromethane. To the solution was added 0.40 g (70%, 1.62 mmol) of 3-chloroperoxybenzoic acid (mCPBA), the mixture was stirred at room temperature for 2 h. It was quenched with 10 mL of 10% sodium thiosulfate solution, 25 mL of saturated sodium bicarbonate. The mixture was extracted with two 40 mL portions of dichloromethane. The combined organic layers were concentrated; the residue was purified by chromatography eluting with a gradient of 0 to 4% methanol in dichloromethane plus 1% ammonium hydroxide to give 0.044 g of compound 84. $^1$H NMR (CDCl$_3$ 400 MHz) δ 7.62 (d, J=8.4 Hz, 2H), 7.50 (d, J=8.8 Hz, 2H), 7.10 (m, 1H), 6.48 (m, 1H), 5.17 (dd, J=12.8, 2.4 Hz, 1H), 4.38-4.52 (m, 3H), 3.90 (m, 1H), 3.65 (m, 1H), 3.40 (m, 2H), 3.20 (s, 3H), 3.12 (m, 1H), 2.40-2.60 (m, 3H), 2.30 (m, 1H), 2.10 (m, 1H). LCMS: Calcd. for $C_{22}H_{24}ClF_2O_8S_3$, 585.0 (MH+). found 585.3. Retention time: 4.47/7.5 min.

SCHEME 31

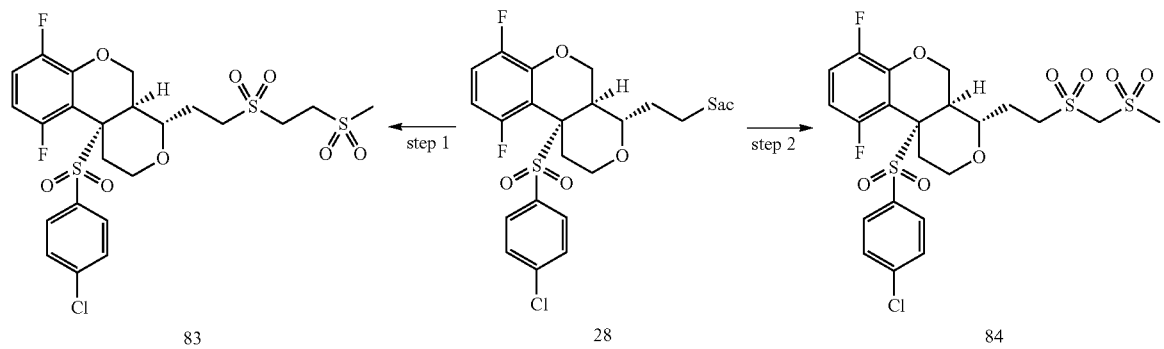

83     28     84

Step 1

To a suspension of 0.08 g (0.16 mmol) of compound 28 in 6 mL of anhydrous methanol was added 0.05 g (0.71 mmol) of potassium methoxide at room temperature. After 10 min., 0.03 g (0.28 mmol) of methyl vinylsulfone was added, and the stirring was continued for additional 1 h. It was concentrated; the residue was dissolved in 10 mL of dichloromethane. To the solution was added 0.20 g (70%, 0.81 mmol) of 3-chloroperoxybenzoic acid (mCPBA), the mixture was stirred at room temperature for 1 h. It was quenched with 5 mL of 10% sodium thiosulfate solution, 3 mL of 1 N NaOH, and 20 mL of H$_2$O. The mixture was extracted with two 30 mL portions of dichloromethane. The combined organic layers were concentrated; the residue was purified by chromatography eluting with a gradient of 0 to 7% methanol in dichloromethane plus 1% ammonium hydroxide to give a crude, which was crystallized from methanol to give 0.066 g of compound 83. $^1$H NMR (CDCl$_3$ 400 MHz) δ 7.62 (d, J=8.8 Hz, 2H), 7.51 (d,

SCHEME 32

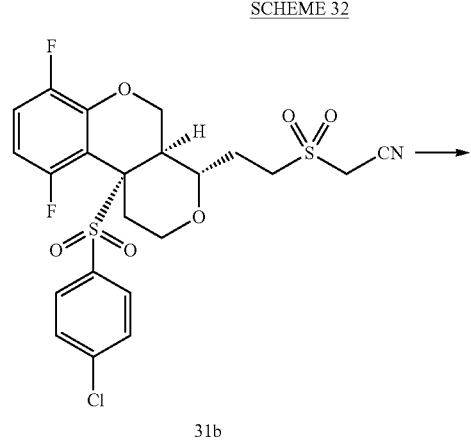

31b

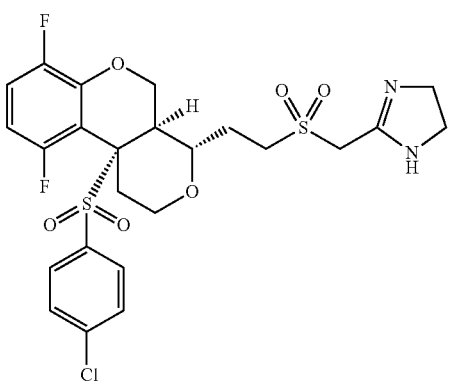

85

A suspension of 0.14 g (0.28 mmol) of compound 31b and 0.006 g (0.19 mmol) of sulfur in 4 mL of ethylene diamine in a sealed tube was heated at 100° C. in microwave for 15 min. It was concentrated; the residue was purified by chromatography to give a crude intermediate (0.06 g), which was dissolved in 12 mL of dichloromethane. To the solution were added 0.07 g of trifluoroacetic acid and 0.10 g (70%, 0.40 mmol) of 3-chloroperoxybenzoic acid (mCPBA), the mixture was stirred at room temperature for 1.5 h. It was quenched with 5 mL of 10% sodium thiosulfate solution, 6 mL of 0.5 N NaOH solution. The mixture was extracted with two 20 mL portions of dichloromethane. The combined organic layers were concentrated; the residue was purified by chromatography eluting with a gradient of 0 to 8% methanol in dichloromethane plus 1% ammonium hydroxide to give 0.48 g of compound 85. $^1$H NMR (CDCl$_3$ 400 MHz) δ 7.62 (d, J=8.4 Hz, 2H), 7.49 (d, J=8.4 Hz, 2H), 7.08 (m, 1H), 6.46 (m, 1H), 5.14 (dd, J=12.8, 2.8 Hz, 1H), 4.45 (d, J=12.4 Hz, 1H), 3.90 (br, 2H), 3.88 (m, 1H), 3.60 (br, 4H), 3.35 (m, 2H), 3.10 (m, 2H), 2.55 (m, 2H), 2.40 (m, 1H), 2.25 (m, 1H), 2.02 (m, 1H). LCMS: Calcd. for C$_{24}$H$_{26}$ClF$_2$N$_2$O$_6$S$_2$, 575.1 (MH$^+$). found 575.3. Retention time: 3.12/7.5 min.

SCHEME 33

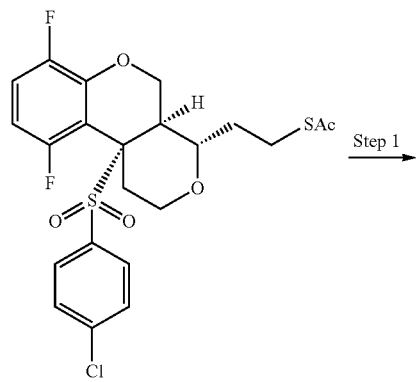

28

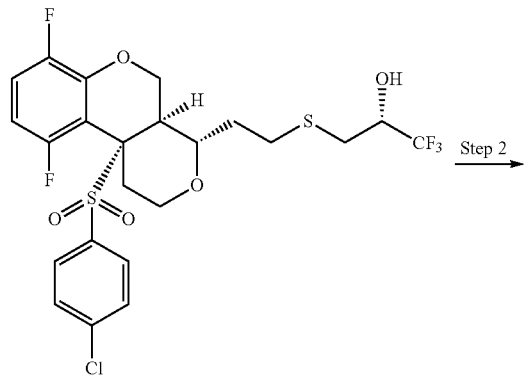

86

87

88a

88b

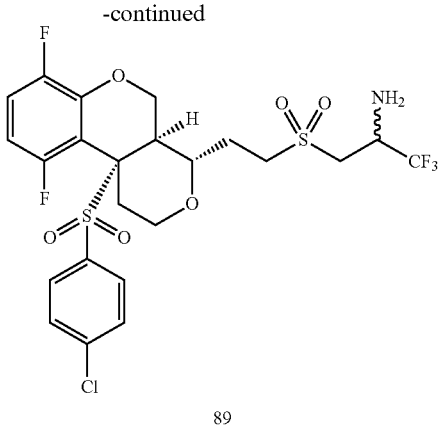

89

Step 1

To a suspension of 0.50 g (1.0 mmol) of compound 28 in 20 mL of anhydrous methanol was added 0.14 g (2.0 mmol) of potassium methoxide at room temperature. After 10 min., 0.20 g (1.79 mmol) of (R)-3,3,3-trifluoroepoxypropane was added, and the stirring was continued for additional 3 h. It was quenched with one drop of water, and concentrated; the residue was dissolved in 30 mL of water. It was extracted with two 40 mL portions of dichloromethane. The combined organic layers were concentrated; the residue was purified by chromatography eluting with a gradient of 0 to 40% ethyl acetate in hexanes to give 0.56 g of crude compound 86. $^1$H NMR (CDCl$_3$ 400 MHz) δ 7.62 (d, J=8.4 Hz, 2H), 7.50 (d, J=8.4 Hz, 2H), 7.10 (m, 1H), 6.44 (m, 1H), 5.15 (dd, J=12.4, 2.8 Hz, 1H), 4.41 (d, J=12.4 Hz, 1H), 4.0 (m, 1H), 3.90 (m, 1H), 3.38 (m, 1H), 3.10 (m, 2H), 2.60-2.90 (m, 5H), 2.50 (m, 1H), 2.30 (m, 1H), 2.15 (m, 1H), 1.82 (m, 1H). LCMS: Calcd. for C$_{23}$H$_{23}$ClF$_5$O$_5$S$_2$, 573.1 (MH$^+$). found 573.3. Retention time: 4.86/7.5 min.

Step 2

To a solution of 0.18 g (0.31 mmol) of compound 86 in 10 mL of dichloromethane was added 0.25 g (70%, 1.0 mmol) of 3-chloroperoxybenzoic acid (mCPBA), the mixture was stirred at room temperature for 1 h. It was quenched with 5 mL of 10% sodium thiosulfate solution, 3 mL of 1 N NaOH, and 15 mL of water. The mixture was extracted with two 30 mL portions of dichloromethane. The combined organic layers were concentrated; the residue was purified by chromatography eluting with a gradient of 0 to 60% ethyl acetate in hexanes to give 0.12 g of crude compound 87. $^1$H NMR (CDCl$_3$ 400 MHz) δ 7.62 (d, J=7.6 Hz, 2H), 7.50 (d, J=7.6 Hz, 2H), 7.10 (m, 1H), 6.47 (m, 1H), 5.16 (dd, J=12.4, 2.4 Hz, 1H), 4.64 (m, 1H), 4.44 (d, J=12.4 Hz, 1H), 3.88 (m, 1H), 3.10-3.50 (m, 6H), 2.40-2.60 (m, 3H), 2.30 (m, 1H), 2.10 (m, 1H). LCMS: Calcd. for C$_{23}$H$_{23}$ClF$_5$O$_7$S$_2$ (MH$^+$), 605.1. found 605.3. Retention time: 4.52/7.5 min.

Step 3

A solution of 0.34 g (0.56 mmol) of compound 87 and 0.16 g (2.0 mmol) of pyridine in 6 mL of dichloromethane was cooled to −40° C. To this solution, 0.285 g (1.0 mmol) of triflic anhydride was added; the mixture was stirred at the same temperature for 0.5 h, and then warmed to −20° C. over a period of 1 h. It was quenched with one drop of water, and concentrated. The residue was purified by chromatography eluting with a gradient of 0 to 50% ethyl acetate in hexanes to give 0.37 g of mixture 88a and 88b. 88a: $^1$H NMR (CDCl$_3$ 400 MHz) δ 7.62 (d, J=8.0 Hz, 2H), 7.50 (d, J=8.0 Hz, 2H), 7.10 (m, 1H), 6.47 (m, 1H), 5.65 (m, 1H), 5.15 (dd, J=12.4, 2.4 Hz, 1H), 4.40 (d, J=12.4 Hz, 1H), 3.90 (m, 1H), 3.60 (m, 1H), 3.10-3.50 (m, 3H), 2.40-2.60 (m, 3H), 2.30 (m, 1H), 2.10 (m, 1H). LCMS: Calcd. for C$_{24}$H$_{21}$ClF$_8$NaO$_9$S$_3$(M+Na), 759.0. found 758.8. Retention time: 2.30/3.6 min.

88b: LCMS: Calcd. for C23H20ClF5NaO6S2 (M+Na), 609.0. found 609.0. Retention time: 2.24/3.6 min.

Step 4

A solution of 0.28 g (0.37 mmol) of mixture 88a and 88b in 2 mL of concentrated ammonium hydroxide and 2 mL of acetonitrile in a sealed tube was stirred at room temperature for 5 h. It was concentrated; the residue was purified by chromatography eluting with a gradient of 0 to 50% ethyl acetate in hexanes to give 0.25 g of compound 89 as a mixture of two diastereoisomers. $^1$H NMR (CDCl$_3$ 400 MHz) δ 7.62 (d, J=8.8 Hz, 2H), 7.50 (d, J=8.8 Hz, 2H), 7.10 (m, 1H), 6.46 (m, 1H), 5.16 (dd, J=12.4, 2.0 Hz, 1H), 4.44 (d, J=12.4 Hz, 1H), 3.90 (m, 2H), 3.50 (m, 1H), 3.05-3.40 (m, 5H), 2.40-2.60 (m, 3H), 2.30 (m, 1H), 2.05 (m, 1H). LCMS: Calcd. for C$_{24}$H$_{21}$ClF$_8$NaO$_9$S$_3$ (MH$^+$), 604.1. found 604.3. Retention time: 4.03/7.5 min.

SCHEME 34

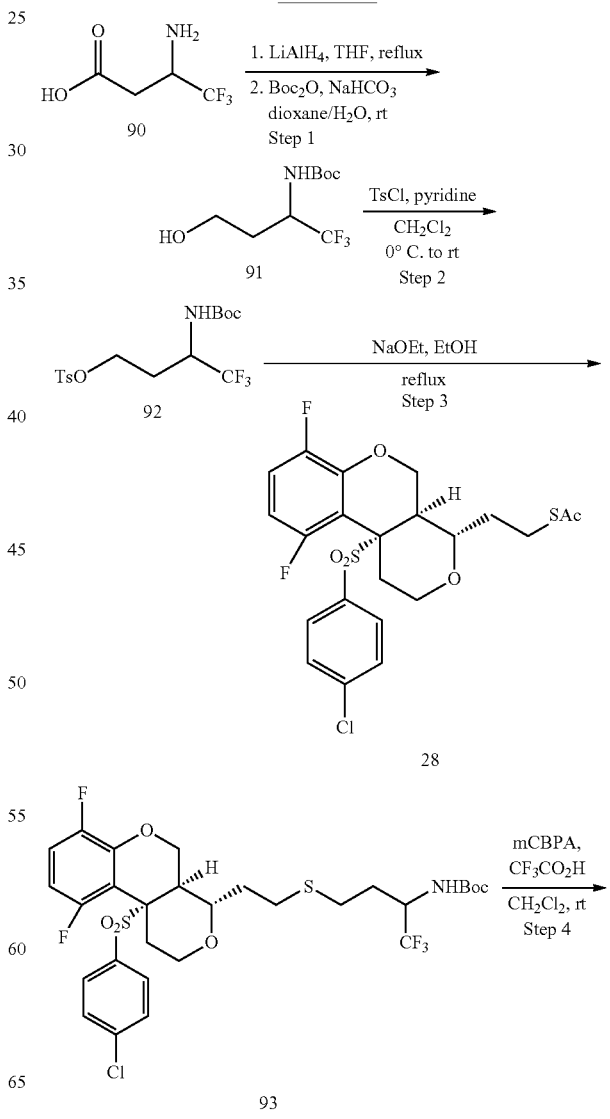

-continued

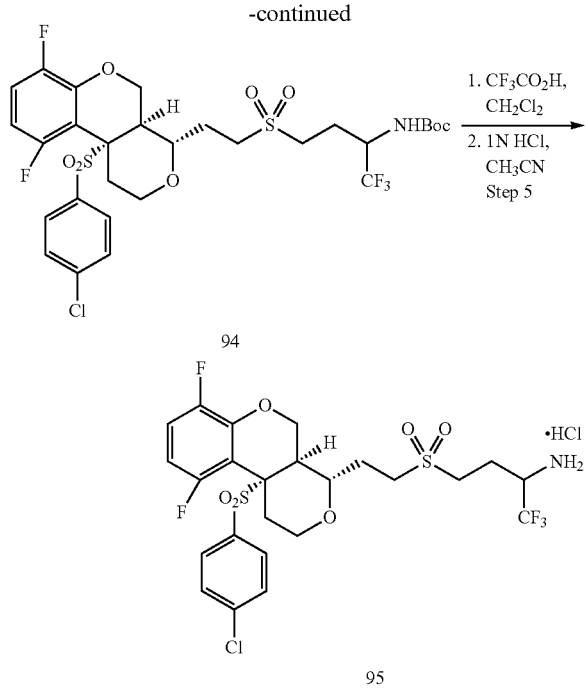

Step 1

To a stirred suspension of 0.604 g (15.9 mmol) of LiAlH$_4$ in 25 mL of anhydrous THF was added 1.01 g (6.36 mmol) of compound 90 in small portions over 30 min at 0° C. under nitrogen. After the addition was complete, the cooling bath was removed and the reaction was warmed to room temperature over 30 min and then refluxed for 2 h. The reaction mixture was cooled to room temperature and diluted with 30 mL of THF, cooled in ice/water bath, quenched with saturated aqueous Na$_2$SO$_4$, and stirred for 3 h. The resulting mixture was filtered through a pad of Celite® and the filtrate was concentrated to give 0.44 g of colorless liquid residue (0.440 g).

To a stirred solution of the above liquid residue in 10 mL of 1,4-dioxane/water (1:1) were added 0.511 g (6.08 mmol) of NaHCO$_3$ and 0.80 g (3.65 mmol) of Boc$_2$O, and the reaction mixture was stirred at room temperature for 18 h. After this time, the reaction mixture was concentrated to remove 1,4-idoxane and the resulting mixture was diluted with 20 mL of water, and extracted with three 20 mL portions of CH$_2$Cl$_2$. The combined organics were dried over anhydrous Na$_2$SO$_4$, filtered, and concentrated. The residue was purified by flash chromatography (silica, 0-50% ethyl acetate/hexanes) to afford 0.39 g (53%) of 91 as a colorless oil: $^1$H NMR (CDCl$_3$ 500 MHz) δ 4.78-4.76 (m, 1H), 4.46-4.41 (m, 1H), 3.78-3.76 (m, 1H), 3.67-3.66 (m, 1H), 2.55-2.52 (m, 1H), 2.09-2.05 (m, 1H), 1.59-1.55 (m, 1H), 1.46 (s, 9H).

Step 2

To a stirred solution of 0.39 g (1.59 mmol) of compound 91 in 4 mL of anhydrous CH$_2$Cl$_2$ was added 0.5 mL of pyridine and 0.457 g (2.40 mmol) of TsCl at 0° C. under nitrogen. The reaction was warmed to room temperature and stirred for 18 h. After this time, the reaction mixture was diluted with 100 mL of EtOAc, washed with two 25 mL portions of saturated aqueous citric acid, dried over anhydrous Na$_2$SO$_4$, filtered, and concentrated. The residue was purified by flash chromatography (silica, 0-10% ethyl acetate/hexanes) to afford 0.426 g (67%) of 92 as a white solid. $^1$H NMR (CDCl$_3$ 500 MHz) δ 7.80 (d, J=8.2 Hz, 2H), 7.36 (d, J=8.2 Hz, 2H), 4.59-4.57 (m, 1H), 4.34-4.28 (m, 1H), 4.16-4.11 (m, 2H), 2.44 (s, 3H), 2.19-2.17 (m, 1H), 1.85-1.83 (m, 1H), 1.43 (s, 9H).

Step 3

To a stirred solution of 0.15 g (0.29 mmol) of compound 92 in 5 mL of EtOH was added freshly prepared solution of NaOEt (0.007 g, 0.289 mmol of sodium in 1 mL of EtOH). The reaction was stirred at room temperature for 1 h and then a solution of 0.177 g (0.442 mmol) of compound 28 in 1 mL of EtOH was added. The reaction was heated at reflux for 18 h. After this time, the reaction was cooled to room temperature and concentrated. The residue was purified by flash chromatography (silica, 0-15% ethyl acetate/hexanes) to afford 0.14 g (68%) of 93 as a white solid: MS: Calcd. for C$_{29}$H$_{33}$ClF$_5$NNaO$_6$S$_2$ (MNa$^+$), m/z=708.1. found 708.1. Retention time: 3.73 min.

Step 4

To a stirred solution of 0.14 g (0.20 mmol) of compound 93 in 4 mL of CH$_2$Cl$_2$ was added 0.16 mL (2.0 mmol) of TFA and 0.145 g (0.82 mmol) of mCPBA and the reaction was stirred at room temperature for 18 h. After this time, the reaction mixture was quenched with 5 mL of saturated aqueous NaHCO$_3$. The aqueous layer was separated and extracted with three 20 mL portions of CH$_2$Cl$_2$. The combined organics were dried over anhydrous sodium sulfate, filtered, and concentrated. The residue was purified by flash chromatography (silica, 0-50% ethyl acetate/hexanes) to afford 0.088 g (60%) of 94 as a white solid: $^1$H NMR (CDCl$_3$ 500 MHz) δ 7.63 (d, J=8.3 Hz, 2H), 7.51 (d, J=8.2 Hz, 2H), 7.13-7.08 (m, 1H), 6.50-6.45 (m, 1H), 5.18 (dd, J=12.4, 2.5 Hz, 1H), 4.73-4.71 (m, 1H), 4.44 (d, J=16.0 Hz, 1H), 4.33-4.33 (m, 1H), 3.91-3.88 (m, 1H), 3.36-3.32 (m, 1H), 3.28-3.21 (m, 1H), 3.14 (t, J=12.1 Hz, 1H), 3.09-2.27 (m, 3H), 2.56 (t, J=10.1 Hz, 2H), 2.47-2.42 (m, 1H), 2.35-2.27 (m, 2H), 2.03-2.01 (m, 2H), 1.46 (s, 9H). Compound 95 (0.025 g, 20%) was also isolated as a white solid.

Step 5

A solution of 0.088 g (0.122 mmol) of compound 94 and 0.5 mL of TFA in 3 mL of CH$_2$Cl$_2$ was stirred for 5 h. The reaction was concentrated and the residue was dissolved in 50 mL of CH$_2$Cl$_2$, washed with 5 mL of saturated aqueous NaHCO$_3$, dried over anhydrous Na$_2$SO$_4$, filtered, and concentrated. The residue was purified by flash chromatography (silica, 0-5% MeOH/CH$_2$Cl$_2$) to afford 0.060 g (80%) of 95. $^1$H NMR (CDCl$_3$ 500 MHz) δ 8.86-8.84 (br s, 2H), 7.76-7.72 (m, 4H), 7.44-7.39 (m, 1H), 6.78-6.73 (m, 1H), 4.93 (dd, J=12.3, 2.4 Hz, 1H), 4.57 (d, J=13.4 Hz, 1H), 4.25 (br s, 1H), 3.93-3.90 (m, 1H), 3.44-3.21 (m, 5H), 3.03 (t, J=11.6 Hz, 1H), 2.53 (d, J=14.2 Hz, 1H), 2.43 (d, J=9.9 Hz, 1H), 2.29-2.24 (m, 1H), 2.19-2.13 (m, 3H), 1.95-1.90 (m, 1H); MS: Calcd. for C$_{24}$H$_{26}$ClF$_5$NO$_6$S$_2$ (MH$^+$), m/z=618.1. found 618.0. Retention time: 2.38 min. HPLC (Method 2) 96.2% (AUC), t$_R$=12.20 min.

SCHEME 35

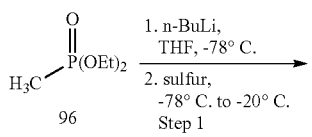

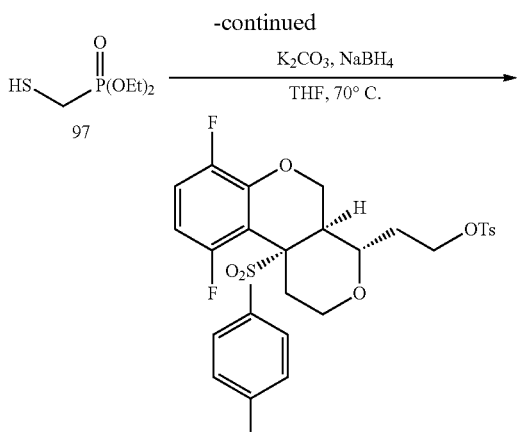

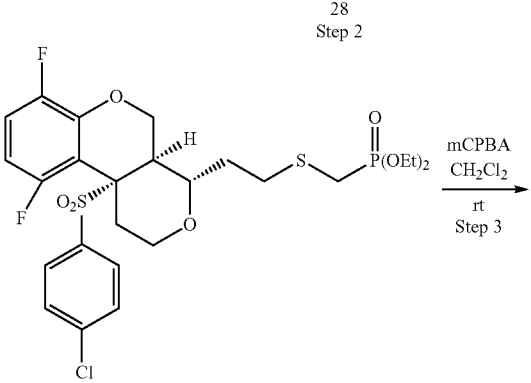

Step 1

To a solution of 5.00 g (32.9 mmol) of compound 96 in anhydrous 66 mL of THF was added dropwise 13.0 mL (2.5 M in hexanes, 32.9 mmol) of n-BuLi at 78° C. under nitrogen and the mixture was stirred for 30 min. After this time, 1.10 g (32.9 mmol) of sulfur was added and the reaction mixture was warmed to 20° C. over 1 h. After this time, the reaction was quenched with 15 mL of aqueous 1 N HCl and the aqueous layer was extracted with three 15 mL portions of chloroform. The combined organics were dried over anhydrous MgSO$_4$, filtered, and concentrated under reduced pressure to afford 3.69 g (61%) of 96, which was used in the subsequent step without further purification: MS: Calcd. for C$_5$H$_{14}$O$_3$PS (MH$^+$), m/z=185.0; found 185.2. Retention time: 1.92 min. Ref: Mikolajczyk, M.; Grzejszczak, S.; Chefczynska, A.; Zatorski, A. J. Org. Chem. 1979, 44, 2967-2972.

Step 2

A suspension of 0.30 g (0.50 mmol) of compound 97, 0.057 g (1.50 mmol) of sodium borohydride, and 0.346 g (2.50 mmol) of potassium carbonate in 5 mL of methanol was stirred at room temperature for 20 min. Compound 28 (0.369 g, 0.410 mmol) was added and the reaction was heated at 70° C. for 2 h. After this time, the reaction was cooled to room temperature, diluted with 10 mL of saturated aqueous NH$_4$Cl, and extracted with three 10 mL portions of methylene chloride. The combined organics were dried over anhydrous MgSO$_4$, filtered, and concentrated to afford 0.306 g of crude product 98, which was used without further purification: MS: Calcd. for C$_{25}$H$_{30}$ClF$_2$NaO$_7$PS$_2$ (MNa$^+$), m/z=633.1. found 633.1. Retention time: 3.20 min.

Step 3

To a stirred solution of 0.306 g of crude 98 in 5 mL of methylene chloride was added 0.43 g (2.50 mmol) of mCPBA. The reaction was stirred at room temperature for 3 h. After this time, the reaction was diluted with 40 mL of methylene chloride, washed with 50 mL of 10% Na$_2$S$_2$O$_3$ and 50 mL of saturated aqueous NaHCO$_3$, dried over anhydrous Na$_2$SO$_4$, filtered, and concentrated. The residue was purified by flash chromatography (silica, 0-90% ethyl acetate/heptane) to afford 0.131 g (35% over two steps) of 99 as a white solid: $^1$H NMR (500 MHz, CDCl$_3$) δ 7.64 (d, J=8.6 Hz, 2H), 7.51 (d, J=8.7 Hz, 2H), 7.11 (td, J=9.4, 4.7 Hz, 1H), 6.52-6.43 (m, 1H), 5.17 (dd, J=12.7, 2.6 Hz, 1H), 4.47 (d, J=12.5 Hz, 1H), 4.29-4.16 (m, 4H), 3.95-3.85 (m, 1H), 3.66-3.49 (m, 3H), 3.42-3.32 (m, 2H), 3.13 (t, J=11.6 Hz, 1H), 2.55 (t, J=12.3 Hz, 2H), 2.50-2.39 (m, 1H), 2.35-2.23 (m, 1H), 2.17-2.02 (m, 1H), 1.38-1.35 (m, 6H); MS: Calcd. for C$_{25}$H$_{30}$ClF$_2$NaO$_9$PS$_2$ (MNa$^+$), m/z=665.1. found 664.9. Retention time: 3.03 min. HPLC (Method 2) 98.0% (AUC), t$_R$=15.47 min. [α]$^{25}$$_D$=−108.8° (c 0.80, Chloroform).

SCHEME 36

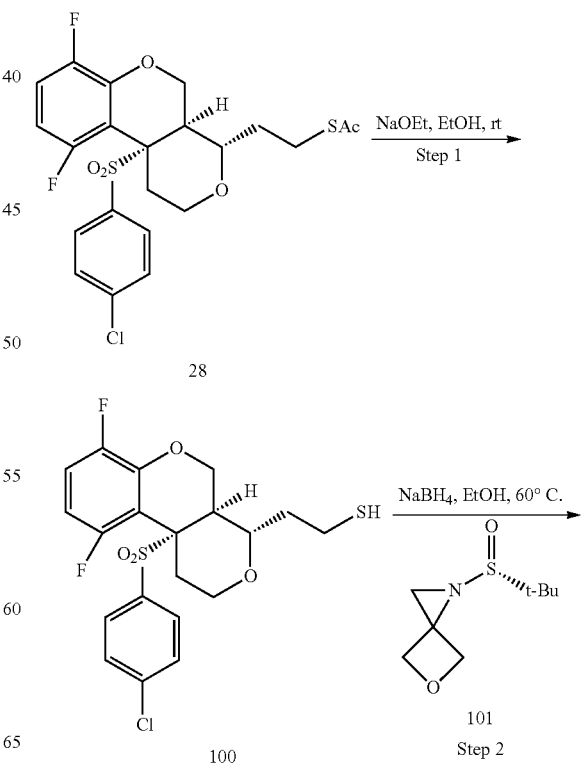

-continued

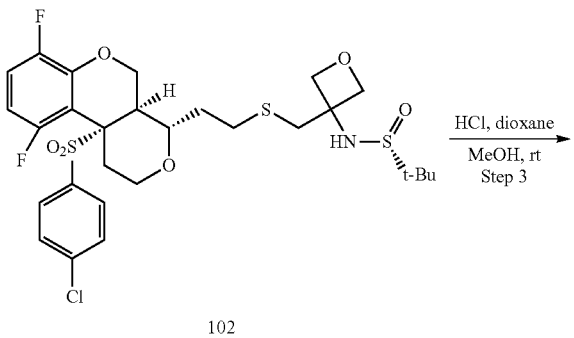

102

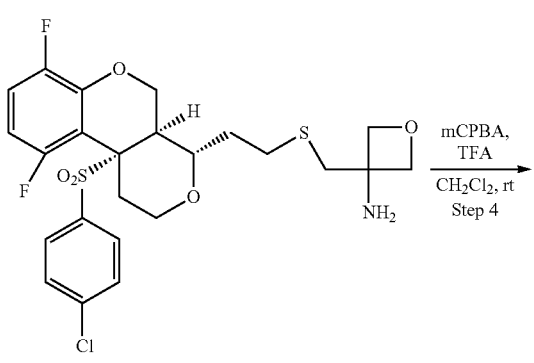

103

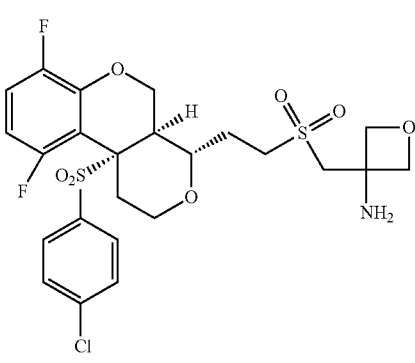

104

Step 1

To a stirred solution of 0.458 g (0.91 mmol) of compound 28 in 15 mL of ethanol was added freshly prepared solution of sodium ethoxide (0.133 g, 5.78 mmol) in 3 mL of ethanol at room temperature under nitrogen. The reaction mixture was stirred at room temperature for 40 min. After this time, the reaction mixture was concentrated and the residue was partitioned between 25 mL of water and 50 mL of methylene chloride. The layers were separated and the aqueous layer was extracted with three 50 mL portions of methylene chloride. The combined organics were dried over anhydrous sodium sulfate, filtered, and concentrated to afford 0.394 g (94%) of 100 as a white solid which was used in the subsequent step without further purification: MS: Calcd. for $C_{20}H_{23}ClF_2NO_4S_2$ ($MNH_4^+$), m/z=478.1. found 478.1. Retention time: 2.37 min.

Step 2

To a stirred solution of 0.39 g (0.85 mmol) of compound 100 in 25 mL of ethanol was added 0.073 g (1.92 mmol) of sodium borohydride at room temperature. After stirring for 5 min, a solution of 0.107 g (0.565 mmol) of compound 101[1] in 5 mL of ethanol was added and the reaction mixture was heated at 60° C. for 1 h. After this time, the reaction was cooled to room temperature and then partitioned between 20 mL of water and 25 mL of methylene chloride. The layers were separated and the aqueous layer was extracted with three 25 mL portions of methylene chloride. The combined organics were washed with 50 mL of brine, dried over anhydrous sodium sulfate, filtered, and concentrated. The residue was purified by flash chromatography [silica, 0-10% (80:18:2 methylene chloride/methanol/ammonium hydroxide)/methylene chloride] to afford 0.322 g (88%) of 102 as a white solid: MS: Calcd. for $C_{28}H_{34}ClF_2NNaO_6S_3$ ($MNa^+$), m/z=672.1. found 672.2. Retention time: 2.19 min.

Note 1: The preparation of compound 101 was previously described; see Hamzik, P. J.; Brubaker, J. D. *Org. Lett.* 2010, 12, 1116-1119.

Step 3

To a stirred solution of 0.322 g (0.50 mmol) of compound 102 in 14 mL of methanol was added 0.19 mL of hydrogen chloride (4 M in 1,4-dioxane, 0.760 mmol) at room temperature. After stirring for 45 min, the reaction mixture was basified with 20 mL of saturated aqueous sodium bicarbonate. The resulting mixture was extracted with three 15 mL portions of methylene chloride. The combined organics were dried over anhydrous sodium sulfate, filtered, and concentrated under reduced pressure to provide 0.273 g (100%) of 103 as an off-white solid which was used in the subsequent step without further purification: MS: Calcd. for $C_{24}H_{27}ClF_2NO_5S_2$ ($MH^+$), m/z=546.1. found 546.0. Retention time: 2.13 min.

Step 4

To a stirred solution of 0.318 g (0.58 mmol) of compound 103 in 25 mL of methylene chloride and 0.43 mL (5.81 mmol) of trifluoroacetic acid was added 0.504 g (2.91 mmol) of mCPBA at room temperature. After stirring for 1 h, a solution of 2 g of sodium thiosulfate in 40 mL of saturated aqueous sodium bicarbonate was added and the resulting mixture was stirred for 30 min. The layers were separated and the aqueous layer was extracted with two 25 mL portions of methylene chloride. The combined organics were dried over anhydrous sodium sulfate, filtered, and concentrated under reduced pressure to provide crude 0.335 g of 104 as an off-white solid: MS: Calcd. for $C_{24}H_{27}ClF_2NO_7S_2$ ($MH^+$), m/z=578.1; found 578.1. Retention time: 2.19 min.

Assay

The pharmacological properties of the compounds of this invention may be evaluated by a number of pharmacological assays. The exemplified pharmacological assays, which are described later, have been carried out with the compounds according to the present invention, as well as with salts thereof.

Gamma-secretase activity was determined as described by Zhang et al. (Biochemistry, 40 (16), 5049-5055, 2001), which is herein incorporated by reference. Activity is expressed either as a percent inhibition or as the concentration of compound producing 50% inhibition of enzyme activity.

Reagents.

Antibodies W02, G2-10, and G2-11 were obtained from Dr. Konrad Beyreuther (University of Heidelberg, Heidelberg, Germany). W02 recognizes residues 5-8 of Aβ peptide, while G2-10 and G2-11 recognize the specific C-terminal structure of Aβ 40 and Aβ 42, respectively. Biotin-4G8 was purchased from Senetec (St. Louis, Mo.). All tissue culture reagents used in this work were from Life Technologies, Inc., unless otherwise specified. Pepstatin A was purchased from Roche Molecular Biochemicals; DFK167 was from Enzyme Systems Products (Livermore, Calif.).

cDNA Constructs, Tissue Culture, and Cell Line Construction.

The construct SPC99-Ion, which contains the first 18 residues and the C-terminal 99 amino acids of APP carrying the London mutation, has been described (Zhang, L., Song, L., and Parker, E. (1999) J. Biol. Chem. 274, 8966-8972). Upon insertion into the membrane, the 17 amino acid signal peptide is processed, leaving an additional leucine at the N-terminus of Aβ. SPC99-Ion was cloned into the pcDNA4/TO vector (Invitrogen) and transfected into 293 cells stably transfected with pcDNA6/TR, which is provided in the T-REx system (Invitrogen). The transfected cells were selected in Dulbecco's modified Eagle's media (DMEM) supplemented with 10% fetal bovine serum, 100 units/mL penicillin, 100 g/mL streptomycin, 250 g/mL zeocin, and 5 g/mL blasticidin (Invitrogen). Colonies were screened for Aβ production by inducing C99 expression with 0.1 g/mL tetracycline for 16-20 h and analyzing conditioned media with a sandwich immunoassay (see below). One of the clones, designated as pTRE.15, was used in these studies.

Membrane Preparation.

C99 expression in cells was induced with 0.1 g/mL tetracycline for 20 h. The cells were pretreated with 1 M phorbol 12-myristate 13-acetate (PMA) and 1 M brefeldin A (BFA) for 5-6 h at 37 C before harvesting. The cells were washed 3 times with cold phosphate-buffered saline (PBS) and harvested in buffer A containing 20 mM Hepes (pH 7.5), 250 mM sucrose, 50 mM KCl, 2 mM EDTA, 2 mM EGTA, and Complete protease inhibitor tablets (Roche Molecular Biochemicals). The cell pellets were flash-frozen in liquid nitrogen and stored at −70° C. before use.

To make membranes, the cells were resuspended in buffer A and lysed in a nitrogen bomb at 600 psi. The cell lysate was centrifuged at 1500 g for 10 min to remove nuclei and large cell debris. The supernatant was centrifuged at 100000 g for 1 h. The membrane pellet was resuspended in buffer A plus 0.5 M NaCl, and the membranes were collected by centrifugation at 200000 g for 1 h. The salt-washed membrane pellet was washed again in buffer A and centrifuged at 100000 g for 1 h. The final membrane pellet was resuspended in a small volume of buffer A using a Teflon-glass homogenizer. The protein concentration was determined, and membrane aliquots were flash-frozen in liquid nitrogen and stored at −70° C.

γ-Secretase Reaction and Aβ Analysis.

To measure γ-secretase activity, membranes were incubated at 37° C. for 1 h in 50 μL of buffer containing 20 mM Hepes (pH 7.0) and 2 in M EDTA. At the end of the incubation, Aβ 40 and Aβ 42 were measured using an electrochemiluminescence (ECL)-based immunoassay. Aβ 40 was identified with antibody pairs TAG-G2-10 and biotin-W02, while Aβ 42 was identified with TAG-G2-11 and biotin-4G8. The ECL signal was measured using an ECL-M8 instrument (IGEN International, Inc.) according to the manufacturer's instructions. The data presented were the means of the duplicate or triplicate measurements in each experiment. The characteristics of γ-secretase activity described were confirmed using more than five independent membrane preparations.

As shown below in the Table, the compounds of the invention had a membrane $IC_{50}$ in the range of 0.5 nM to 18.9 nM.

TABLE

| Compound | R | $A\beta_{40}$ $IC_{50}$ (nM) |
|---|---|---|
| 6a | —CH₂CH₂—NMe₂ | 1.7 |
| 6b | —CH₂CH₂—NEt₂ | 2.6 |
| 6c | —CH₂CH₂—NHMe | 0.9 |
| 6d | —CH₂CH₂—NH-cyclobutyl | 2.0 |
| 6e | —CH₂CH₂—azetidinyl | 1.6 |
| 6f | —CH₂CH₂—pyrrolidinyl | 1.1 |
| 6g | —CH₂CH₂—piperidinyl | 1.3 |
| 6h | —CH₂CH₂—morpholinyl | 3.7 |
| 6i | —CH₂CH₂—NHMe | 4.1 |
| 6j | —CH₂CH₂—NH₂ | 0.8 |

TABLE-continued
| | | |
|---|---|---|
| 6k | 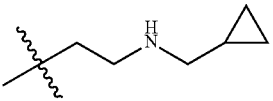 [SMILES: *CCNCC1CC1] | 1.2 |
| 6l | 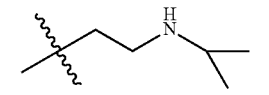 [SMILES: *CCNC(C)C] | 0.5 |
| 6m | 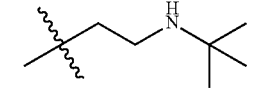 [SMILES: *CCNC(C)(C)C] | 0.6 |
| 6n | 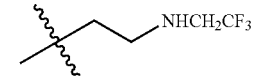 NHCH$_2$CF$_3$ | 7.4 |
| 6o | 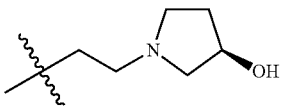 [SMILES: *CCN1CC[C@@H](O)C1] | 0.6 |
| 6p | 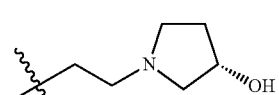 | 0.8 |
| 6q | 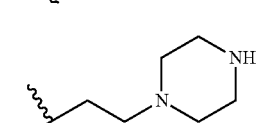 | 0.8 |
| 6r | 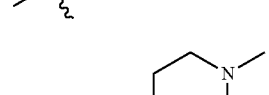 | 0.6 |
| 6s | 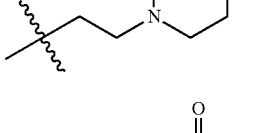 | 3.8 |
| 6t | 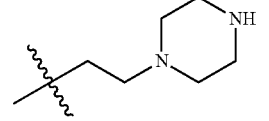 | 1.8 |
| 9a |  | 4.5 |
| 9b | 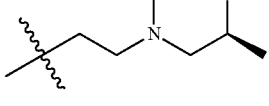 | 4.9 |
TABLE-continued
| | | |
|---|---|---|
| 9c | 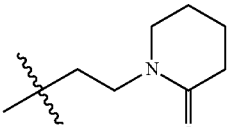 | 3.3 |
| 9d | 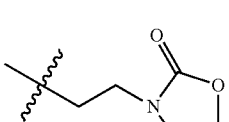 | 4.6 |
| 9e | 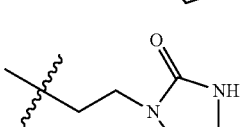 | 0.8 |
| 24a | 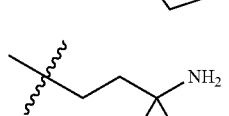 | 1.3 |
| 24b | 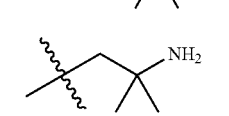 | 5.7 |
| 24c | 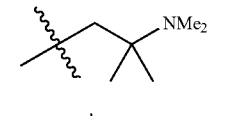 | 6.5 |
| 26e | 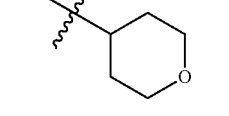 | 2.4 |
| 26f | 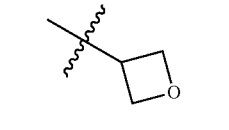 [SMILES: *C1COC1] | 4.4 |
| 26g | 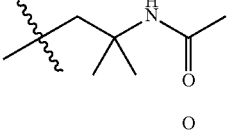 | 7.8 |
| 26h | 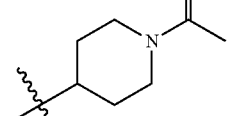 | 4.0 |
| 26i | 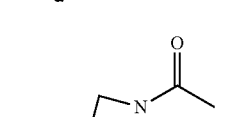 | 1.9 |
| 27a |  | 1.0 |

TABLE-continued

| | | |
|---|---|---|
| 27b | [pyrrolidine, CH2 linker, (S)] | 0.7 |
| 27c | [pyrrolidin-3-yl, dashed wedge] | 3.8 |
| 27d | [pyrrolidin-3-yl, bold wedge, methyl] | 1.4 |
| 27e | [piperidin-4-yl] | 1.3 |
| 27f | [1-aminocyclopentyl-CH2] | 5.1 |
| 27g | [azetidin-3-yl] | 1.3 |
| 31b | [CH2CN, gem-dimethyl] | 2.3 |
| 31c | [1-aminocyclopropyl-CH2] | 6.3 |
| 31d | [CH2C(O)NH2] | 0.8 |
| 32 | [azetidin-3-yl-CH2] | 1.8 |
| 33 | [CH2C(=S)NH2] | 1.3 |
| 34 | [C(CH3)2OH, CH2 linker] | 1.2 |
| 36 | [C(CH3)2NHMe, CH2 linker] | 2.2 |

TABLE-continued

| | | |
|---|---|---|
| 39a | [(CH2)3NHMe] | 3.8 |
| 39b | [(CH2)3N(Me)(tBu)] | 2.4 |
| 39c | [(CH2)3NH-tBu] | 1.4 |
| 39d | [(CH2)3NHCH2CF3] | 8.2 |
| 39e | [(CH2)3NMe2] | 1.3 |
| 39f | [(CH2)2-(4-methylpiperazin-1-yl)] | 1.3 |
| 39g | [(CH2)3-pyrrolidin-1-yl] | 7.2 |
| 43a | [(CH2)3-azetidin-2-one-N-yl] | 3.0 |
| 43b | [(CH2)3-2-pyrrolidinone-N-yl] | 17.0 |
| 43c | [(CH2)3-2-piperidinone-N-yl] | 3.4 |
| 45 | [(CH2)3C(O)NH2] | 0.9 |
| 46a | [(CH2)3N(Me)C(O)Me] | 3.5 |
| 46b | [(CH2)3N(CH2CF3)C(O)Me] | 17.0 |

TABLE-continued

| # | Structure | Value |
|---|---|---|
| 46c | N-tert-butyl-N-acetyl aminobutyl | 18.5 |
| 46d | N-methyl-N-acetyl aminopropyl | 8.0 |
| 47 | 3-methyl-1-methylpyrrolidin-3-yl | 4.1 |
| 51a | 2-methyl-2-carbamoylpropyl | 3.2 |
| 51b | N-tert-butyl-2,2-dimethylpropanamide | 5.3 |
| 51c | N-tert-butyl-2,2-dimethylpropanamide | 18.9 |
| 51d | N-methyl-2,2-dimethylpropanamide | 2.0 |
| 56a | N-(oxetan-3-yl)-3-methylbutanamide | 3.5 |
| 56b | 1-(pyrrolidin-1-yl)-3-methylbutan-1-one | 4.0 |
| 56c | 1-(azetidin-1-yl)-3-methylbutan-1-one | 3.0 |
| 56d | N-tert-butyl-3-methylbutanamide | 10.5 |
| 56e | N-methyl-3-methylbutanamide | 1.4 |

TABLE-continued

| # | Structure | Value |
|---|---|---|
| 56f | N-cyclopropyl-3-methylbutanamide | 3.0 |
| 63c | 5-oxopyrrolidin-2-ylmethyl | 16.8 |
| 63d | 5-oxopyrrolidin-2-ylmethyl | 9.5 |
| 63e | 3-methyl-2-oxopyrrolidin-3-yl | 0.7 |
| 64a | piperidin-2-ylmethyl | 1.8 |
| 64b | piperidin-2-ylmethyl | 2.1 |
| 64c | 3-methylpiperidin-3-yl | 2.2 |
| 64d | piperidin-3-yl | 0.8 |
| 75 | 2-methylpyrrolidin-2-ylmethyl | 6.6 |
| 76a | 1,2-dimethylpyrrolidin-2-ylmethyl | 13.1 |
| 76b | 3-methyl-1-methylpiperidin-3-yl | 1.7 |
| 82a | 2-carbamoyl-3-methylbutyl | 0.8 |

TABLE-continued

| | | Aβ40 IC50 (nM) |
|---|---|---|
| 82b | cyclobutyl-C(O)NH2 | 2.1 |
| 82c | CH(CH3)-C(O)NH2 | 0.6 |
| 82d | CH(Et)-C(O)NH2 | 0.6 |
| 83 | CH2-S(O)2-CH3 | 4.2 |
| 84 | CH2CH2-S(O)2-CH3 | 4.0 |
| 85 | CH2-(4,5-dihydroimidazol-2-yl) | 3.3 |
| 87 | CH(OH)-CF3 | 6.7 |
| 89 | CH(NH2)-CF3 | 2.1 |
| 95 | CH2CH2-CH(NH2)-CF3 | 3.7 |
| 99 | CH2-P(O)(OEt)2 | 4.8 |

| Compound | Structure | Aβ40 IC50 (nM) |
|---|---|---|
| 31e | (structure with F, F, SO2-aryl-CF3, CH2CH2-S(O)2-CH2-C(O)NH2) | 1.8 |

While the present invention has been described in conjunction with the specific embodiments set forth above, many alternatives, modification and variations thereof will be apparent to those of ordinary skill in the art. All such alternatives, modifications and variations are intended to fall within the spirit and scope of the present invention.

What is claimed is:

1. A compound of Formula (I)

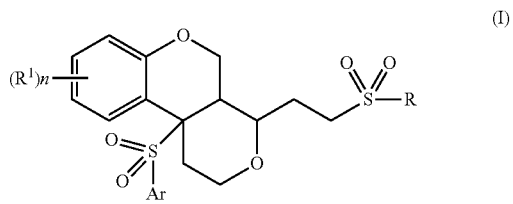

or a pharmaceutically acceptable salt thereof, wherein
R is —(C1-C6)alkylNR$^2$R$^3$, —(C1-C6)alkyl R$^4$;
R$^1$ is independently selected from the group consisting halogen, (C1-C6)alkyl, —CN, —CF$_3$, —O—(C1-C6)alkyl, —O-(halo(C1-C6)alkyl), —C(O)—O—(C1-C6)—OH-substituted (C1-C4)alkyl, halo (C1-C6)alkyl, —(C1-C4)alkoxy-OH, —(C1-C4)alkoxy (C1-C4)alkoxy and —S(O)$_2$(C1-C6)alkyl;
n is 0, 1, 2, 3;
R$^2$ is H or (C1-C6)alkyl;
R$^3$ is H, alkyl, halo(C1-C6)alkyl, —(C3-C6)cycloalkyl, —(C1-C3)alkyl-(C3-C6)cycloalkyl optionally substituted with 1 or 2 L$^1$ groups or —C(O)—(C1-C6) alkyl;
R$^4$ is —CN, —OH-substituted halo(C1-C6)alkyl, —(C3-C6)cycloalkyl optionally substituted with 1 or 2 L$^1$ groups, —(C3-C5)heterocycloalkyl containing 1-2 heteroatoms selected from N and O optionally substituted with 1 or 2 L$^1$ groups, —C(O)NH$_2$, —C(S)NH$_2$, —C(O)NH—(C1-C4)alkyl, —C(O)NH—(C3-C5)heterocycloalkyl containing 1-2 heteroatoms selected from N and O, —C(O)—NH—(C3-C6)cycloalkyl, —C(O)—(C3-C5)heterocycloalkyl containing 1-2 heteroatoms selected from N and O, —N((C$_1$-C$_4$)alkyl)-C(O)—(C1-C3) alkyl, —N((C1-C4)haloalkyl)-C(O)(C1-C3)alkyl), —S(O)$_2$—(C1-C3)alkyl and —P(O)—((C1-C3) alkoxy)$_2$;
L$^1$ is independently selected from the group consisting of —CH$_3$, —NH$_2$, —OH, —C(O)—CH$_3$, =O and —C(O)—NH$_2$;
Ar is selected from the group consisting of phenyl optionally substituted with 1 or 2 L$^2$ groups, and pyridyl optionally substituted with 1 or 2 L$^2$ groups; and
L$^2$ is independently selected from the group consisting of: halogen, (C1-C6)alkyl, —CN, —CF$_3$, —O—(C1-C6)alkyl, —O-(halo(C1-C6)alkyl), —C(O)—O—(C1-C6)alkyl, —OH— substituted(C1-C6)alkyl, halo(C1-C6)alkyl, —OH-substituted (C1-C4)alkoxy, —(C1-C4)alkoxy(C1-C4)alkoxy and —S(O)$_2$(C1-C6)alkyl.

2. The compound of claim 1 or a pharmaceutically acceptable salt thereof, wherein n is 2, each R$^1$ is the same or different halogen, and the R$^1$ groups are bound to the phenyl moiety as shown in formula (II):

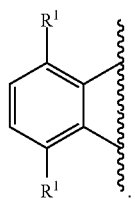

3. The compound of claim 2 or a pharmaceutically acceptable salt thereof, wherein the halogen is fluoro.

4. The compound of claim 3 or a pharmaceutically acceptable salt thereof, wherein Ar is selected from the group consisting of
p-Cl-phenyl-, p-CN-phenyl-, p-CF$_3$-phenyl, pyridyl, and pyridyl substituted with 1 or 2 substituents independently selected from the group consisting of halogen, —(C1-C6)alkyl, —CN, —CF$_3$, —O—(C1-C6)alkyl, —O-halo(C1-C6)alkyl, —C(O)—O—(C1-C6)alkyl, —OH-substituted (C1-C6)alkyl, -halo($C_1$-$C_6$)alkyl, —OH substituted (C1-C4)alkoxy and —(C1-C4)alkoxy (C1-C4)alkoxy.

5. The compound of claim 4 or a pharmaceutically acceptable salt thereof, wherein Ar is selected from the group consisting of p-Cl-phenyl- and p-CF$_3$-phenyl.

6. The compound of claim 1 or a pharmaceutically acceptable salt thereof, wherein R is —(C1-C3)alkyl-R$^4$.

7. The compound of claim 6 or a pharmaceutically acceptable salt thereof, wherein R$^4$ is —C(O)NH$_2$.

8. The compound of claim 1 or a pharmaceutically acceptable salt thereof, wherein the (C3-C5)heterocycloalkyl of R$^4$ is selected from the group consisting of piperidyl, pyrrolidinyl, piperazinyl, morpholinyl, thiomorpholinyl, thiazolidinyl, oxazolidinyl, azetidinyl, tetrahydrofuranyl, tetrahydropyran, oxetin, imidazolinyl and tetrahydrothiophenyl.

9. The compound of claim 1 or a pharmaceutically acceptable salt thereof, having the formula:

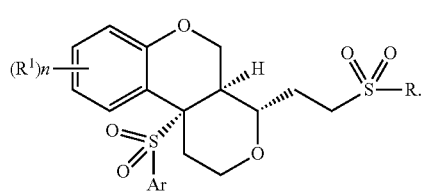

10. The compound of claim 9 or a pharmaceutically acceptable salt thereof, wherein Ar is p-Cl-phenyl or p-CF$_3$-phenyl, n is 2,
each R$^1$ is the same or different halogen, and the R$^1$ groups are bound to the phenyl moiety as shown in formula (II):

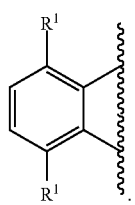

11. The compound of claim 10 or a pharmaceutically acceptable salt thereof, wherein R is —(C1-C3)alkyl-R$^4$ and R$^4$ is —C(O)NH$_2$.

12. A compound which is selected from the group consisting of:

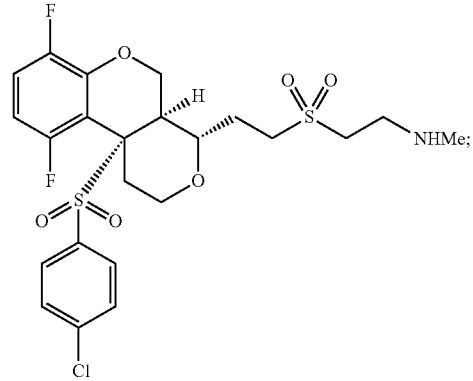

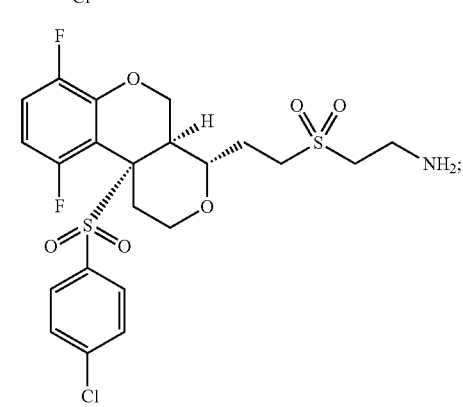

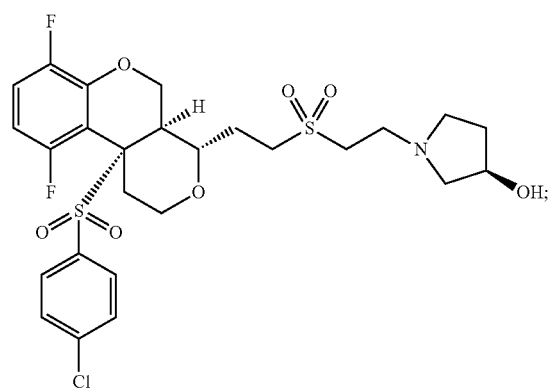

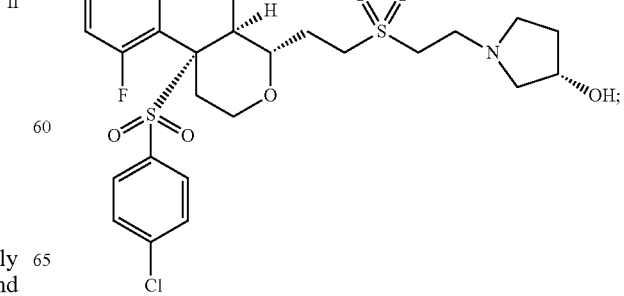

123 -continued
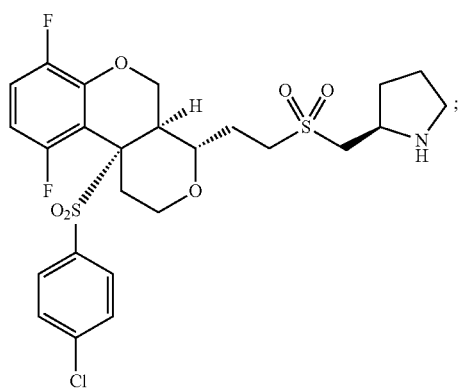
27a
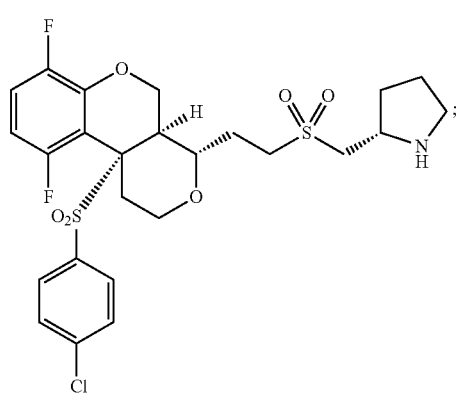
27b
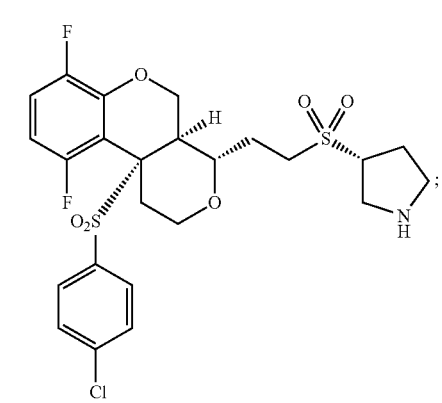
27c
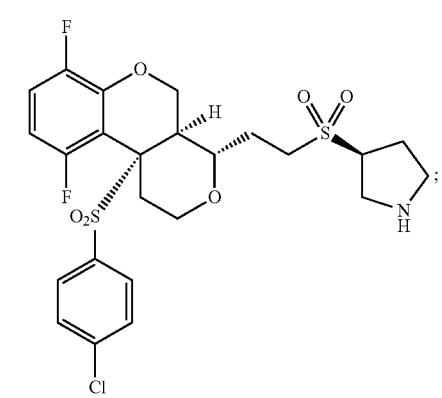
27d
124 -continued
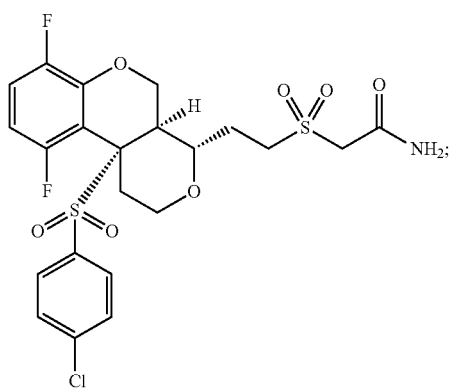
31d
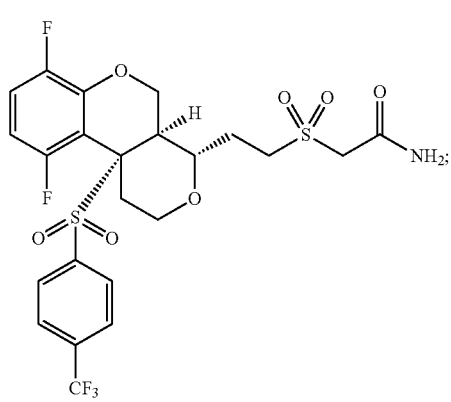
31e
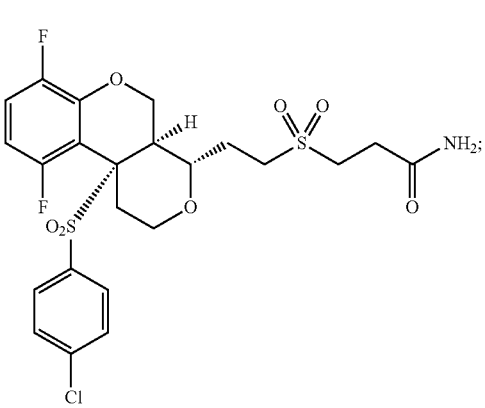
45
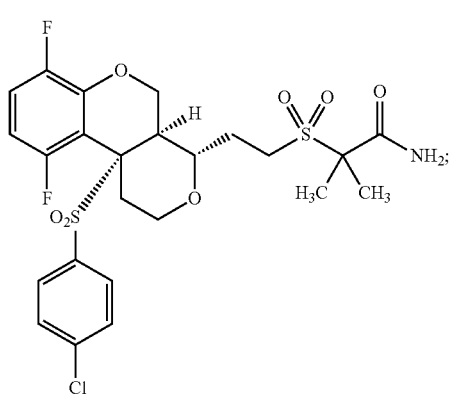
51a

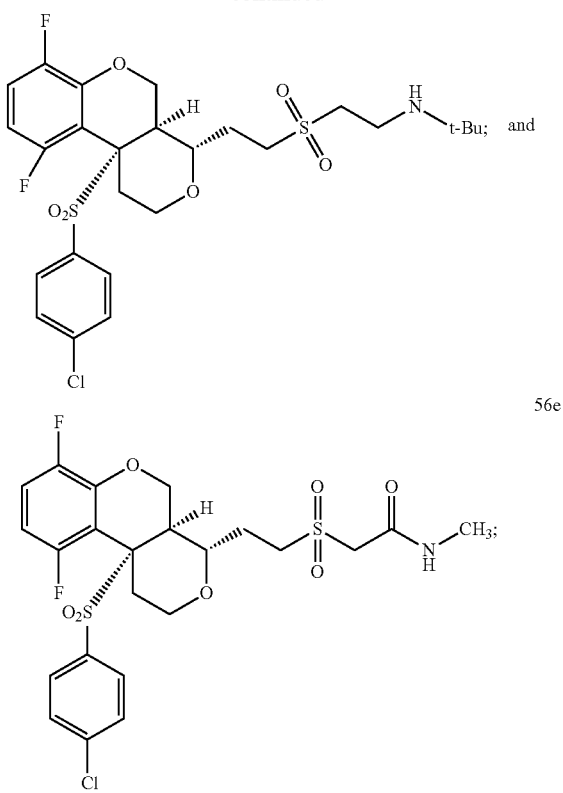

or a pharmaceutically acceptable salt thereof.

13. The compound of claim 12 which is or a pharmaceutically acceptable salt thereof.

14. A pharmaceutical composition comprising a compound of claim 1 or a pharmaceutically acceptable salt thereof, and at least one pharmaceutically acceptable carrier.

15. A pharmaceutical composition comprising the compound of claim 13 or a pharmaceutically acceptable salt thereof, and at least one pharmaceutical acceptable carrier.

* * * * *